US011565074B2

(12) United States Patent
Budhiraja et al.

(10) Patent No.: US 11,565,074 B2
(45) Date of Patent: Jan. 31, 2023

(54) HUMIDIFICATION DEVICE AND SYSTEM

(71) Applicant: Fisher & Paykel Healthcare Limited, Auckland (NZ)

(72) Inventors: Nimansha Budhiraja, Auckland (NZ); Adam John Darby, Auckland (NZ); Johannes Nicolaas Bothma, Auckland (NZ); Mark Samuel Hamilton, Auckland (NZ); Donald Roy Kuriger, Auckland (NZ); Igor Olegovich Yatsevich, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 420 days.

(21) Appl. No.: 16/605,919

(22) PCT Filed: Apr. 27, 2018

(86) PCT No.: PCT/IB2018/052923
§ 371 (c)(1),
(2) Date: Oct. 17, 2019

(87) PCT Pub. No.: WO2018/198081
PCT Pub. Date: Nov. 1, 2018

(65) Prior Publication Data
US 2020/0069904 A1   Mar. 5, 2020

Related U.S. Application Data

(60) Provisional application No. 62/491,165, filed on Apr. 27, 2017.

(51) Int. Cl.
*A61M 16/16*   (2006.01)
*A61M 16/10*   (2006.01)
(Continued)

(52) U.S. Cl.
CPC ........ *A61M 16/16* (2013.01); *A61M 16/0066* (2013.01); *A61M 16/109* (2014.02);
(Continued)

(58) Field of Classification Search
CPC .. A61M 16/00; A61M 16/1045; A61M 16/16; F24F 6/04; F24F 6/043; F24F 6/08; F24F 6/10
See application file for complete search history.

(56) References Cited

U.S. PATENT DOCUMENTS 4,676,237 A * 6/1987 Wood .................... A61M 16/16
128/203.17
5,255,674 A * 10/1993 Oftedal ................. A61M 16/16
128/203.16
(Continued)

FOREIGN PATENT DOCUMENTS

WO   WO 2008/095245   8/2008
WO   WO 2014/142677   9/2014
(Continued)

OTHER PUBLICATIONS

Patent Cooperation Treaty, International Search Report and Written Opinion, Application No. PCT/IB2018/052923, dated Jun. 18, 2018, in 20 pages.

*Primary Examiner* — Joseph D. Boecker
(74) *Attorney, Agent, or Firm* — Knobbe, Martens, Olson & Bear, LLP

(57) ABSTRACT

The invention relates to a non-heated humidification device comprising a wick; a chamber for holding water in contact with the wick; and a gas inlet to the chamber, wherein the chamber and wick are configured to humidify gas passing through or over the wick at ambient conditions. The device may be modular and attachable to a flow generator. The device may comprise dual gas circuits and a control system
(Continued)

for controlling the gas flow through the gas circuits in order to control the humidity of the gas output.

25 Claims, 58 Drawing Sheets

(51) Int. Cl.
    *A61M 16/20*     (2006.01)
    *A61M 16/00*     (2006.01)

(52) U.S. Cl.
    CPC ........ *A61M 16/202* (2014.02); *A61M 16/208* (2013.01); *A61M 2205/0205* (2013.01); *A61M 2205/0227* (2013.01); *A61M 2205/18* (2013.01); *A61M 2205/3368* (2013.01)

(56) References Cited

U.S. PATENT DOCUMENTS

| | | | |
|---|---|---|---|
| 2004/0123974 A1* | 7/2004 | Marler | A61M 16/1055 165/9.4 |
| 2005/0284175 A1* | 12/2005 | Kulcke | F24F 6/043 62/515 |
| 2006/0124127 A1* | 6/2006 | Du | A61M 16/085 128/201.13 |
| 2010/0083965 A1* | 4/2010 | Virr | A61M 16/1095 128/203.26 |
| 2010/0244289 A1 | 9/2010 | Roth | |
| 2012/0174922 A1* | 7/2012 | Virr | A62B 23/025 128/203.12 |
| 2016/0058968 A1* | 3/2016 | Yatsevich | A61M 16/0875 261/142 |
| 2017/0000968 A1* | 1/2017 | Harrington | A61M 16/16 |
| 2017/0007798 A1* | 1/2017 | Salmon | A61M 16/04 |
| 2017/0319811 A1* | 11/2017 | Foote | F24F 6/10 |
| 2018/0056024 A1* | 3/2018 | Harrington | A61M 16/109 |

FOREIGN PATENT DOCUMENTS

| | | | |
|---|---|---|---|
| WO | WO 2015/136489 | 9/2015 | |
| WO | WO 2016/036260 | 3/2016 | |
| WO | WO-2016036260 A1 * | 3/2016 | ........... A61M 39/24 |
| WO | WO 2016/139645 | 9/2016 | |
| WO | WO 2017/126982 | 7/2017 | |

* cited by examiner

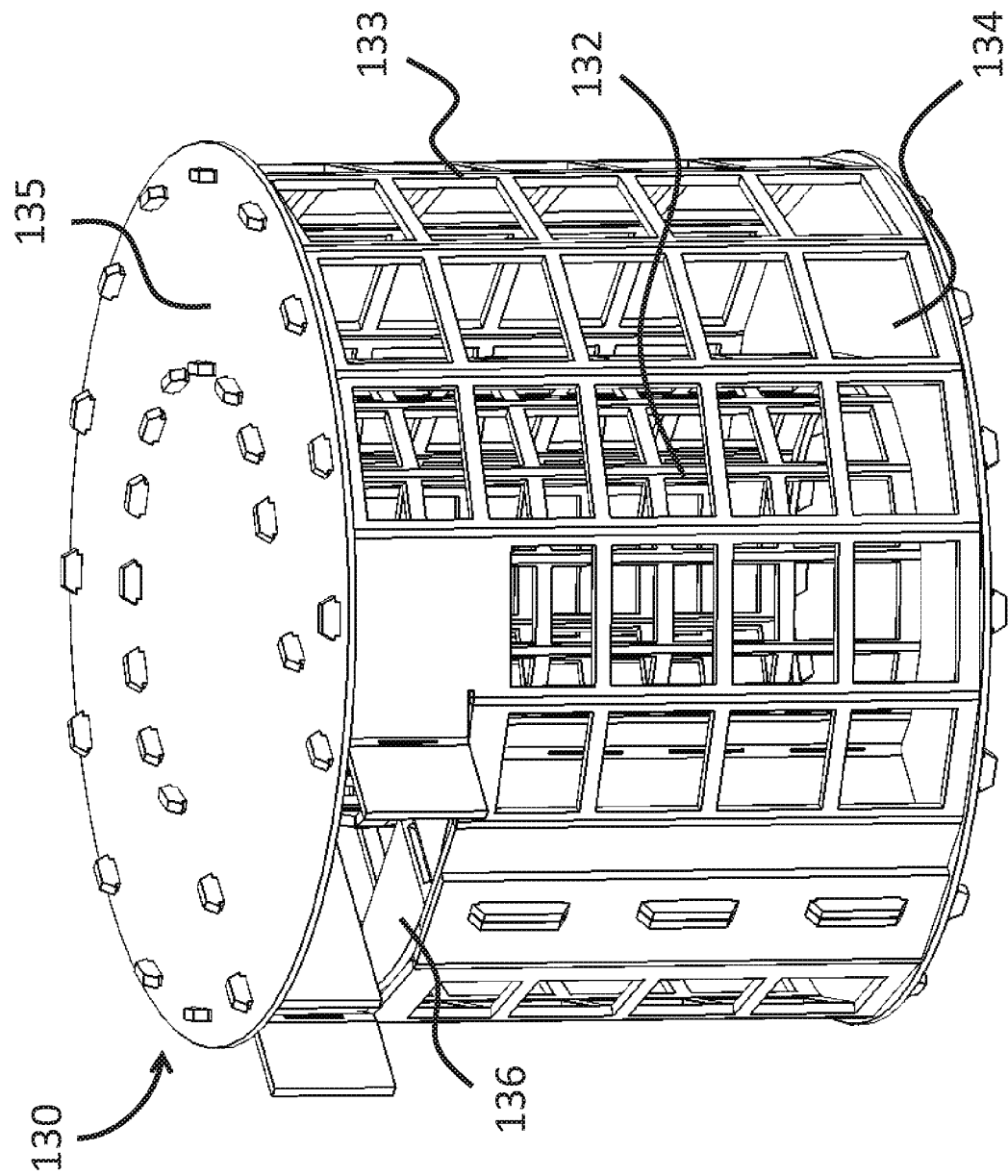

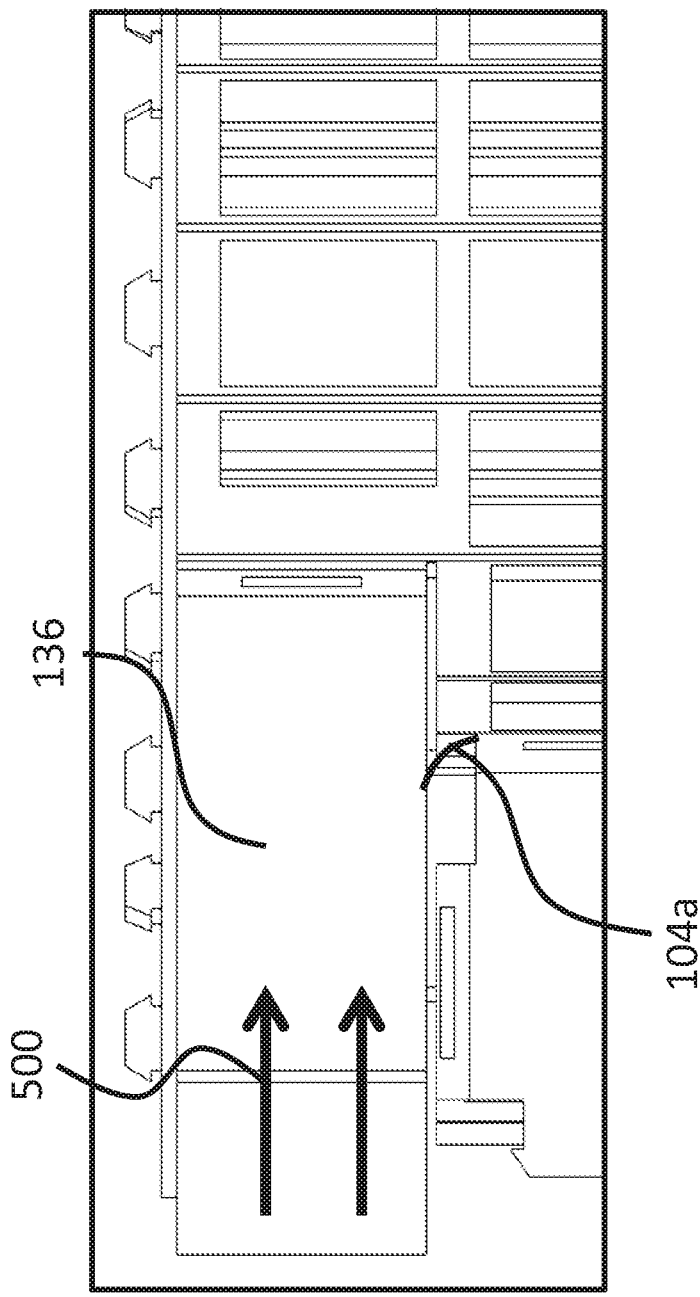

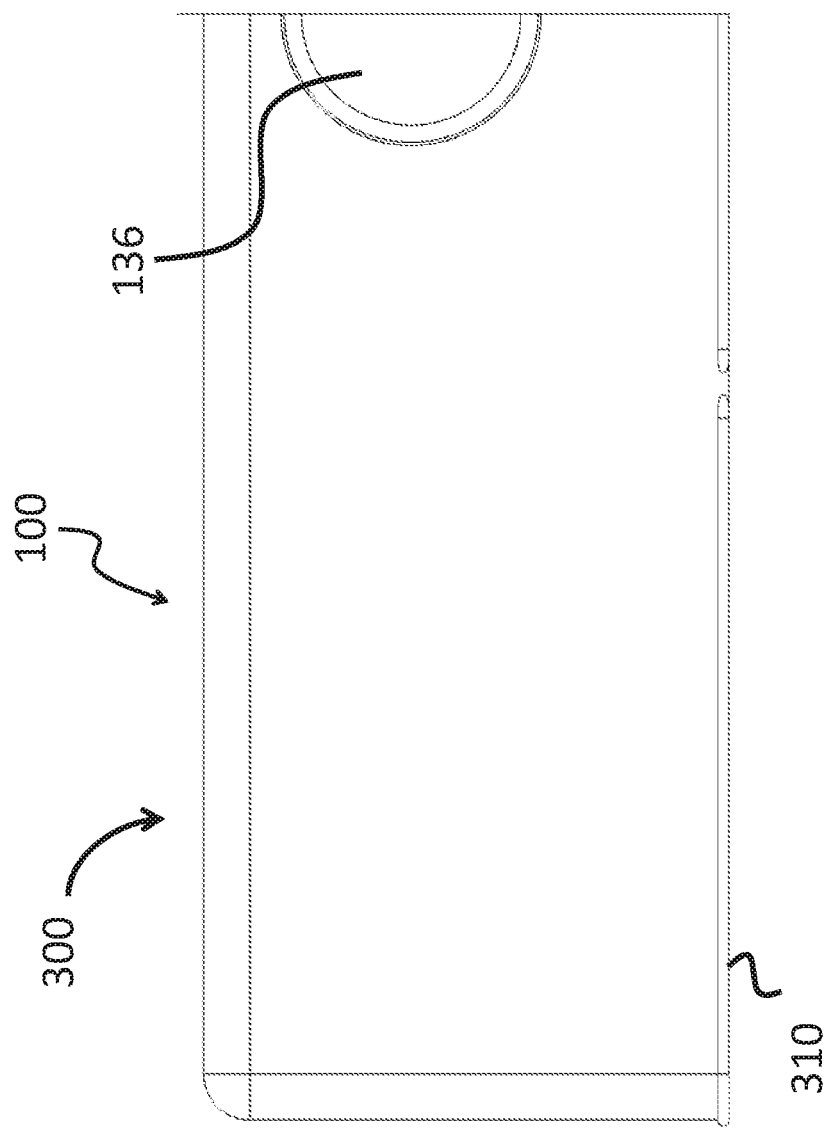

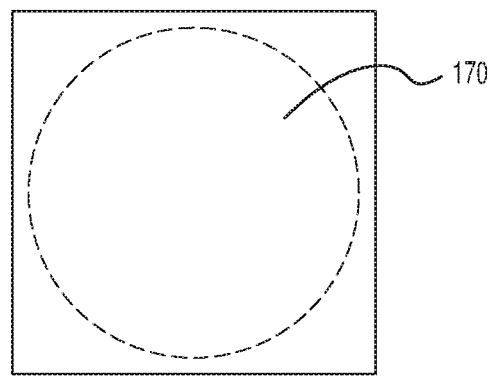
*Fig. 30A*
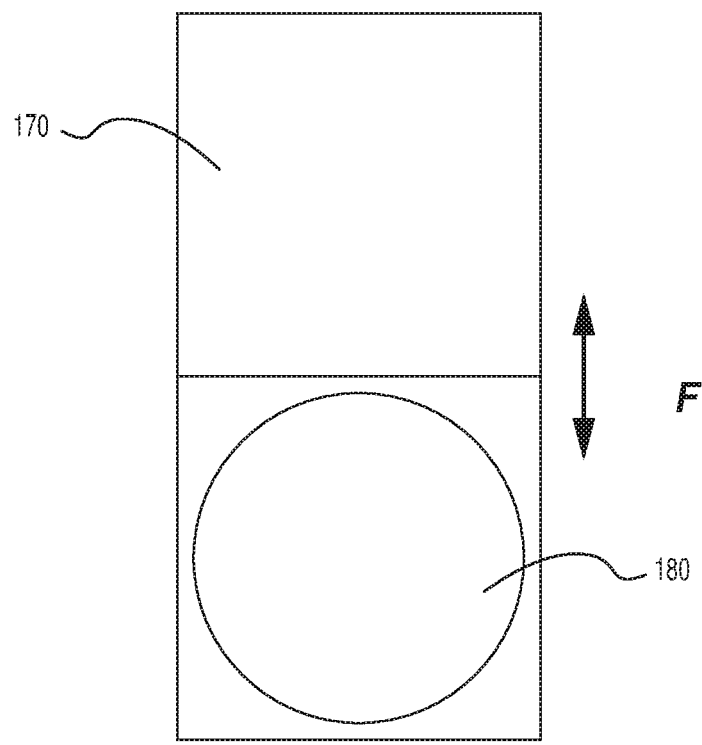
*Fig. 30B*
Figure 30

HUMIDIFICATION DEVICE AND SYSTEM

BACKGROUND

Technical Field

The present disclosure generally relates to a humidification device and humidification system for use in the delivery of respiratory therapy to a patient. More particularly, the present disclosure relates to a humidifier and humidification system comprising a non-heated wick for use in delivering pressurised, humidified breathing gas to a patient.

Description of the Related Art

Humidifiers are often used in respiratory therapy to provide humidified breathing gas to the airways of a person suffering from any of a number of respiratory illnesses or conditions. Such therapies may include but are not limited to pressure therapy, such as continuous positive airway pressure (CPAP) therapy and non-invasive ventilation (NIV) therapy.

CPAP therapy can be used to treat obstructive sleep apnoea (OSA), a condition in which a patient's airway intermittently collapses during sleep, preventing the patient from breathing for a period of time.

CPAP therapy involves the delivery of a supply of continuous positive air pressure to the airway of the patient via a respiratory interface. The continuous positive pressure acts as a splint within the patient's airway, which secures the airway in an open position such that the patient's breathing and sleep are not interrupted.

However, the breathing gas provided during pressure therapy can dry the airways of a patient, which leads to patient discomfort. Respiratory pressure therapy systems, such as CPAP systems and NIV systems, therefore typically include humidifiers in which a body of water is heated and air is passed over the water, where it is humidified before being delivered to a patient receiving respiratory pressure therapy. The most common method of heating the body of water is through the use of a thermally conductive heater plate that is heated by an electrically powered heating element. However, actively heating water using a heater plate has a number of disadvantages. For example, it may require a relatively large amount of power (approximately 85-100 W, or 40-60 W, depending on the device) to power a heating element to generate the necessary level of heat. Such a high power requirement increases the cost to operate the humidifier. The high power requirement can also limit the portability of the humidifier because the device must either be constantly connected to mains power, or if battery powered, requires a large (and typically expensive) battery to operate for an extended period of time.

Another disadvantage is that an active heating system, whether using a conductive method (such as by using a heater plate) or an inductive method, requires electronics to control and operate the heating system, which adds to the complexity of the humidifier; increases the cost to produce the humidifier; and also requires the size of the humidifier to be sufficiently large to include the heating system with control electronics in an appropriate arrangement within the humidifier. In addition, software is required to operate the electronic controls for the heating system, which further increases the complexity and cost of the humidifier.

Active heating systems also tend to have an inherent time delay between when the heating system is turned on and when the humidification system is operating at the set or desired level. For example, the heater plate must heat the entire body of water to an elevated temperature before a substantial increase in humidity results, which can take up to 30 minutes or more.

Another disadvantage with humidifiers that require a heating system for humidification is the associated hazard risk. For example, a heating element creates the opportunity for a heat or temperature hazard to be present to the user.

It is an object of the present invention to provide a humidification device or system that goes at least some way towards overcoming the disadvantages of known humidification devices or systems, or to at least provide the public with a useful alternative.

BRIEF SUMMARY

The systems and devices described herein have innovative aspects, no single one of which is indispensable or solely responsible for their desirable attributes. Without limiting the scope of the claims, some of the advantageous features will now be summarized.

In a first aspect, the invention provides a humidification device for use in CPAP, wherein the device comprises: a wick chamber for supporting a wick and comprising at least a gas inlet; a non-heated fluid chamber for holding fluid to be placed in contact with the wick; wherein the fluid chamber is configured to allow fluid from the fluid chamber to wet the wick to humidify gas passing through or over the wick.

In one form, the wick chamber is held within the fluid chamber and the wick chamber comprises a foraminous structure for holding the wick within the wick chamber and diffusing gas flow through or over the wick. Optionally, the wick chamber comprises a baffle wall comprising diffusion apertures of varying sizes to diffuse gas through or over the wick. In another form, the humidification device may comprise a blade diffuser to diffuse gas from the gas inlet through or over the wick.

In one form, the gas inlet is located on the side of the wick chamber to direct gas through the wick from the side of the wick. The gas inlet may enter the wick chamber at a transition region comprising a curved radius between the gas inlet and the chamber at a transition region comprising a curved radius between the gas inlet and an external wall of the wick chamber to encourage gas entering the wick chamber to diffuse by exploiting a Coanda effect.

In one form, the humidification device comprises a wick supported by the wick chamber. Different regions of the wick may have a different thickness to other regions.

In a second aspect, the invention provides a humidification device for use in CPAP, wherein the device comprises: a wick chamber for supporting a wick; a gas inlet to the wick chamber; and a diffusion system for directing or controlling gas flow through the device. Optionally, the diffusion system comprises a diffuser to diffuse gas flowing from the gas inlet and into the wick chamber substantially evenly through or over the wick. In one form, the gas inlet is located on the side of the wick chamber to direct gas through the wick from the side of the wick.

In one form, the wick chamber comprises a foraminous structure for supporting the wick within the wick chamber and diffusing gas flow through or over the wick. Preferably, the wick chamber comprises a baffle wall comprising diffusion apertures of varying sizes to diffuse gas flow through or over the wick.

In one form, the gas inlet enters the wick chamber at a transition region comprising a curved radius between the gas inlet and an external wall of the wick chamber to encourage gas entering the wick chamber to diffuse by exploiting a Coanda effect. Optionally, the humidification device comprises a blade diffuser to diffuse gas from the gas inlet through the wick.

In one form, the humidification device comprises a wick supported by the wick chamber. Different regions of the wick may have a different thickness to other regions.

In a third aspect, the invention provides a humidification module configured for retrofit insertion into a humidification device, wherein the humidification module comprises a wick chamber for supporting a wick within the wick chamber, and wherein the humidification module comprises at least one attachment member to detachably attach the humidification module to a flow generator to generate a flow of gas through the humidification module.

In a fourth aspect, the invention provides a humidification control system comprising: a humidification device comprising a gas inlet and a gas outlet, a wick chamber for supporting a wick, the wick chamber being in fluid communication with the gas inlet and the gas outlet and being configured to provide humidified gas to the gas outlet of the humidification device, a gas bypass connected to the gas inlet and the gas outlet and configured to allow gas to bypass the wick chamber from the gas inlet to the gas outlet, and a controller to control the amount of gas that bypasses the wick chamber. Preferably, the humidification control system further comprises a wick supported by the wick chamber.

In a fifth aspect, the invention provides a humidification device for use in CPAP, wherein the device comprises: a wick chamber for supporting a wick; a fluid chamber to hold a reservoir of fluid; and a fluid flow path connecting the wick chamber and the fluid chamber to allow fluid to be fed from the fluid chamber to the wick chamber to wet the wick.

In one form, the wick chamber and the fluid chamber each comprise an opening and wherein the device further comprises a removable seal configured to detachably attach to the wick chamber, the fluid chamber, or both, to seal the openings of the wick chamber, the fluid chamber, or both. Preferably, the humidification device further comprises a wick supported by the wick chamber.

In a sixth aspect, the invention provides a humidification device for humidifying a flow of breathing gas, wherein the humidification device comprises: a fluid chamber having a gas inlet and a gas outlet, wherein the breathing gas flows through the fluid chamber from the gas inlet to the gas outlet, a wick supported within the fluid chamber such that the flow of breathing gas through the fluid chamber passes through the wick, the wick configured to wick fluid within the fluid chamber across the wick, wherein the wick comprises: a wick body, and a hollow region, wherein the hollow region of the wick is downstream of the gas inlet, and wherein the gas outlet is downstream of the hollow region of the wick. Optionally, the wick includes a wick inlet downstream of the gas inlet and upstream of the hollow region.

In one form, a wick chamber is located within the fluid chamber and comprises a foraminous structure for supporting the wick within the fluid chamber. Preferably, the wick chamber is configured to attach to the fluid chamber. In one form, the wick chamber includes an internal chamber wall, an external chamber wall, a base and a lid. The wick is optionally supported between the internal chamber wall and the external chamber wall.

In one form, the hollow region of the wick is a cuboid shape. In another form, the hollow region of the wick is a cylindrical shape.

In one form, a first thickness of the wick near the gas inlet is thinner than a second thickness of the wick near the gas outlet.

Preferably, in use, fluid within the fluid chamber is maintained at or below ambient temperature.

In a seventh aspect, the invention provides a kit comprising: a flow generator comprising a non-humidified gas circuit to deliver non-humidified gas to a patient; a humidification module detachably attachable to the flow generator and comprising a humidified gas circuit to deliver humidified gas to a patient; and a control system to control the amount of gas that flows from the flow generator through the humidified gas circuit and the amount of gas that flows from the flow generator through the non-humidified gas circuit.

In an eighth aspect, the invention provides a humidification device for use in CPAP, wherein the device comprises: a wick chamber for supporting a wick and comprising at least one gas inlet; a fluid chamber for holding fluid to be placed in contact with the wick; wherein the fluid chamber is configured to allow fluid from the fluid chamber to wet the wick; and a flow generator configured to cause a flow of gas to pass through or over the wick to produce a flow of humidified gas, wherein the flow of humidified gas is at a temperature equal to ambient temperature plus any temperature increase due to heating caused by the flow generator.

In a ninth aspect, the invention provides a humidification device for a respiratory pressure therapy device comprising: a fluid chamber comprising a gas inlet and a gas outlet; and a wick supported within the fluid chamber, the wick comprising a wick body having two spaced apart opposed portions, wherein the wick is at least partially disposed between the gas inlet and the gas outlet of the fluid chamber.

In one form, the wick is disposed within the fluid chamber to cause gas that enters the fluid chamber via the gas inlet to pass through or over a first of the spaced apart portions of the wick body, across the space between the two portions and then through or over a second of the spaced apart portions of the wick body before exiting the fluid chamber via the gas outlet. Preferably, the wick body comprises a hollow region that defines the space between the two opposed portions of the wick body. Optionally, the wick body comprises a curved external surface. In one form, the wick body comprises a curved external surface and wherein the hollow region of the wick body is defined by a curved internal wall to form an annular wick.

In one form, the wick body comprises a first linear portion. The wick body may also comprise a second linear portion. Optionally, the first linear portion is disposed at an angle to the second linear portion. In one form, the angle is greater than 90 degrees.

In one form the wick body comprises wicking elements. Optionally, the wick body comprises a lattice of wicking elements. Preferably, the wicking elements are fibrous.

Also disclosed herein is a humidification device for use in CPAP, wherein the device comprises: a wick; a non-heated fluid chamber for holding fluid in contact with the wick; and a gas inlet to the fluid chamber, wherein the fluid chamber and wick are configured to humidify gas passing through the wick.

Preferably, gas passes through the wick at approximately ambient conditions.

In one form, the fluid chamber comprises a connection structure for directly connecting to a self-supporting wick. Optionally, the self-supporting wick is a sufficiently rigid sintered wick. The self-supporting wick may be directly connected to fluid within the fluid chamber.

Preferably, the fluid chamber comprises a foraminous structure for holding the wick within the fluid chamber and diffusing gas flow through or over the wick.

In one form, the humidification device further comprises a wick chamber for supporting the wick within the fluid chamber, wherein the wick chamber comprises a baffle wall comprising diffusion apertures of varying sizes to diffuse gas flow through or over the wick.

Preferably, the gas inlet is located to direct gas through the wick from the side of the wick.

Optionally, the gas inlet is relatively large compared to the side of the wick. For example, the gas inlet may comprise an opening to the wick that is at least one third of the size of the side surface of the wick.

In one form, a plenum is located between the gas inlet and the wick.

Optionally, the gas inlet enters the fluid chamber at a transition region comprising a curved radius between the gas inlet and fluid chamber wall to encourage gas entering the fluid chamber to diffuse by exploiting a Coanda effect.

In one form, the humidification device further comprises a blade diffuser to diffuse gas from the gas inlet through the wick.

Optionally, different areas of the wick have a different thickness.

Also disclosed herein is a humidification device for use in CPAP, wherein the device comprises: a wick; a wick chamber for supporting the wick; a gas inlet to the wick chamber; and a diffusion system for directing or controlling gas flow through the device.

Preferably, the diffusion system comprises a diffuser for diffusing gas flowing from the gas inlet and into the wick chamber substantially evenly through the wick.

Preferably, the wick chamber comprises a foraminous structure for holding the wick within the wick chamber and diffusing gas flow through or over the wick.

Optionally, the wick chamber comprises a baffle wall comprising diffusion apertures of varying sizes to diffuse gas flow through or over the wick.

In one form, the gas inlet is located to direct gas through the wick from the side of the wick.

Optionally, the gas inlet is relatively large compared to the side of the wick. For example, the gas inlet may comprise an opening to the wick that is at least one third of the size of the side surface of the wick.

In one form, the humidification device further comprises a plenum located between the gas inlet and the wick.

In one form, the gas inlet enters the wick chamber at a transition region comprising a curved radius between the gas inlet and chamber wall to encourage gas entering the wick chamber to diffuse by exploiting a Coanda effect.

Optionally, the humidification device further comprises a blade diffuser to diffuse gas from the gas inlet through the wick.

In one form, different areas of the wick have a different thickness.

Further disclosed herein is a humidification control system comprising: a humidification device comprising a gas inlet and a gas outlet, a wick humidifier connected to the gas inlet and the gas outlet and configured to deliver humidified gas to the gas outlet of the humidification device, a gas bypass connected to the gas inlet and the gas outlet and configured to allow gas to bypass the wick humidifier from the gas inlet to the gas outlet, and a controller to control the amount of gas that bypasses the wick humidifier.

Optionally, the controller is connected to the gas inlet.

Also disclosed herein is a humidification device for use in CPAP, wherein the device comprises a wick; a wick chamber to hold the wick; a fluid chamber to hold a reservoir of fluid; and a fluid flow path connecting the wick chamber and the fluid chamber to allow fluid to be fed from the fluid chamber to the wick chamber to wet the wick.

Optionally, the device is configured to allow fluid to flow from the fluid chamber to the wick chamber to maintain a substantially constant water level in the wick chamber.

Preferably, the device is portable.

Preferably, the fluid is water.

In one form, the wick chamber and the fluid chamber each comprise an opening and the device further comprises a removable seal configured to detachably attach to the wick chamber and the fluid chamber to seal the openings of the wick chamber and the fluid chamber.

The wick chamber opening may be configured to allow a wick to be placed into and removed from the wick chamber.

The fluid chamber opening may be configured to allow fluid to be poured into and out of the fluid chamber.

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made.

Terms such as "top", "bottom", "upper", "lower", "front", "back", "left", "right", "rear", and "side" describe the orientation and/or location of portions of the components or elements within a consistent but arbitrary frame of reference which is made clear by reference to the text and the associated drawings describing the components or elements under discussion. Moreover, terms such as "first", "second", "third", and so on may be used to describe separate components. Such terminology may include the words specifically mentioned above, derivatives thereof, and words of similar import.

BRIEF DESCRIPTION OF THE DRAWINGS

FIG. 6A is a perspective view of one form of wick chamber;

FIG. 14A is a cross-sectional side view of a portion of a wick chamber, showing the wick chamber inlet and comprising a curved radius at a transition region of the inlet to exploit a Coanda effect in gas flowing through the inlet and to thereby encourage more even distribution of gas flow through and over the wick;

FIG. 18A is a partial front view of the housing of the humidification device of FIG. 16A;

FIG. 30A is a schematic view of a gate valve in a lowered, closed position, covering a gas channel inlet;

FIG. 30B is a schematic view of a gate valve in a raised, open position, exposing a gas channel inlet;

DETAILED DESCRIPTION

Figure 1A:
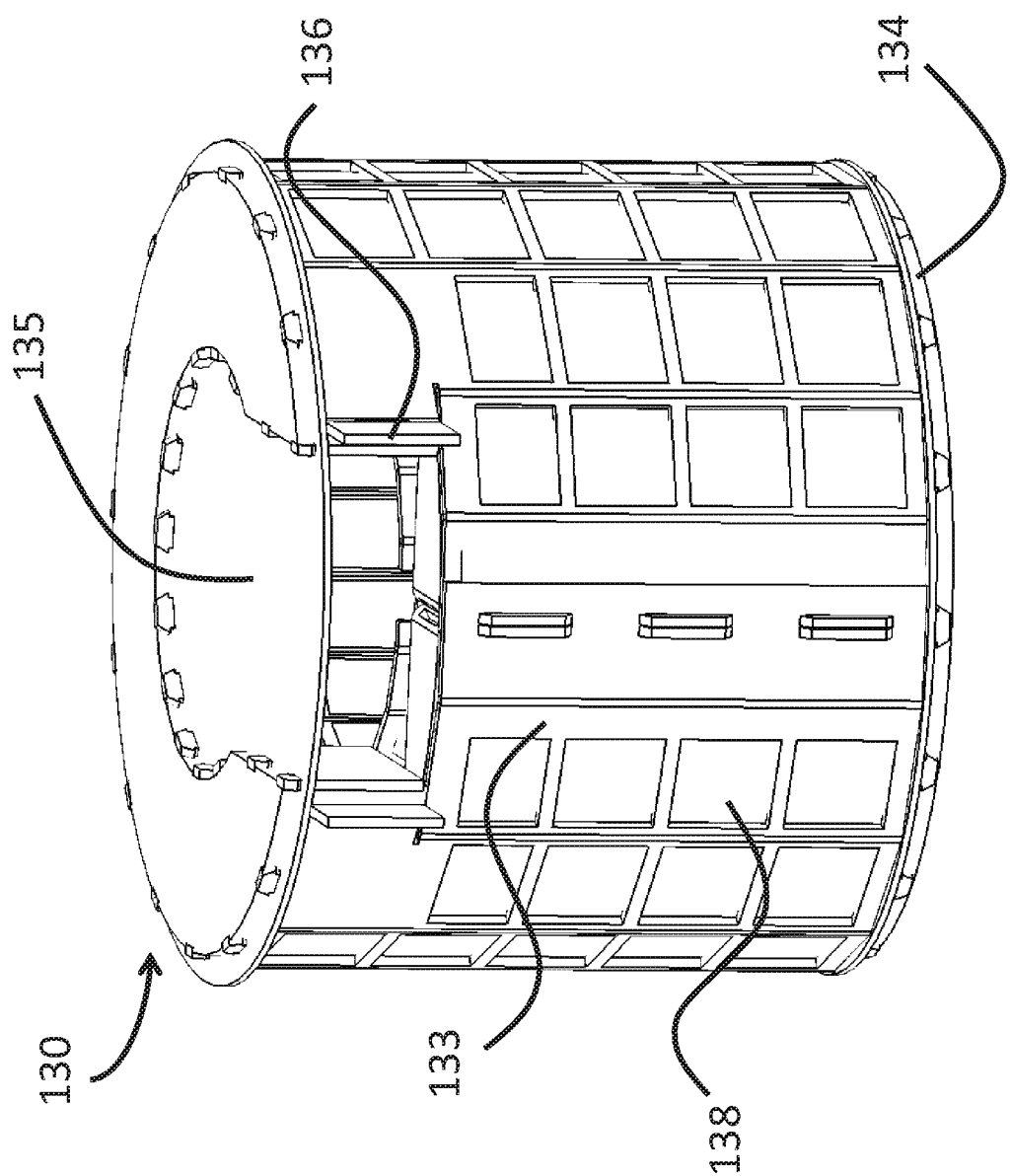
FIGS. 1A and 1B are each perspective views of different forms of wicking structure of a wick for a humidification device.
Figure 1B:
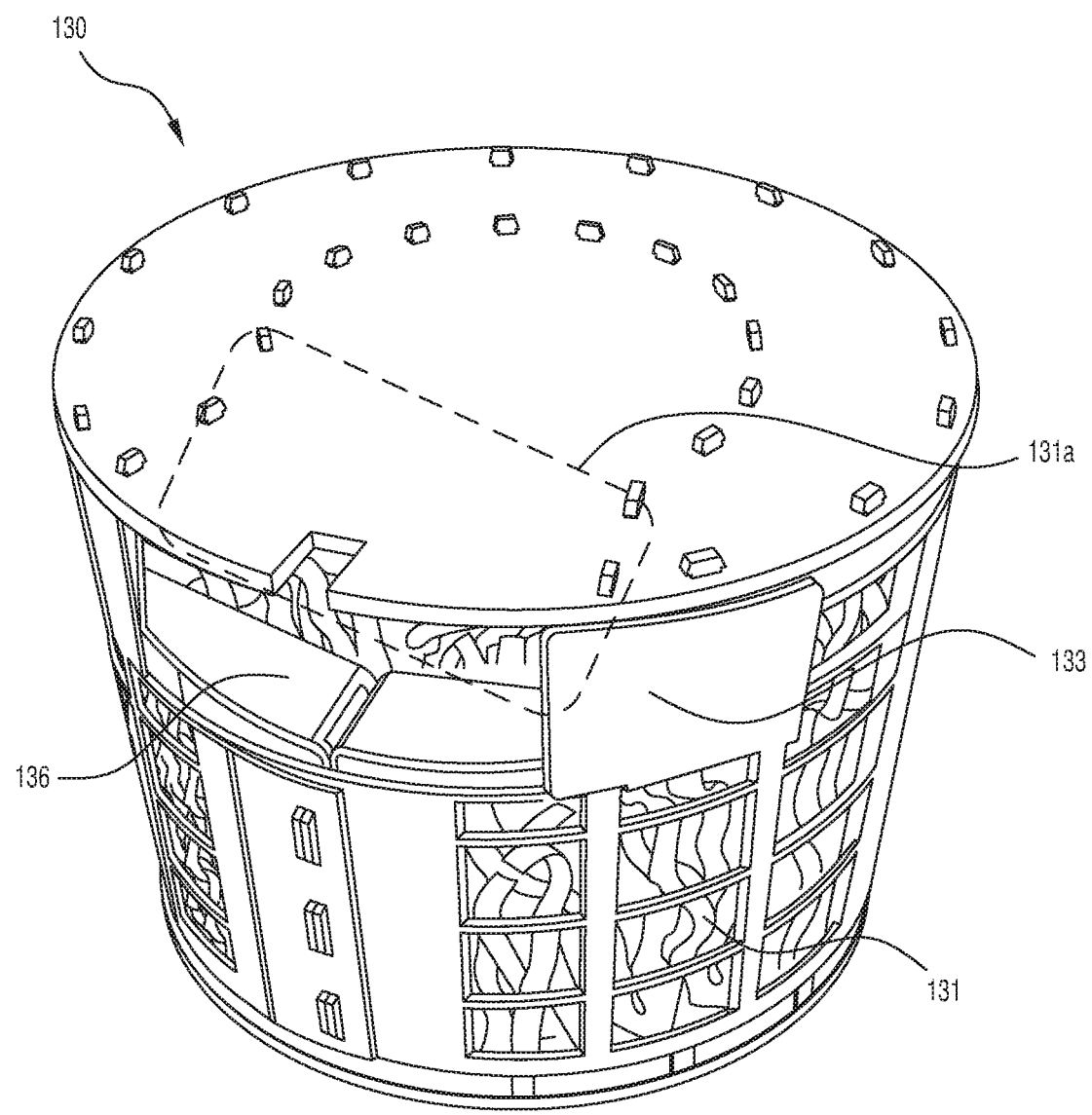

Referring to FIGS. 1A to 35D, the invention relates to a humidification device 100 and a humidification system 200 for the delivery of humidified breathing gas, such as air, to a patient. The humidification device or system comprises a humidifier. The humidification system may comprise an in-built humidifier or a detachable humidifier.

In one form, the humidification device and system may be configured for use in CPAP or other positive pressure respiratory therapy, such as NIV.

The humidification device 100 may comprise a heating system to heat fluid within a fluid chamber. In another form, the humidification device may be devoid of such a heating system and may operate at approximately ambient temperature, which may include a temperature slightly lower than or slightly above ambient temperature. In other words, the humidification device may be a non-heated humidification device that humidifies gas passing through or over a wick at approximately ambient conditions. For example, the humidification device may provide passive, non-active humidification through an absence of an intentional form of heating or through an absence of a controlled heating system to heat fluid in a fluid reservoir within the device. Optionally, the humidification device is configured to humidify breathing gas without the assistance of a designated electric heating system to heat fluid in the fluid reservoir. Where the device includes an electronic control system, such as a system for operating the flow generator, heat from the energy created by the control system may raise the temperature of the fluid in the fluid reservoir or gas within the device, but only slightly above ambient temperature.

The humidification device 100 may comprise a flow generator/blower 110, or may be configured to attach to a flow generator 110, to blow breathing gas 500 through the device 100 in order to humidify the breathing gas 500 before delivering the breathing gas to a patient. The flow generator 110 may add some heat to the gas entering the humidification device, causing the temperature of the gas to be raised slightly above ambient temperature. This slightly heated gas may cause some marginal increase of temperature to the fluid in the fluid reservoir.

The humidification device 100 may comprise a wick 131 and a fluid chamber 120 for holding fluid 121 that may be at least partially absorbed by the wick 131. In one form, the wick 131 may be held within the fluid chamber 120, as shown best in FIGS. 1A to 15, so that fluid within the fluid chamber 120 wets the wick 131 within the chamber 120. In another form, as shown best in FIGS. 16A to 23, the wick 131 may be held in or supported by a wick chamber/wick support structure 130 that is in fluid communication with the fluid chamber 120 so that fluid 121 from the fluid chamber 120 flows to the wick chamber 120 and wets the wick 131 in the wick chamber 130. In one form, the wick chamber 130 may be attached to the fluid chamber 120.

The wick 131 may comprise a structure that aids wetting by the fluid 121 and/or that aids gas flow 500 through or over the wick. The wick 131 may be wet by at least partially absorbing or soaking up the fluid 121 and/or by being at least partially coated by the fluid 121.

In one form, the wick structure may comprise a matrix or lattice of wicking elements, which makes it easier to cause a portion of the gas flow 500 to flow through or over the wick 131 and a portion of the gas 500 to flow across the wicking elements of the wick to evaporate fluid 121 from the wick 131. The wicking elements may be small fibrous constituents of the wick 131 so that fluid 121 from the fluid chamber 120 is encouraged to spread across the wicking elements. The wicking elements may be arranged to provide apertures between at least some of the wicking elements to allow gas flow between wicking elements. The wick 131 may comprise a large number of wicking elements to create a large surface area for gas 500 to pass across the wick 131 and to therefore improve the rate at which fluid evaporates from the wick 131 and humidifies the gas 500. The term 'across the wick' as used in this specification includes gas flow through the wick and over the wick, unless otherwise indicated.

The fluid 121 may be water, an alternative fluid (such as a medicinal fluid), or a combination of water and an alternative fluid.

The humidification device 100 comprises a gas inlet 104 that directs gas 500 across the wick 131.

The wick 131 is configured to draw fluid, from the fluid chamber 120, up and through the body of the wick 131 via capillary action so that the wick is kept moist. The wick 131 acts to increase the humidity of breathing gas 500 passing across the wick 131. In some cases, the use of a wick 131 can increase the relative humidity of airflow through the humidification device to 100%.

The wick 131 may be shaped and dimensioned to provide a relatively large surface area over which the fluid 121 can be dispersed in order to increase the humidifying efficiency of the wick 131. The wick 131 may have a substantially uniform structure or an irregular structure.

In one form, the wick comprises a wick body comprising two spaced apart portions. In one form, the wick body may comprise a hollow region that defines the space between the first and second portions of the wick body.

The wick body may be of any suitable shape. For example, the wick body may comprise a curved external surface or a linear external surface. In one form, the wick body may comprise two or more linear external surfaces forming linear portions of the wick body that are disposed at an angle to each other, such as at an angle of about or greater than 90°. In one form, first and second linear surfaces meet at an angle of about or greater than 90°. The hollow region may be defined by an internal surface comprising a curved wall, or one or more linear walls joined together, or a combination of curved and linear walls. Where the wick body comprises two spaced apart opposed portions, each having a linear internal surface (such as a wick body having a box-section shape), the two portions may be referred to as first and second linear portions. The first and second linear portions may be joined together by side portions, which may also be linear, but may otherwise be curved. In one form, the first and second linear portions may be disposed at an angle to each other of about or greater than 90°. In one form, the first and second linear portions are joined together at an angle of about or greater than 90°.

Figure 2A:
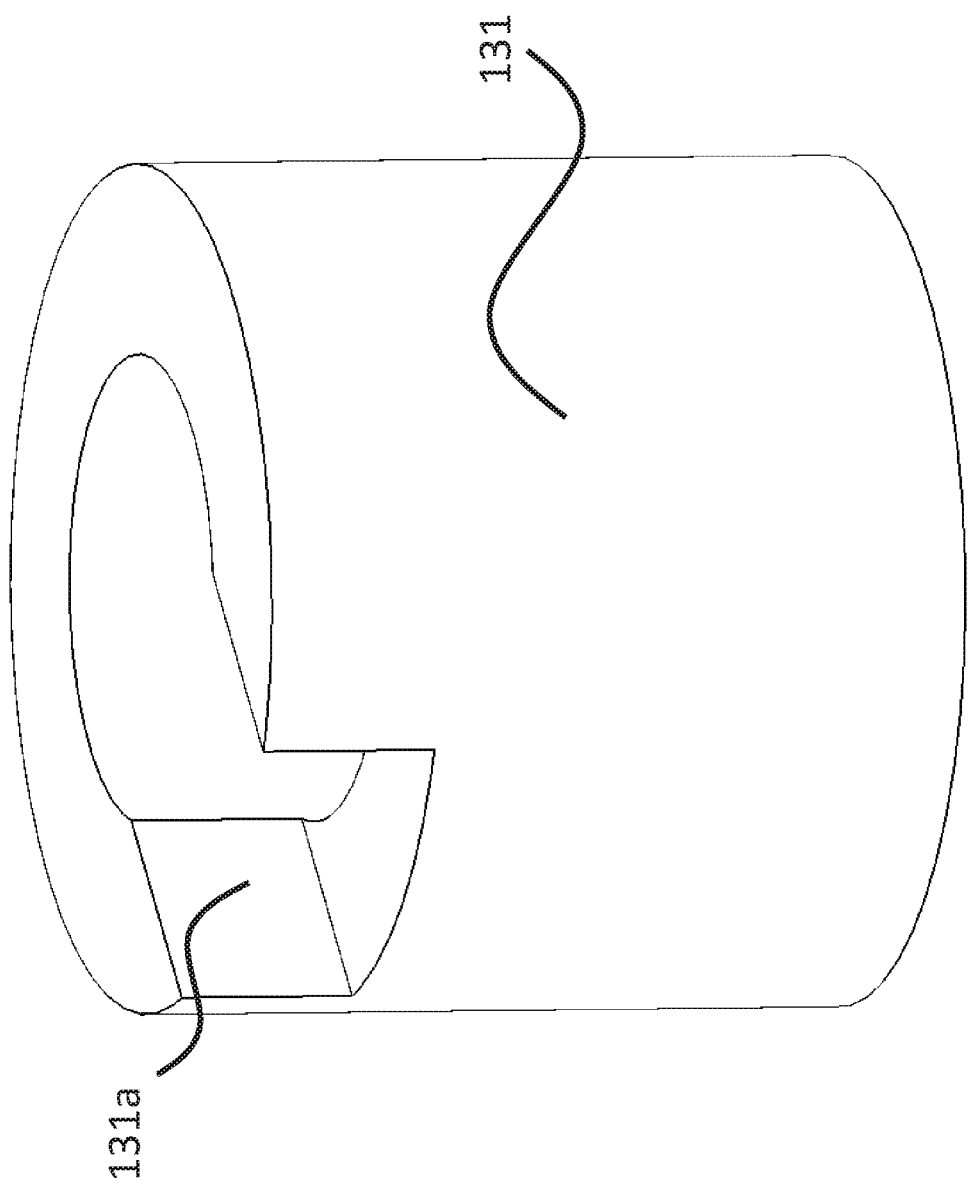
FIG. 2A is a schematic perspective view of one form of wick that may be used with a humidification device.
Figure 2B:
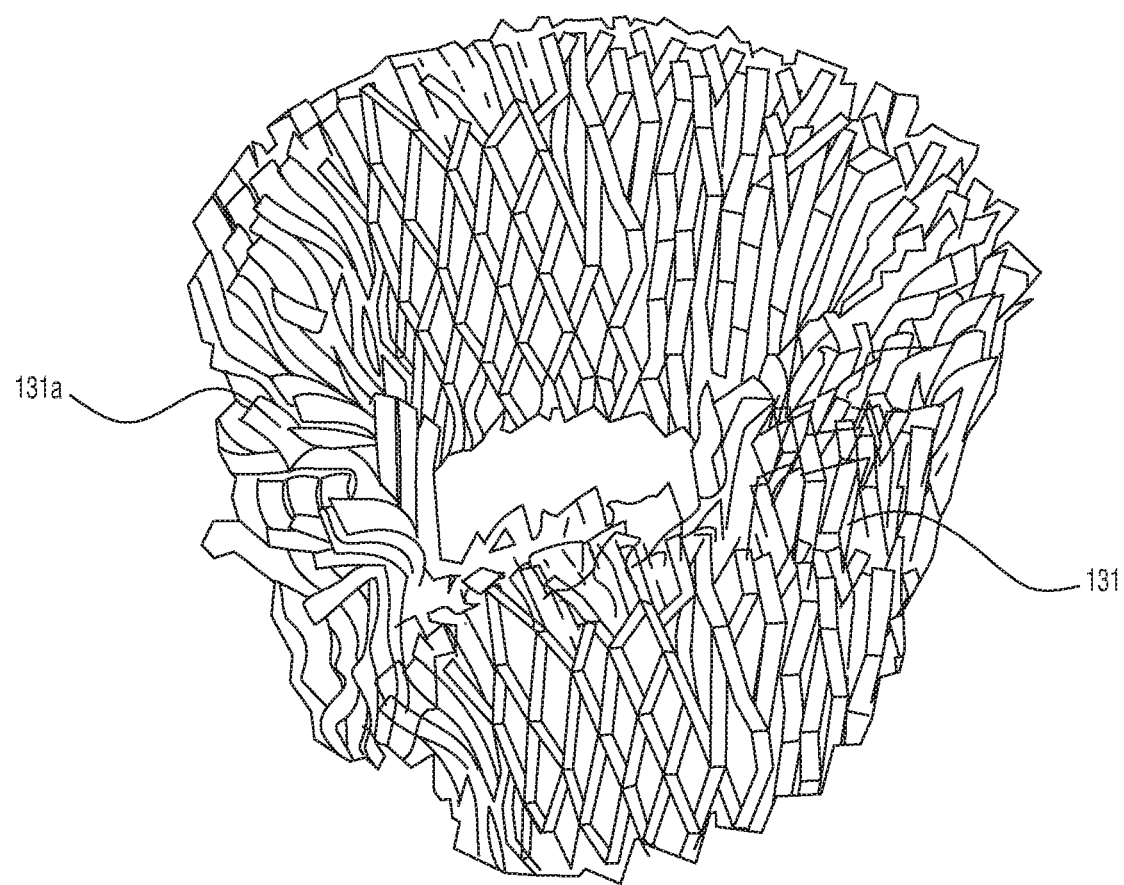
FIG. 2B is a perspective view of a tubular wick that may be used with a humidification device.
Figure 2C:
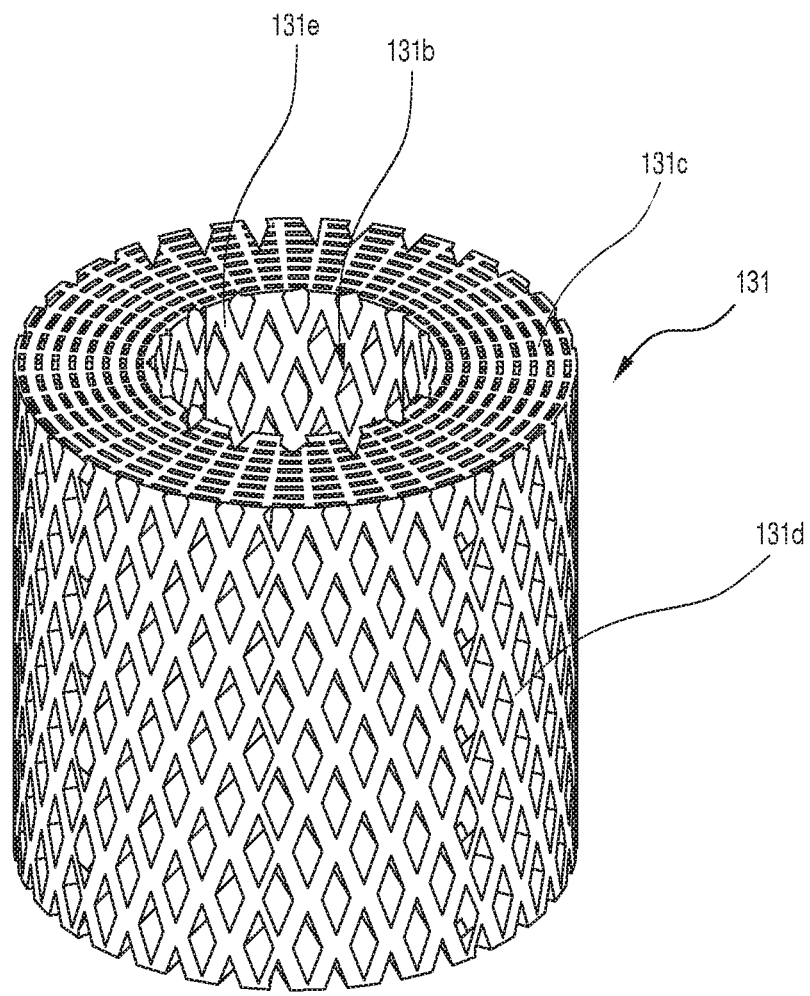
FIG. 2C is a perspective view of another form of tubular wick that may be used with a humidification device, this wick having a greater thickness between the internal surface defining the hollow region of the wick and the external surface of the wick.
Figure 2D:
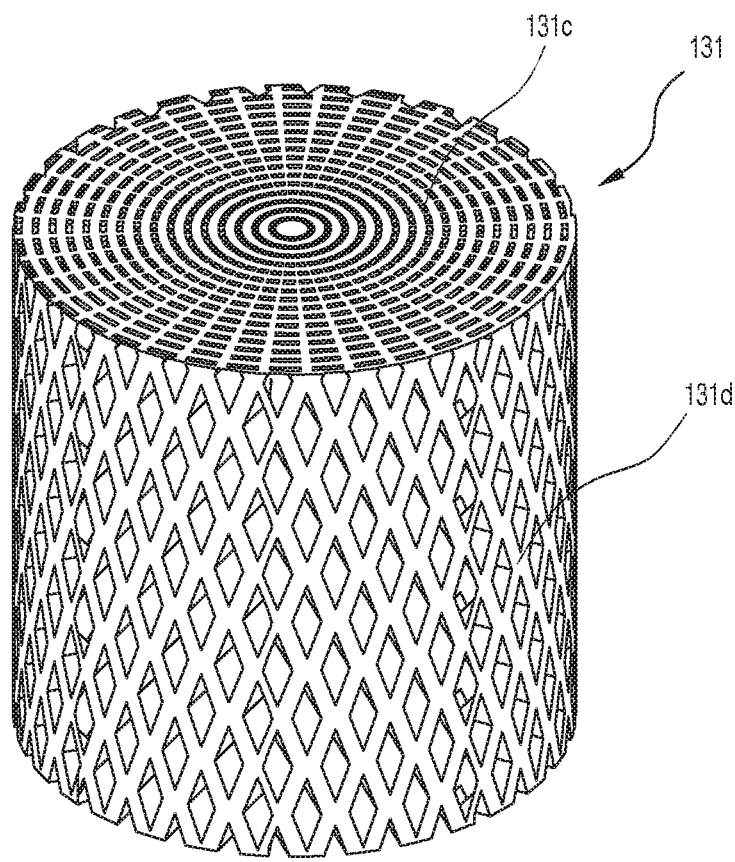
FIG. 2D is a perspective view of a cylindrical shaped wick having comprising a uniform structure that may be used with a humidification device.
Figure 2E:
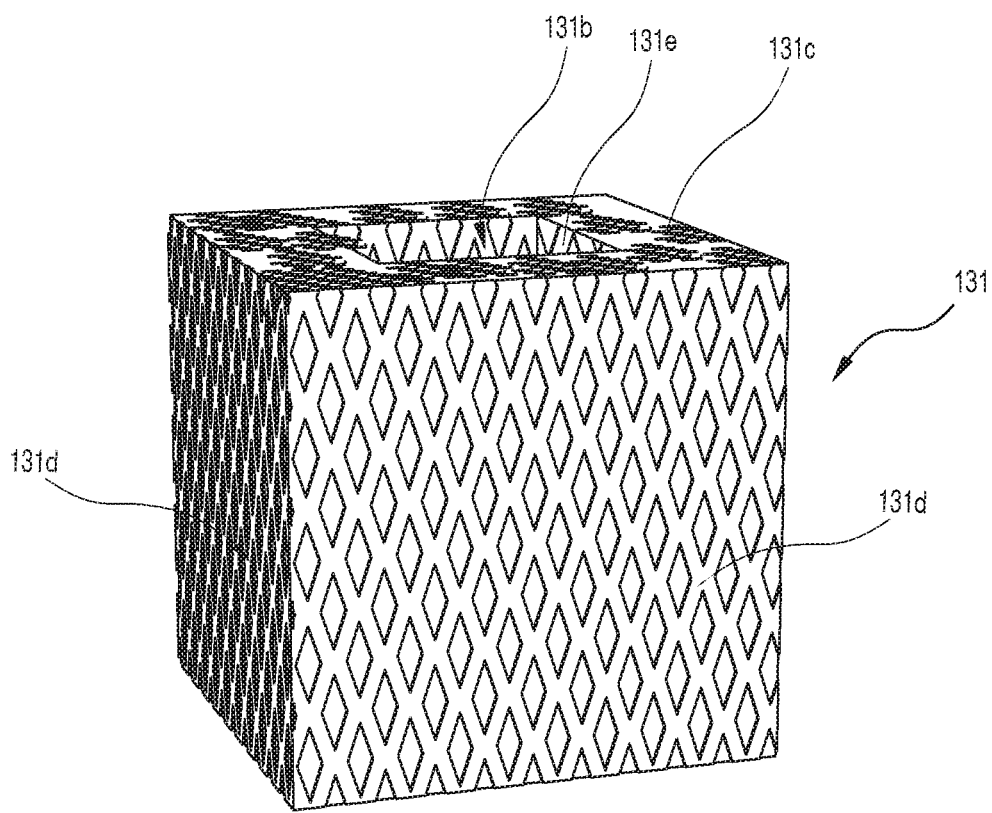
FIG. 2E is a perspective view of a polygonal shaped wick comprising a hollow region that may be used with a humidification device.
Figure 2F:
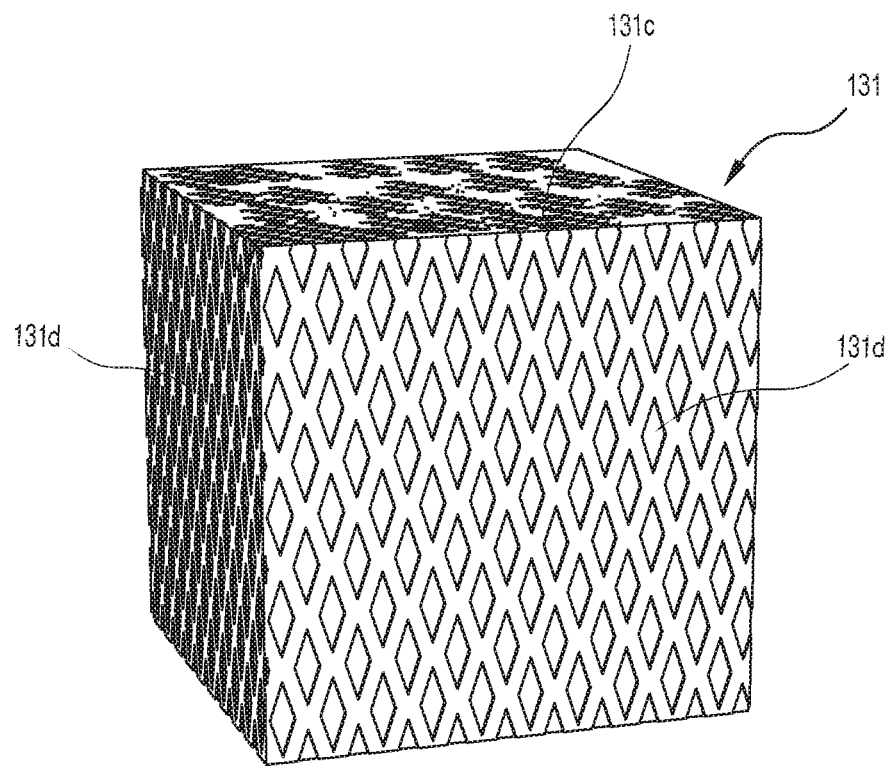
FIG. 2F is a perspective view of a polygonal shaped wick comprising a uniform structure that may be used with a humidification device.

In one form, as shown in FIGS. 2A to 2C, the wick 131 takes the shape of a hollow, tubular cylinder or annular shape. In another form, the wick may comprise any suitable curved shape, such as a U-shape. In yet another form, as shown in FIG. 2E, the wick 131 may take the shape of a hollow polygon or rectangular prism having multiple linear external surfaces that meet together at an angle of about 90°. In other configurations, the wick 131 could take the general shape of a hollow oval, or any other polygon and/or regular or irregular three-dimensional configuration. The hollow region of the wick is defined by one or more interior walls that form an interior surface of the hollow region. The shape of the hollow region may be the same as or different from the external shape of the wick. For example, the wick may comprise a cuboid external shape with a cuboid hollow region defined by four evenly sized internal walls. Alternatively, the wick may comprise a cuboid external shape with a tubular hollow region formed by a single curved internal wall. In alternate configurations, the wick 131 could simply be a planar two-dimensional face with a depth that forms a sheet of material, having a desired thickness.

In one form, as shown in FIGS. 2A to 2C and 2E, the wick may comprise at least one internal space 131*b*, such as a substantially hollow region or core. For example, the wick 131 may be substantially cylindrical or polygonal, such as cuboid, and may comprise a space or hollow region 131*b* within the wick, preferably at the centre of the wick 131. In another form, the hollow region 131*b* may be offset from centre, or the wick may comprise multiple hollow regions that may be evenly or unevenly spaced through the body of the wick. The hollow region(s) 131*b* may extend completely through the wick 131 from the top of the wick to the bottom. Or one or more hollow regions 131*b* may form a depression or recess in the top of the wick 131 so that the bottom of the wick comprises a substantially continuous surface. The internal space(s) 131*b* further increase the exposed surface area of the wick 131 and help to increase the rate of evaporation of fluid from the wick to increase the rate at which gas 500 is humidified by the humidification device 100. In another form, as shown in FIGS. 2D and 2E, the wick 131 may comprise a substantially consistent or uniform structure throughout the wick.

Optionally, the wick 131 comprises at least one opening or recess forming a wick inlet/wick opening portion 131*a* through which gas may be directed across the wick 131. Gas can be directed into the internal space(s) 131*b* via the wick opening 131*a* prior to being directed through the wick 131 to increase the surface area of the wick 131 that is exposed to the gas. The wick opening is greater than the pore size of the material from which the wick is made and is distinct from apertures created by the structural arrangement of the wick, such as apertures formed between wicking elements of a wick having a lattice structure.

The humidification device 100 also comprises a gas outlet through which the humidified gas 500 can be provided to a patient.

The humidification device 100 may operate as follows:

Firstly, ambient air/breathing gas 500 is drawn into the device 100 via an inlet.

Secondly, the ambient gas 500 passes through the powered flow generator 110. The gas may be caused to heat slightly (by only a few degrees Celsius) due to heat transfer from the energy released from the powered flow generator 110 and energy from other forces within the device, such as friction, compression, and the like.

Thirdly, the flow generator 110 blows the gas 500 across the wick 131, such as by blowing the gas through and over the wicking elements. Fluid 121 in and on the wick 131, particularly fluid on the wicking elements, is evaporated, which increases the humidity of the gas 500. At the same time, the evaporation of the fluid causes the temperature of the gas to be reduced slightly (i.e. due to the latent heat of vaporisation). The temperature decrease is typically only slight (a few degrees Celsius). The energy contained in the gas and provided incidentally by forces around the flow generator and the heating effect of electronics in the device, helps to maintain the temperature of the fluid reservoir 123 to approximately ambient temperature, preventing fluid 121 from within the fluid reservoir 123 from continuously cooling due to the loss of energy/heat as a result of evaporation.

Fourthly, the gas 500 is delivered to the patient via the gas outlet.

The humidification device 100 is therefore able to humidify ambient gas 500 passing through the device 100 without deliberately heating the gas 500 and therefore without including components in the device 100 (such as a heater) for the purpose of heating the gas 500 passing through the device 100.

In one form, as shown in FIGS. 1A to 15, the humidification device 100 comprises a fluid chamber 120 that includes a gas inlet 104, a gas outlet 105, a suspension bracket/fluid reservoir support structure/lid 126, and a tub/bucket/fluid reservoir 123 for holding a reservoir of fluid 121 and that attaches to the lid 126. The humidification device also comprises a wick 131 held within or supported by a wick chamber 130.

Figure 3A:
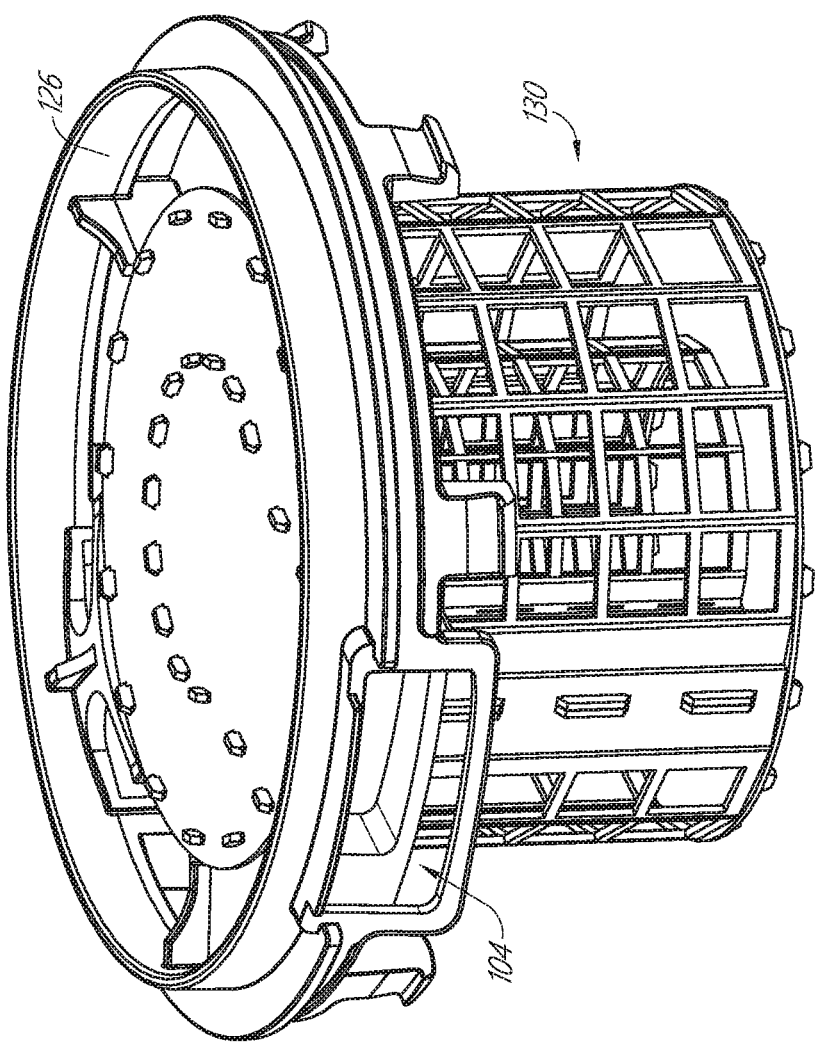
FIG. 3A is a perspective view of one form of fluid chamber support structure and wick chamber.
Figure 3B:
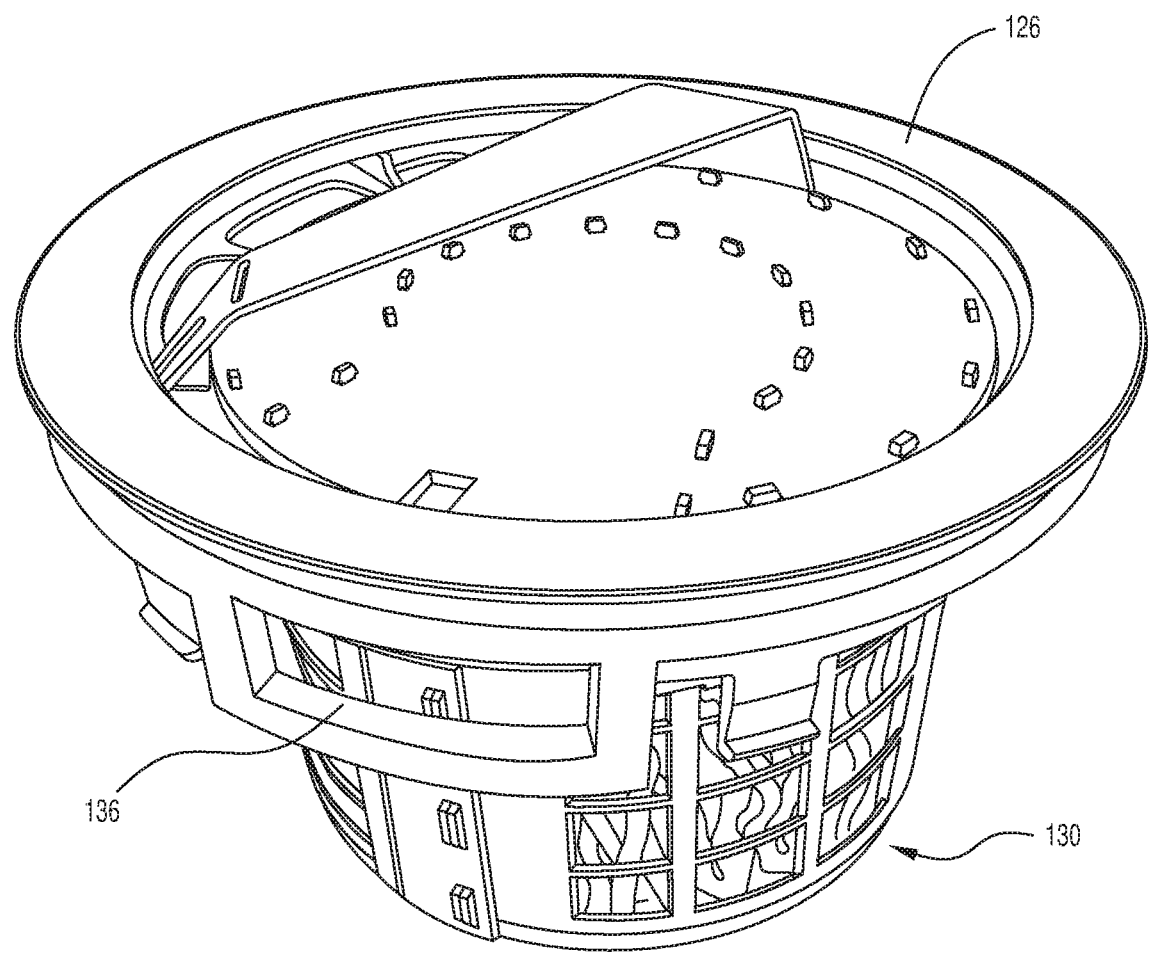
FIG. 3B is a perspective view of another form of fluid chamber support structure attached to a wick chamber.
Figure 4A:
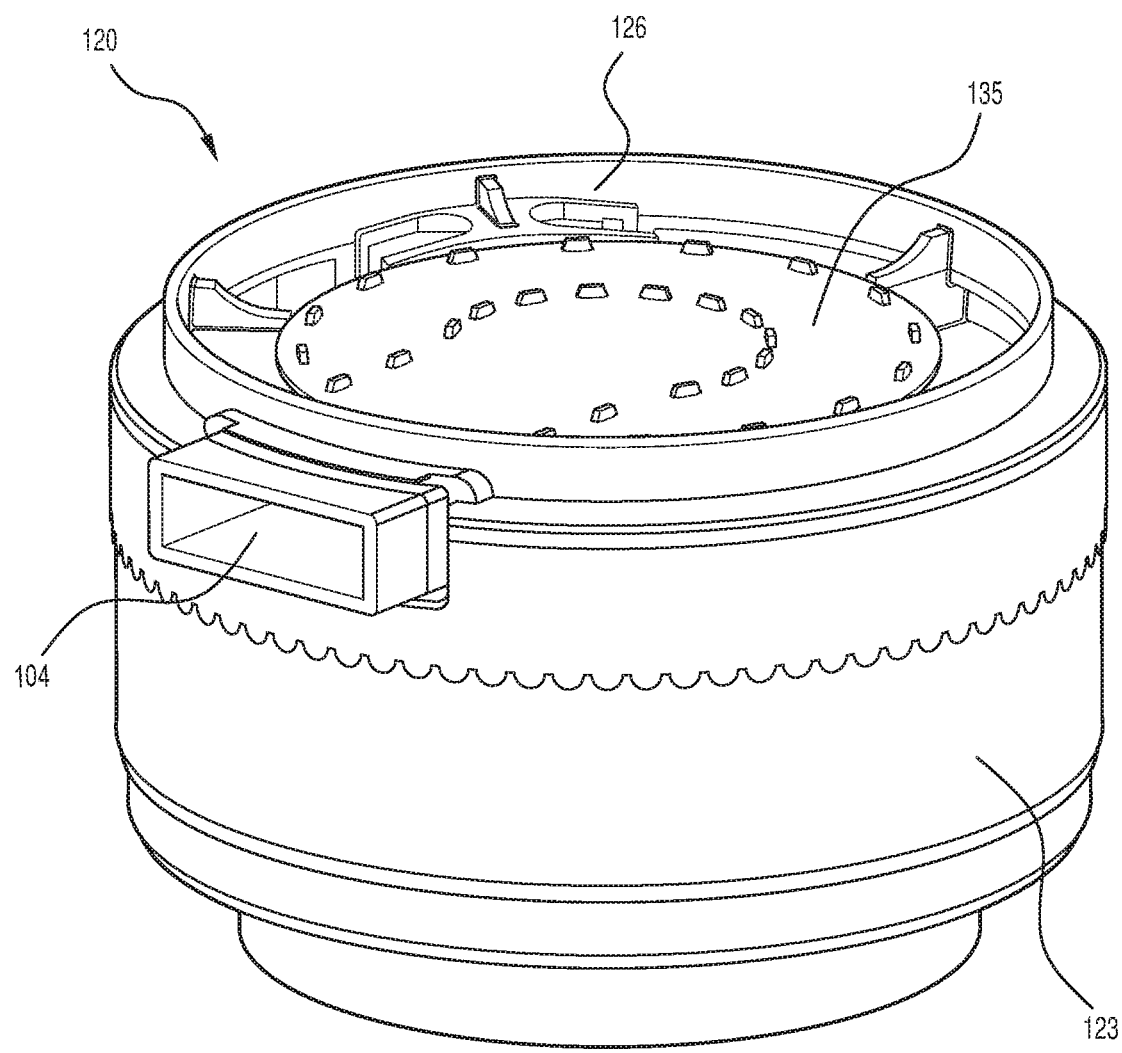
FIG. 4A is a perspective view of one form of fluid chamber.
Figure 4B:
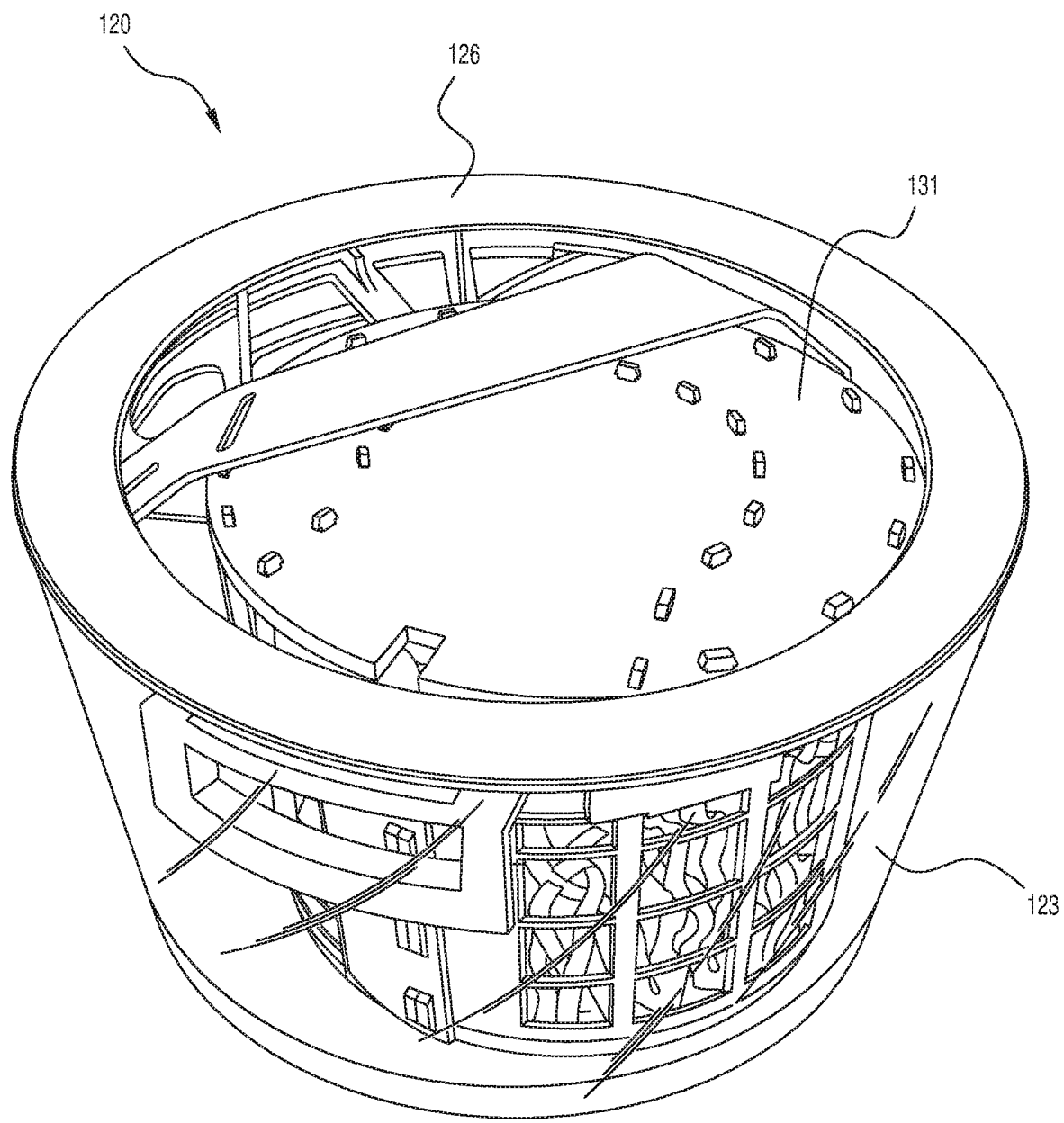
FIG. 4B is a perspective view of one form of fluid chamber comprising a fluid chamber support structure attached to a wick chamber.

The fluid chamber lid 126 is located above the fluid chamber tub or reservoir 123. The wick chamber 130 may be attached to and suspended from the lid 126, as shown in FIGS. 3A and 3*b*, so that the wick chamber 130 is located within the tub/reservoir 123 of the fluid chamber 123, as shown in FIGS. 4A and 4B. In one form, the wick chamber 130 is detachably attached to the lid 126. The wick chamber 130 may be detachably attachable to the lid 126 of the fluid chamber 120 via a snap fit configuration (such as by providing one or more rigid connectors on the wick chamber 130 that are configured to snap fit into one or more rigid connectors on the fluid chamber lid 126), interference fit (such as by providing one or more rigid connectors on the wick chamber that are configured to fit into one or more plastically deformable connectors on the fluid chamber lid or vice versa), threaded screw fit, or by any other suitable attachment system. Alternatively, the entire wick chamber 130 may be removable and replaceable.

The wick 131 may be held within the wick chamber 130, which supports the wick 131 within the fluid chamber 120. The wick chamber 130 may comprise an internal/interior chamber wall 132, an external/exterior chamber wall 133, and a base 134, as shown in FIGS. 6A to 7B. Optionally, the wick chamber 130 may also comprise a lid 135 configured to be attached to the lid 126 of the fluid chamber 120. In another form, one or more walls 132, 133 of the wick chamber 130 may be configured to attach to the fluid chamber lid 126. In one form, the wick chamber 130 may be configured to detachably attach to the lid 126. In this configuration, the wick 131 may be sandwiched between the internal 132 and external 133 chamber walls and is supported by the base 134 and located beneath the wick chamber lid 135 or fluid chamber lid 126, as the case may be.

Figure 5A:
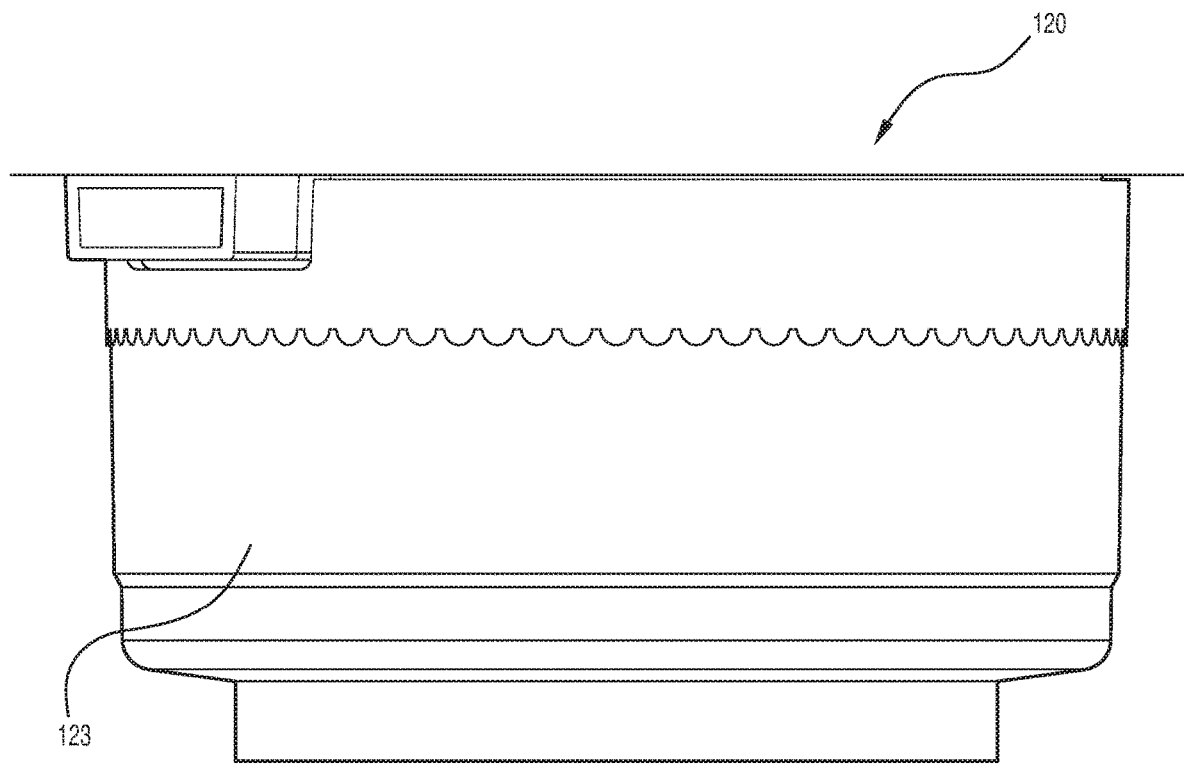
FIG. 5A is a cross-sectional side view of a fluid chamber.
Figure 5B:
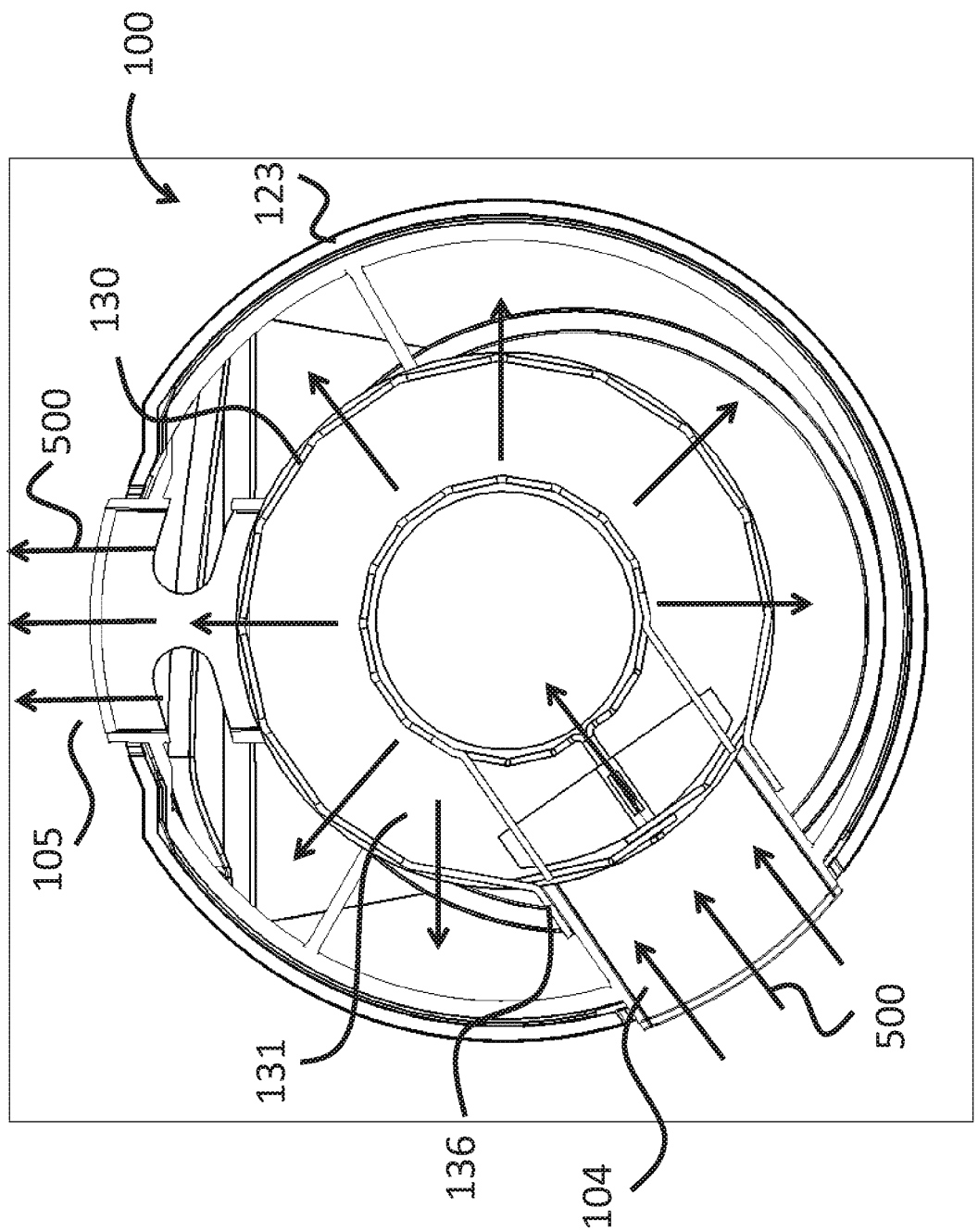
FIG. 5B is a schematic view of a fluid chamber from above showing the direction of gas flow through the wick chamber located within the fluid chamber.
Figure 6B:
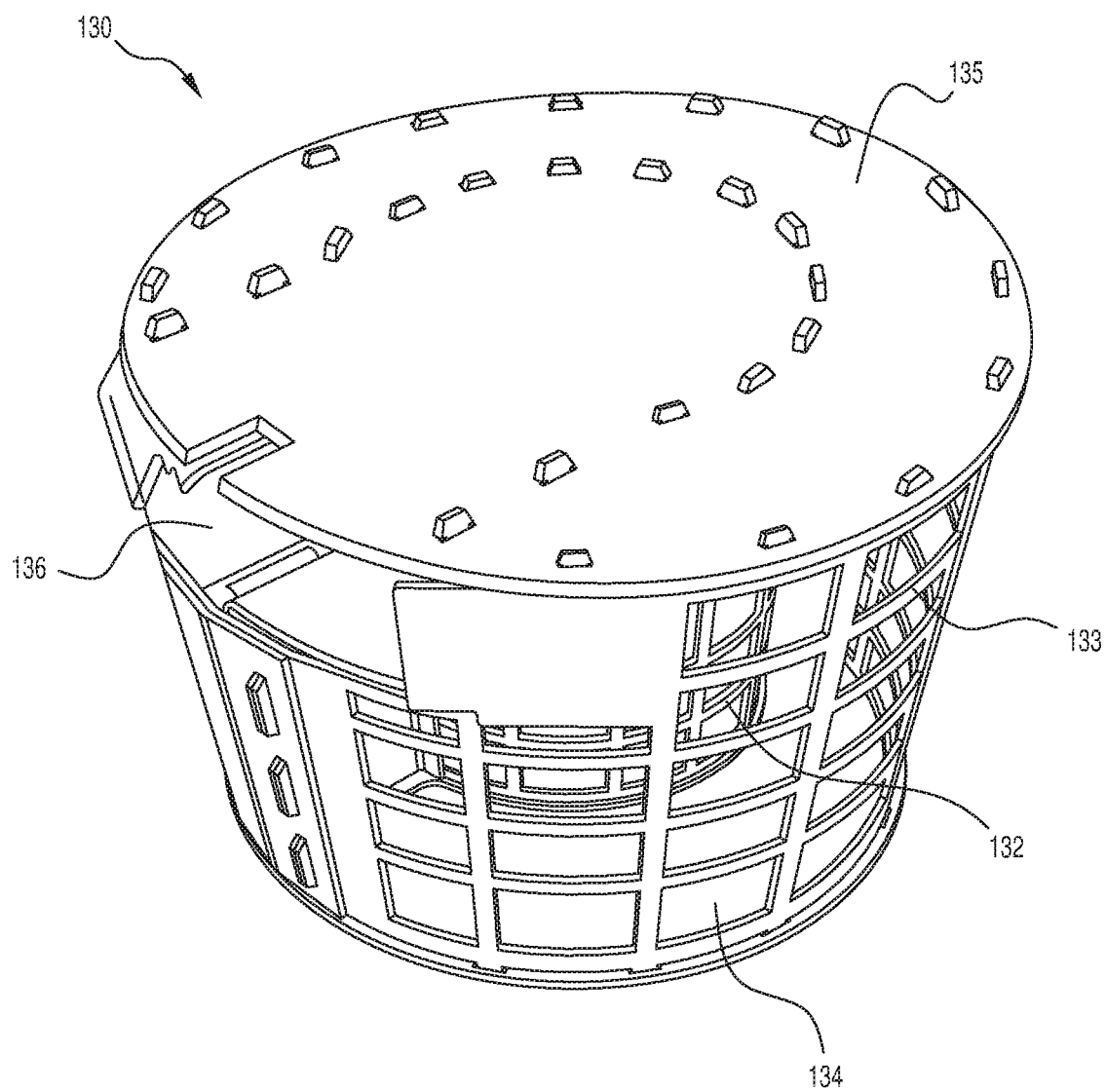
FIG. 6B is a perspective view of another form of wick chamber.
Figure 7A:
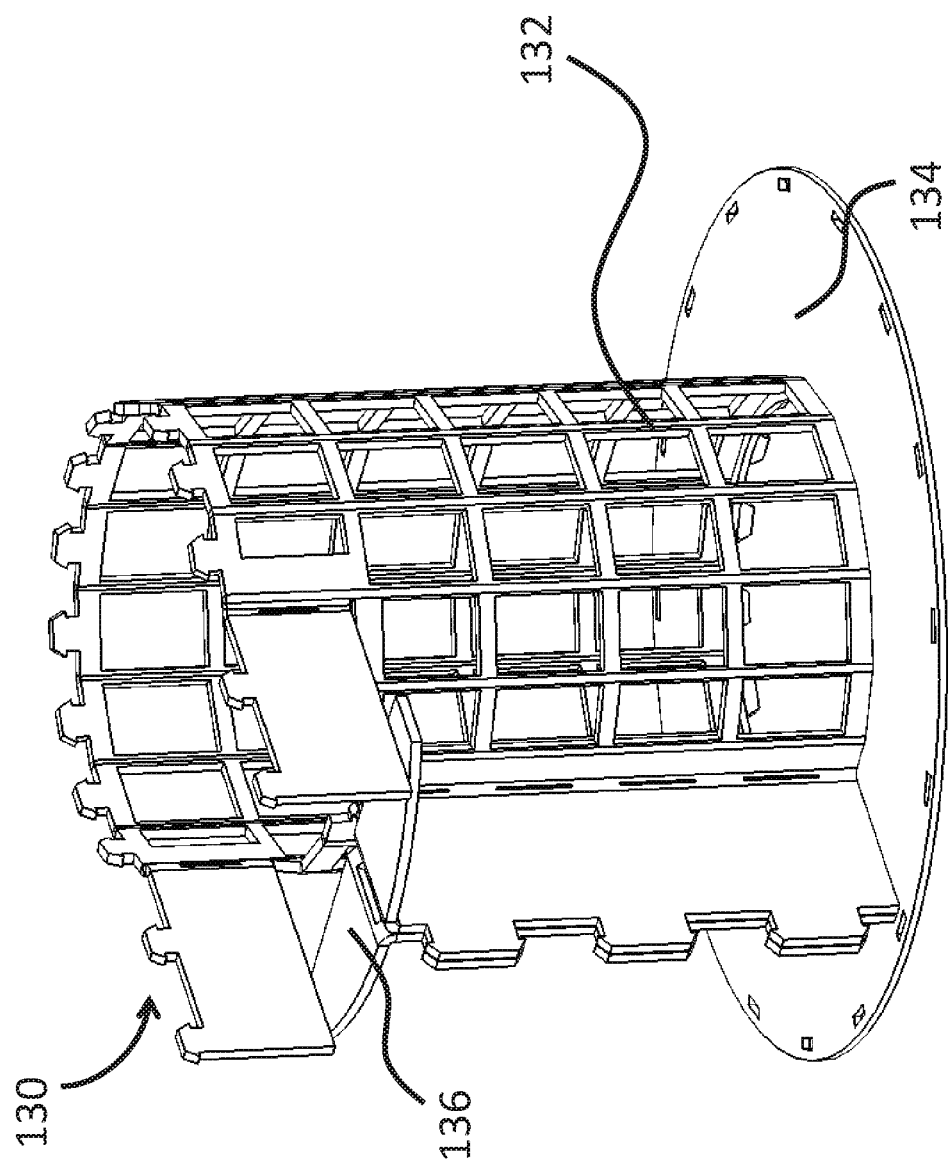
FIG. 7A is a perspective view of one form of internal wall of a wick chamber.
Figure 7B:
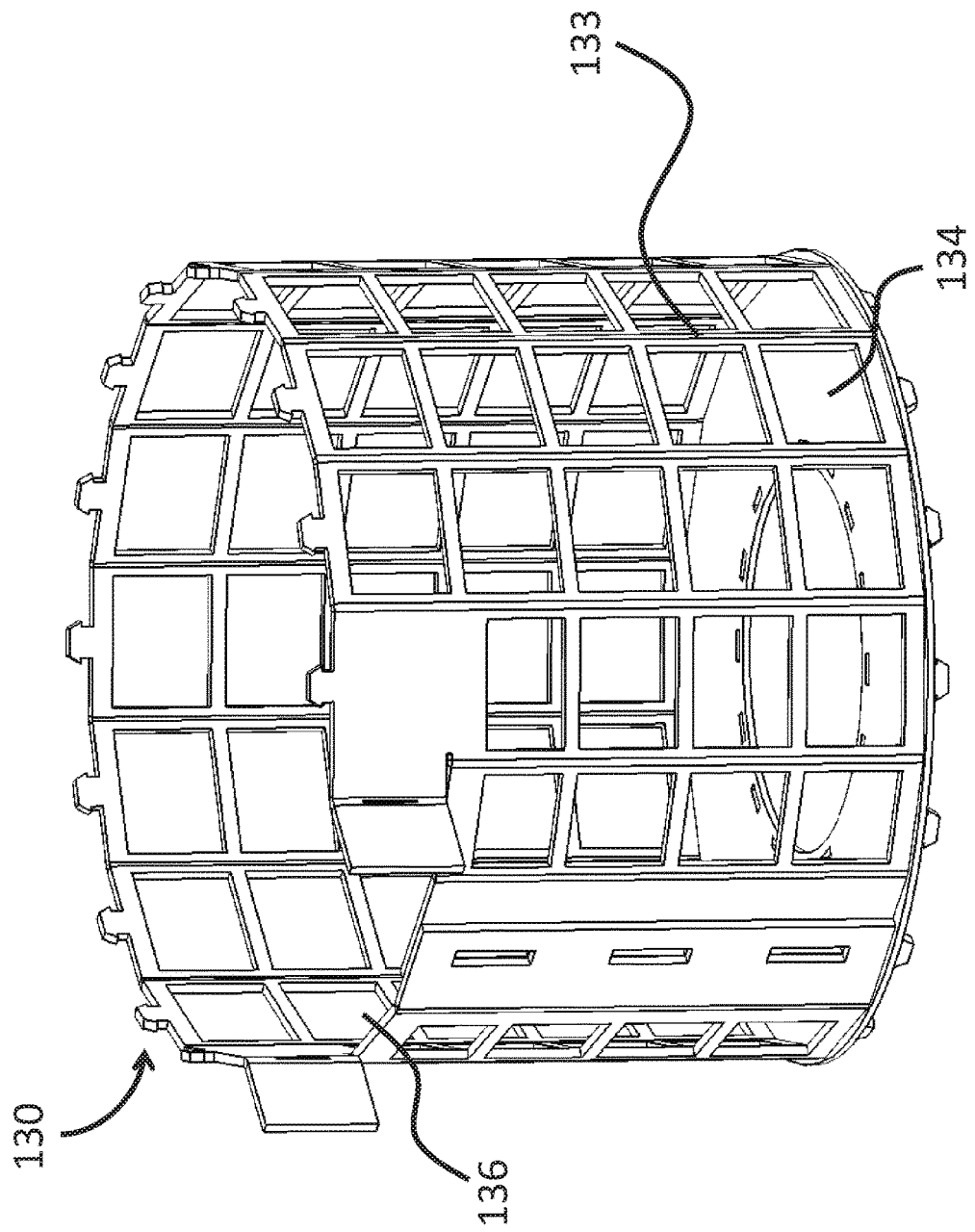
FIG. 7B is a perspective view of one form of external wall of a wick chamber.
Figure 8:
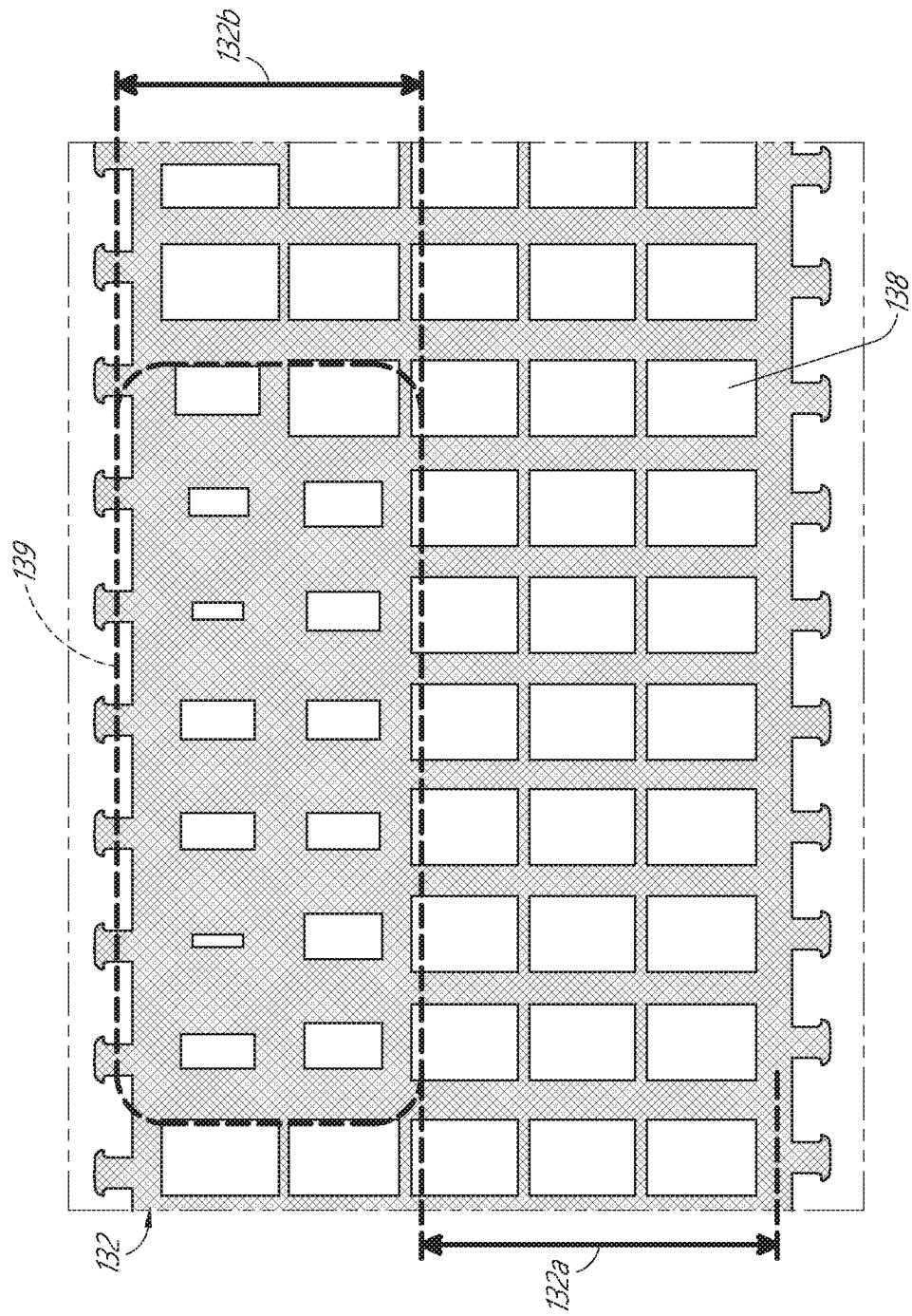
FIG. 8 is a top view of a portion of a wick chamber wall in a flattened configuration and comprising a plurality of diffusion apertures.

The wick chamber 130 also comprises at least one gas inlet 136 in fluid communication with the fluid chamber gas inlet 104. In this configuration, breathing gas from the flow generator 110 is blown through the fluid chamber gas inlet 104 and through the wick chamber gas inlet 136 before being directed across the wick 131, such as through a wick inlet portion 131a. The gas flow may diffuse upon entering the wick chamber 130 and before passing across the wick 131, as shown in FIG. 5B. This configuration provides an unimpeded inlet for gas to flow from a flow generator 110 to the wick 131, before the gas is emitted from the wick chamber 130 through at least one gas outlet and then through the fluid chamber gas outlet 105. Preferably, the wick chamber gas inlet(s) 136 and gas outlet(s) are arranged so that breathing gas passes across a significant portion of the wick 131 before exiting the wick chamber 130. The wick chamber 130 may comprise a gas outlet that is located substantially opposite to the gas inlet 136 to encourage gas 500 to pass across the wick, from one side to the other, before exiting the wick chamber 130. In another form, as shown in FIG. 1A, the wick chamber comprises a grille-like structure that has multiple openings. Each opening may form a gas outlet for the wick chamber 130.

The fluid chamber gas outlet 105 may be located substantially opposite the fluid chamber gas inlet 104 or the gas outlet 105 may be located closer to the gas inlet 104. For example, the gas outlet 105 may be located at an angle to the gas inlet 104, such as an angle between approximately 90° and 120° from the gas inlet 104. In another form, the gas outlet may be located on the fluid chamber lid or offset from a central point of the gas inlet. For example, the gas outlet may be centred at a point above or below the central point of the gas inlet.

In one form, as shown in FIGS. 2A to 2C and 2E, the wick 131 comprises a body comprising a hollow region. The wick 131 is positioned within the wick chamber 130 so that the hollow region of the wick 131 is downstream of the fluid chamber gas inlet 104 and the fluid chamber gas outlet 105 is downstream of the hollow region of the wick. Where the wick comprises a wick inlet portion 131a, the wick inlet is downstream of the fluid chamber gas inlet 104 and upstream of the hollow region.

Fluid 121, such as water, transfers from the wick 131 to the breathing gas, increasing the humidity of the breathing gas before the breathing gas exits through the gas outlet 105 and is directed to the patient.

In one form, as shown in FIGS. 2A to 2C, and 3A to 15, the wick 131 comprises a tubular cylinder that is located between the internal 132 and external 133 walls of the wick chamber 130. The diameter of the external chamber 133 wall may be greater than the diameter of the internal chamber wall 132. The internal chamber wall 132 is preferably spaced substantially equidistant from the external chamber wall 133 so that the internal and external chamber walls 132, 133 form concentric cylinders, between which the hollow cylindrical wick 131 is positioned.

In one form, as illustrated, the ratio of the diameter of the internal wick chamber wall 132 to the diameter of the external wick chamber wall 133 is uniform at approximately 1:1.88. In other forms, the ratio is non-uniform, such as where the internal wall 132 is of a different shape to the external wall 133 or where the internal wall 132 is located off-centre with respect to the external wall 133. In other forms, the ratio between the lateral dimension of the internal and external walls 132, 133 may be different to the ratio between the distal dimension of the internal and external walls 132, 133, such as where the wick chamber 131 has a rectangular configuration.

In one form, the gas inlet 104 of the fluid chamber 120 and/or wick chamber 130 is located to direct breathing gas through the side of the wick 131 so that the gas passes through the thickness of the wick 131, as shown in FIG. 5B.

The gas inlet 104 may be of any suitable size and shape. In one form, the gas inlet 104 is relatively large compared to the surface of the wick 131 facing the inlet 104. For example, the size of the gas inlet 104 may be at least one third of the size of the facing surface of the wick 131. Where the gas inlet 104 directs gas through the side of the wick 131, the facing surface of the wick 131 is the side surface of the wick 131 that is proximate the gas inlet 104. The size of the gas inlet may also effect the diffusion of gas flow across the wick. For example, the larger the inlet, the greater the diffusion of gas entering the wick chamber.

The surface area of the wick 131 that is exposed to gas flow has an influence on the amount of humidity that can be provided to the gas flow. For example, if a small surface area of the wick 131 is exposed to gas flow (because of a high fluid level within the fluid reservoir), the gas flow may not have an opportunity to evaporate enough fluid 121 from the exposed surface of the wick 131 to provide a sufficient level of humidification to the gas. Therefore, by providing a larger gas inlet to increase the diffusion of gas across the wick, greater humidification efficiencies may be achieved.

The level of fluid 121 in the fluid reservoir/tub lowers over time, as fluid 121 is evaporated and provided to the patient. If the fluid level is initially too high, the humidity level will be low at the beginning of a therapy session and will increase over time, as the fluid level drops. The decreasing fluid level increases the surface area of the wick 131 that is exposed to gas flow. As the wick surface area increases, the humidity provided to the gas flow also increases—to a point.

Any pronounced increase in the humidity of the gas flow could result in an uncomfortable or undesirable change in conditions for the patient. This problem may be mitigated by providing one or more target fluid level indicators on the fluid chamber tub 123 and/or providing one or more target fluid level indicators on the wick chamber 130. For example, indicators may be used to mark the maximum and/or minimum target fluid levels. If the fluid chamber 120 is filled within this target range, the surface area of wick 131 exposed to gas flow will be such that the humidifying effect is maximized (by effectively saturating the output gas). The humidifying effect may be maximized regardless of the extent to which the fluid level drops, as long as the fluid chamber 120 holds at least some fluid to distribute across the wick 131.

Factors that influence the effectiveness of the wick 131 per unit surface area, and that therefore effect the optimum fill height of the fluid chamber 120 include:

The wick structure: This affects the surface area of the wick exposed to air flow. For example, a wick having a lattice-like structure or a foam-like structure may have a greater surface area than a wick having a substantially smooth structure.

The wick thickness: In one form, the wick comprises a 10-sheet cellulose lattice. However, if the number of sheets is increased or decreased, the effective surface area of the wick that is exposed to gas flow will increase or decrease accordingly.

The wick material: On a smaller scale, using different fibers or base material for the wick can increase or decrease the exposed surface area of the wick. In the illustrated configuration, the wick is a cellulose based fiber lattice. Other materials that can be configured into a lattice and used for the wick material include polyester basted fibers, or sintered wick materials as opposed to fibers.

The gas flow rate: The higher the gas flow rate, the greater the volume of gas that will be exposed to the wick per unit of time. The average flow rate and maximum flow rate may both be important depending on the application.

The ambient humidity/temperature of the operating environment: The wick generally operates using the same principles as an evaporative cooler, so ambient humidity and temperature will affect the performance of the wick and the humidification device.

In one form, the wick chamber 130 may assist in diffusing or directing gas blown through the fluid chamber 120 and therefore across the wick 131, as shown in FIGS. 5B to 8, 10A, 12A and 12B.

It has been found that the wick humidification device 100 is most effective when the incoming gas flow from the gas flow generator 110 is evenly distributed across the exposed surface area of the wick 131. This ensures that a large surface area of fluid 121 (held within the wick 131) is in contact with the moving gas flow 500 to allow evaporating fluid 121 from the wick 131 to humidify the gas 500. Consequently, the efficiency of the humidification device 100 may be maximised by dispersing the flow of gas substantially evenly through the fluid chamber 120 and across the wick 131 as the gas flow 500 enters the fluid chamber 120. Advantageously, it may also be simpler to maintain a fully saturated gas output 500 under all input gas flow rates and ambient humidity conditions by dispersing the gas flow across the wick 131.

Evenly dispersing the gas flow 500 through the fluid chamber 120 may also prevent high velocity gas from passing across only a portion of the wick 131, causing that portion to dry out, which would result in a decreased humidity output. High localised velocities of gas 500 passing across only a portion of the wick 131 may also produce fluid aerosols, which may undesirably result in bacteria transportation by aerosol, due to the large nature of the aerosolised fluid particles that may harbour bacteria.

The humidification device 100 may comprise a dispersion system configured to disperse the gas flow through the fluid chamber 120 and/or across the wick 131. Different forms of dispersion system may disperse gas through the device 100 in many different ways. For example, one or more components of the device 100 may be configured to direct or control gas flow 500 through the device 100. In another form, the device 100 may comprise a diffuser for diffusing gas flow 500 through or over the wick 131. In one form, the device 100 may comprise a control system or controller for directing or controlling gas flow through the device 100. The control system/controller may comprise one or more control valves for directing gas flow. In one form, one or more control valves may also act as a diffuser.

In some forms, the wick chamber 130 may comprise a foraminous structure for holding the wick 131. Openings formed in the foraminous structure may assist dispersion of gas across the wick. The openings of the foraminous structure may also provide multiple inlets 136 and/or outlets 137 of the wick chamber through which gas can pass.

In one form, one or each of the internal and external walls 132, 133 of the wick chamber 130 may form a baffle comprising diffusion apertures 138 of varying sizes. The diffusion apertures 138 may be of any suitable regular or irregular shape, including but not limited to square, rectangular, circular, triangular, hexagonal, octagonal, oval, elliptical, quadrilateral, or amorphous shapes. The internal and/or external wall 132, 133 may comprise different shaped diffusion apertures 138 from left to right, top to bottom, or throughout the wall 132, 133 in a random or regular arrangement. For example, a lower region 132*a*, 133*a* of the internal and/or external walls 132, 133 respectively may comprise quadrilateral diffusion apertures 138 and an upper region 132*b*, 133*b* of the internal and/or external walls 132, 133 respectively may comprise circular apertures 138. The external wall 133 may comprise different shaped diffusion apertures 138 to the internal wall 132.

The wick chamber walls 132, 133 may comprise different sized diffusion apertures 138, as shown in FIGS. 8 and 10A. FIG. 8 shows a flattened view of one form of internal wick chamber wall 132 comprising diffusion apertures 138 of varying sizes. The diffusion apertures 138 may be different sizes from left to right, top to bottom, or throughout the wall 132, 133 in an irregular or regular arrangement. For example, a lower region 132*a*, 133*a* of one or both wick chamber walls 132, 133 may comprise larger diffusion apertures 138 than an upper region 132*b*, 133*b* of one or both walls 132, 133, as shown in FIG. 8. In one form, the external wick chamber wall 133 may comprise different sized diffusion apertures 138 to the internal wick chamber wall 132. For example, the diffusion apertures 138 of the external wick chamber wall 133 may be smaller or larger than the diffusion apertures 138 of the internal wick chamber wall 132.

Also as shown in FIG. 8, one region of the internal 132 or external 133 wall of the wick chamber 130 may comprise diffusion apertures 138 that are smaller than diffusion apertures at another region of the wall 132, 133. In one form, a region of the internal wall 132 comprising smaller diffusion apertures 138 may be located substantially opposite to the wick chamber inlet 136. In one form, there may also be fewer diffusion apertures 138 in this region than in one or more other regions of the internal wall 132 of the wick chamber 130.

In one form, a select region 139 of a portion of the internal wall 132 substantially opposite the gas inlet 136, such as at the upper portion 132*b* of the internal wall 132, may comprise smaller diffusion apertures 138 and/or a reduced number of diffusion apertures 138 than another region or than the rest of the internal wall 132. The diffusion apertures 138 in the select region 139 may also be smaller in size and/or in number than apertures 138 of the external wall 133, so that the select region 139 acts as an enhanced baffle that helps to diffuse gas flow through or over the wick 131. This configuration decreases the surface area through which the gas can flow, thereby reducing the volume of gas 500 that can pass straight through the portion of the wick 131 that is adjacent to the select region 139 of the internal wall 132. The gas 500 that is unable to pass through the select region 139 of the internal wall 132 is deflected from the wall 132 and dispersed through or over other areas of the wick 131 to allow a more even distribution of gas flow 500 through or over the wick 131. In one form, the internal wall 132 may comprise more than one select region 139 to modify the dispersion pattern of gas across the wick 131. In another form, the external wall 133 or both the internal and external walls 132, 133 comprise at least one select region having diffusion apertures 138 that are smaller in size and/or reduced in number compared to other diffusion apertures 138 in the external and/or internal walls 132, 133.

Figure 9:
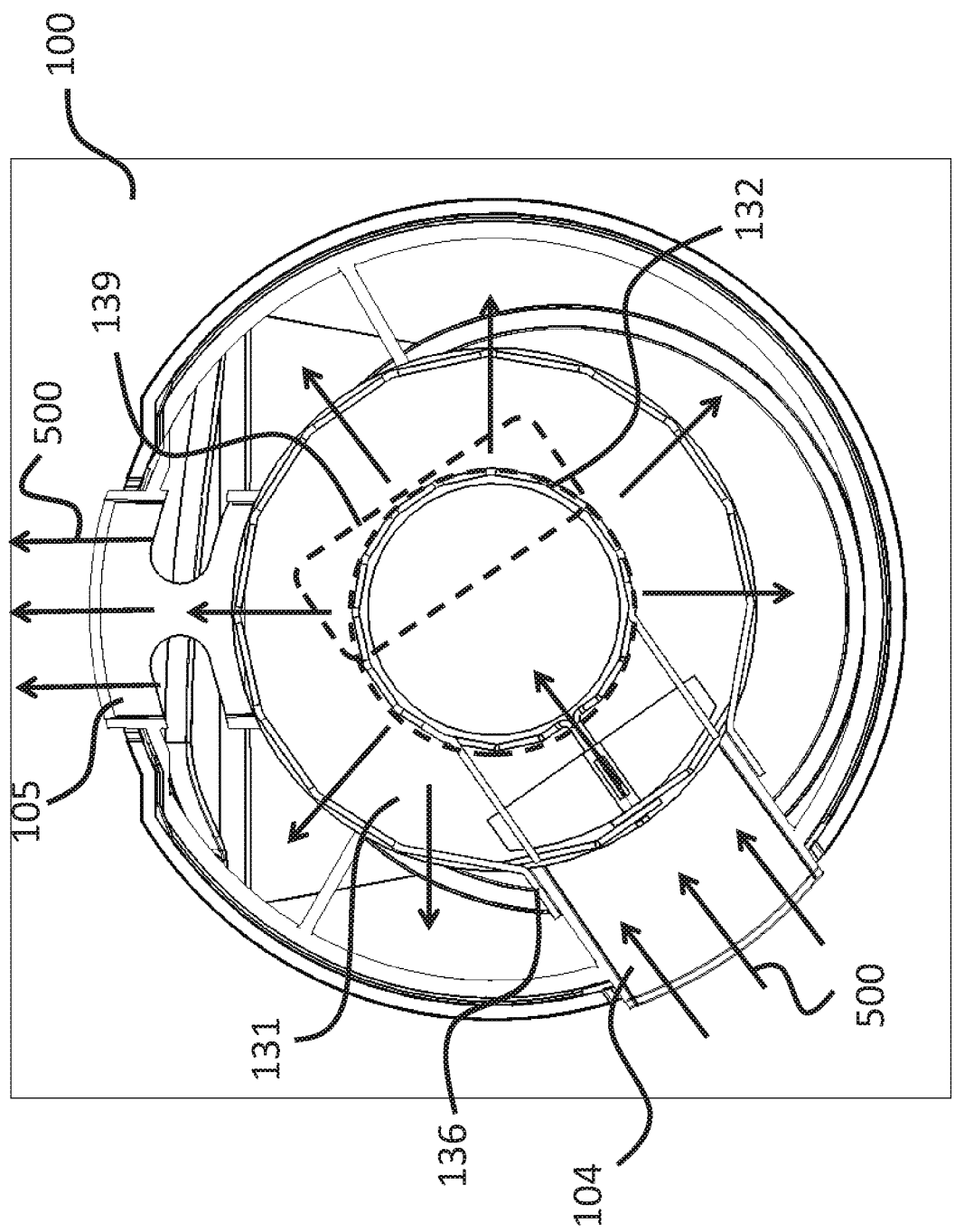
FIG. 9 is a schematic view of a fluid chamber from above, showing the direction of gas flow through the fluid chamber when the wick chamber of FIG. 8 is located within the fluid chamber.

FIG. 9 shows a cross-sectional top view of the fluid chamber 120, wick chamber 130, and wick 131. The internal wall 132 of the wick chamber 130 comprises a select region 139 of a reduced number of diffusion apertures 138 to provide an enhanced baffle. The select region 139 of the internal wall 132 is located substantially opposite the inlet 136 to the wick chamber 130 so that gas 500 is directed through the inlet 136 toward the enhanced baffle 139. In one form, the select region/enhanced baffle 139 may be located proximate to the gas outlet 105 of the fluid chamber 120, as shown in FIG. 9.

In one form, the total open area of the select region 139 (i.e. the total area the diffusion apertures 138 within the select region 139) is between approximately 20% to 70% of the total area of the respective internal or external wall 132, 133 of the wick chamber 130.

Figure 10A:
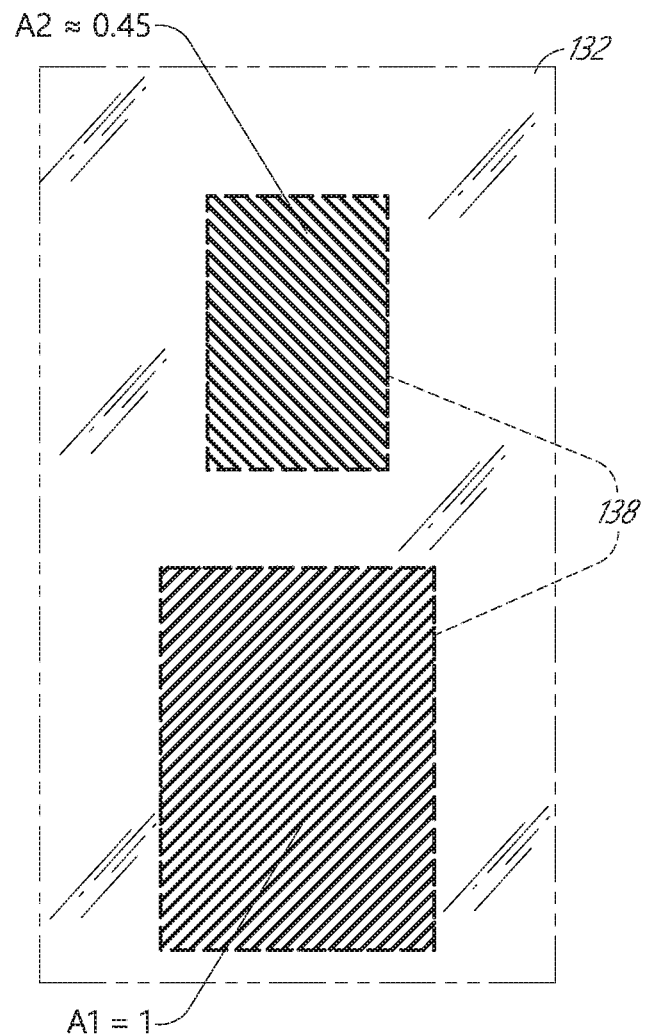
FIG. 10A is an enlarged schematic view of the wick chamber of FIG. 8, showing different sized diffusion apertures.

In one form, the total open area of the select region 139 may be between 20% and 90% less than the total open area of one or more other regions of the internal 132 and/or external wall 133, as shown in FIG. 10A. For example, the open area in the select region 139 located in the upper portion 132b of an internal wick chamber wall 132 may be 45% less than the open area in the lower portion 132a of the internal wall 132.

In one form, the select region 139 of reduced diffusion apertures 138 (diffusion apertures that are fewer in number and/or smaller in size than diffusion apertures in one or more other regions of the wick chamber) may substantially span the length of the wick chamber 130. Where the wick chamber 130 is substantially cylindrical and comprises a hollow interior, as shown in FIG. 9, the select region 139 may extend around the internal perimeter of the wick chamber 130 (as indicated by the dashed lines in FIG. 9) and/or around the external perimeter of the wick chamber 130. Where the wick chamber 130 is polygonal, the select region 139 may extend around the perimeter of the polygon or across at least one front or rear surface of the polygon.

In one form, the select region 139 of reduced diffusion apertures 138 may span the height of the upper 132b, 133b or lower 132a, 133a portion of the internal and/or external wall(s) 132, 133 of the wick chamber 130. In the embodiment shown in FIG. 9, the upper portion 133b (and select region 139) of the wick chamber internal wall 132 spans approximately 40% of the total height of the internal wall 132. In other forms, the select region 139 of reduced diffusion apertures 138 may span between approximately 5% to 95% of the total height of an internal 132 and/or external wall 133 of the wick chamber 130. For example, the upper portion 132b, 133b and/or select region 139 may span approximately 20%, 25%, 30%, 40%, 50%, 60%, 67%, 70%, 80%, or 90% of the total height of the internal 132 and/or external wall 133 of the wick chamber 131. The location and size of the select region 139 of reduced diffusion apertures 138 may depend on the size and location of the wick chamber inlet 136.

Figure 10B:
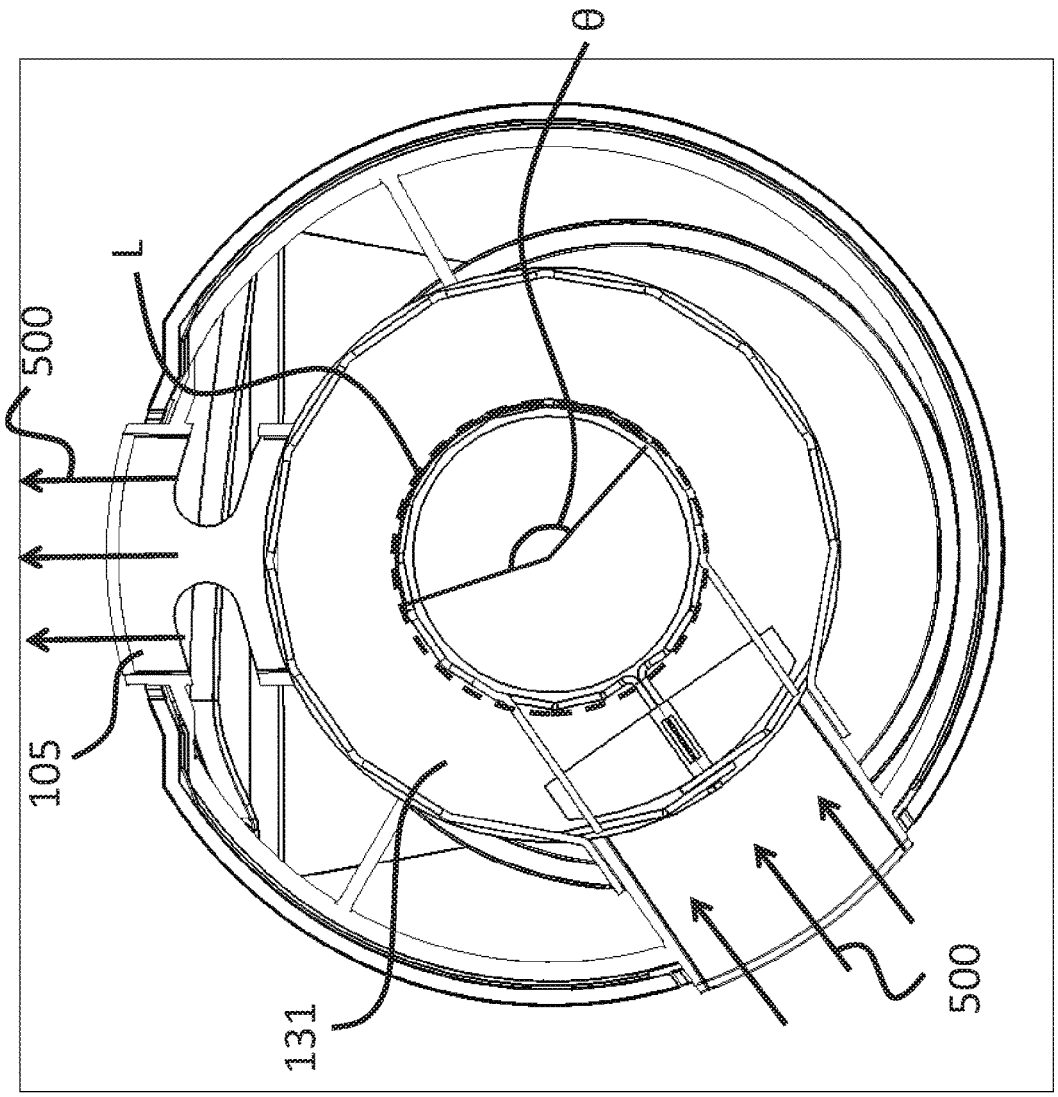
FIG. 10B is a schematic view of a fluid chamber from above showing the angle at which gas from the fluid chamber inlet may be diffused through or over the wick.

The select region 139 may span only a portion of the perimeter of the internal 132 and/or external walls 133 of a cylindrical wick chamber 130, so that the select region 139 forms an arc. The arc may span between approximately 20% to 90% of the total length of the respective wick chamber wall 132, 133. For example, the arc may span approximately 20%, 25%, 30%, 33%, 40%, 50%, 60%, 70%, 78%, 80% or 90% of the perimeter of the internal 132 and/or external 133 wick chamber wall. In one form, the select region 139 may be located on the internal wall 132 of the wick chamber 130 and the arc length may span approximately 45% of the length of the internal wall 132, as shown in FIG. 10B. In this form, the arc of the select region 139 forms an angle θ of approximately 162° (2.83 rad) from the central axis of the cylinder formed by the internal wall 132 of the wick chamber 130. It has been found that this configuration helps to disperse gas flow substantially evenly across the interior surface of the cylindrical wick 130.

In another form, it may be possible to increase the flow resistance through the region of the wick chamber internal wall 132 located substantially opposite the wick chamber inlet 136 by increasing the number of diffusion apertures 138 in this target region, while increasing the surface area of the solid portions of the wall 132. In other words, the wall surface area that is taken up by a solid region of the wall 132 increases, but the wall 132 includes more apertures 138 having smaller surface areas. Increasing the wall surface area within the target region results in a reduction in the total surface area of the apertures, thereby increasing the flow resistance of this region. This configuration may decrease the surface area across which gas may pass relative to adjacent areas of the wick chamber internal wall 132, causing gas to disperse across other areas of the wick 131.

In another form, the humidification device 100 may comprise a blade diffuser 140a to diffuse gas from the gas inlet 104 through the fluid chamber 120 and across the wick 131. The blade diffuser 140a may be located in or proximate to the fluid chamber gas inlet 104 or wick chamber gas inlet 136 so that gas is directed through the blade diffuser 140a and is dispersed before passing across the wick 131. Diffusers may decrease the velocity of gas flow, while increasing the static pressure.

Figure 11A:
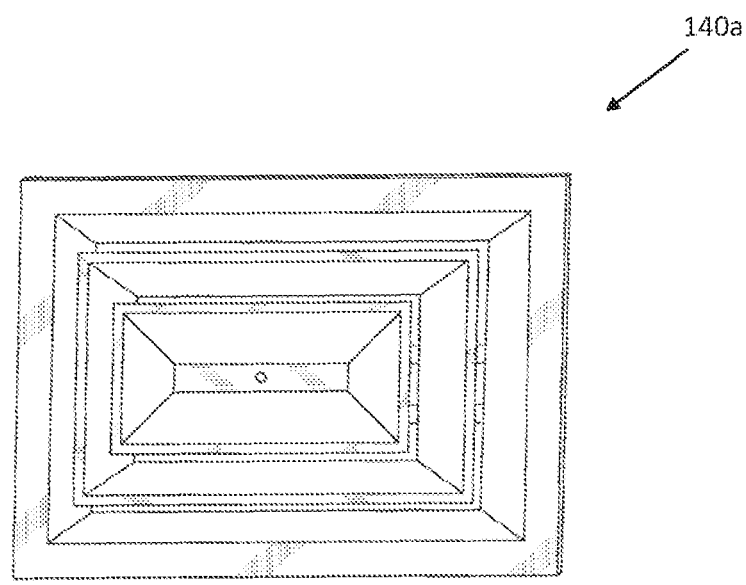
FIG. 11A is a perspective view of one form of diffuser that may be used to diffuse gas flow through or over a wick of a wick humidifier.
Figure 11B:
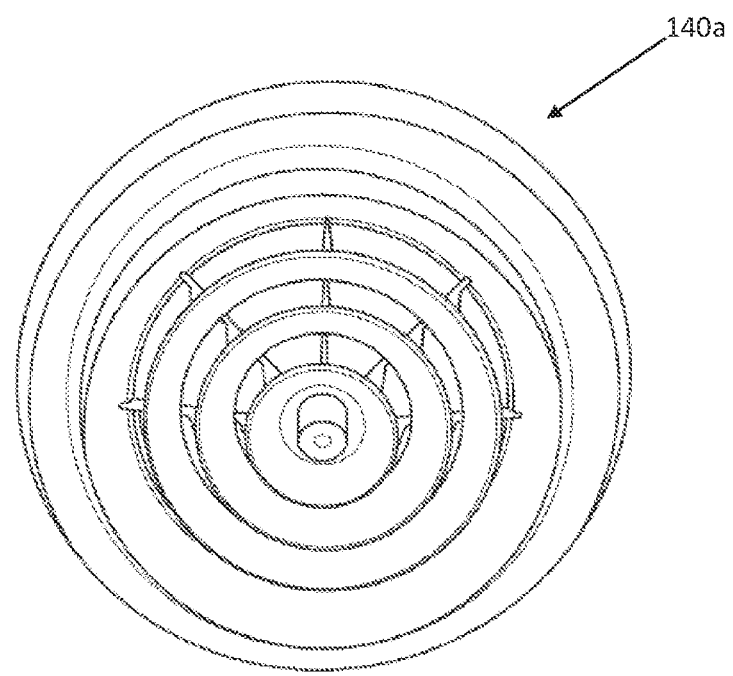
FIG. 11B is a perspective view of another form of diffuser that may be used to diffuse gas flow through or over a wick of a humidification device.

In one form, the diffuser 140a may be shaped similarly to a louvre bladed diffuser, as shown in FIGS. 11A and 11B. The diffuser 140a may be of any suitable form, including but not limited to a straight bladed diffuser, linear slot diffuser, swirl diffuser, jet diffuser, barrel diffuser, perforated diffuser, plain face diffuser, louvre bladed diffuser, or any combination of these.

In one form, the humidification device may comprise a diffuser in the form of a grille 140b. The grille 140b may be formed from a plurality of interconnecting grille members 142 that may be spaced from each other and connected together at intersecting points in a regular or irregular arrangement. A grille member 142 may be oriented substantially vertically, horizontally, or diagonally. A grille member 142 may be straight, curved, or angled. A grille member 142 may have a substantially uniform or non-uniform shape. For example, a grille member 142 may have a substantially curved "S" shape. A grille member 142 may have a substantially uniform thickness or a non-uniform thickness, such as being wider at the bottom than the top or vice versa, or wider or thinner at a central region of the grille member 142.

Figure 12A:
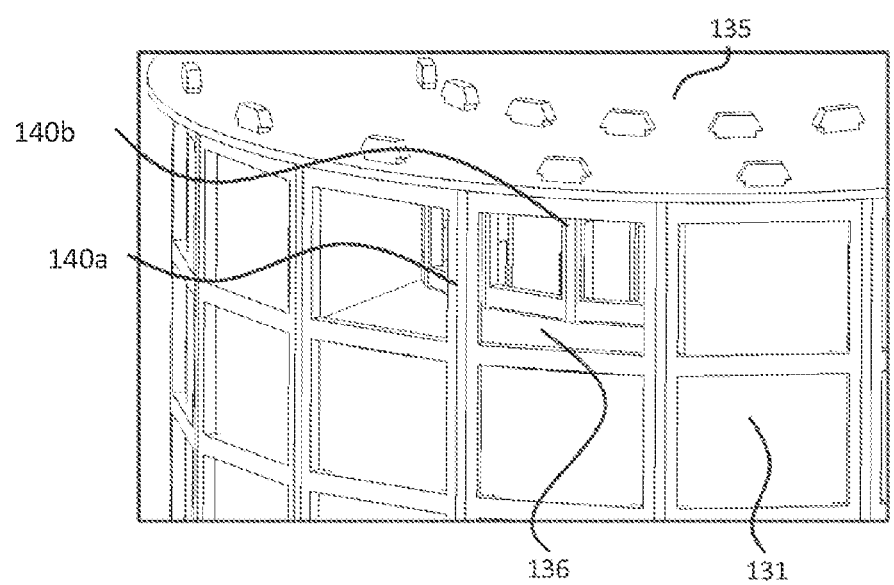
FIG. 12A is a perspective view of one form of wick chamber comprising an exterior chamber wall having a plurality of diffusion apertures to form an exterior grille and also comprising an interior chamber wall having a plurality of diffusion apertures to form an interior grille at the wick chamber inlet.
Figure 12B:
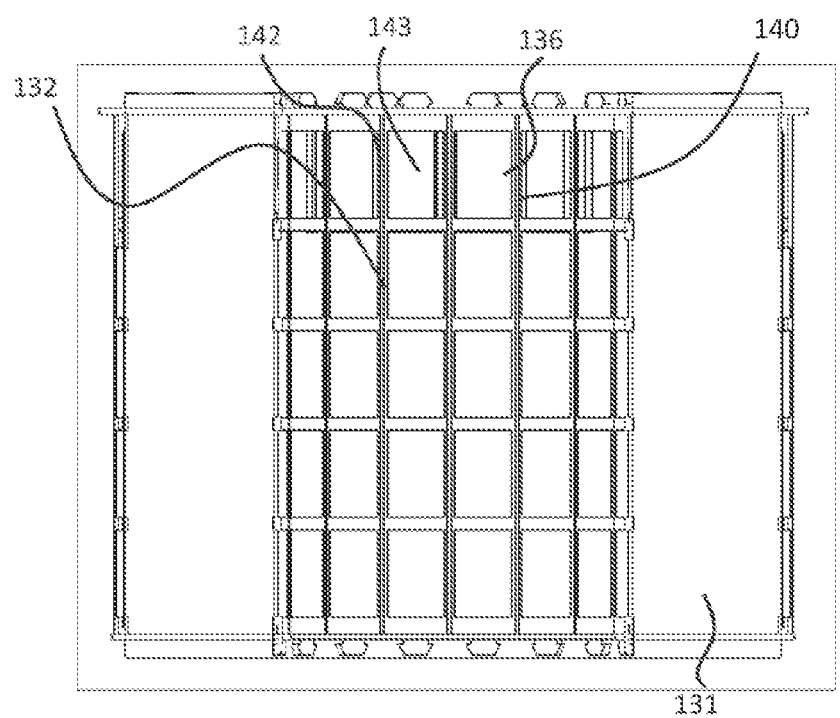
FIG. 12B is a cut-away perspective view of a fluid chamber for a humidification device and showing an internal wall of one form of wick chamber with grille.

In one form, the diffuser may comprise a substantially regular arrangement of diffusion grille apertures 143 interspersed between grille members 142 to form a diffusion grille 140b for diffusing gas across the wick 131, as shown in FIGS. 12A and 12B. The grille apertures 143 may be of any regular or irregular shape, such as quadrilateral, circular, triangular, or amorphous shapes. In a preferred form, the grille apertures 143 are rectangular. Any number of grille members 142 can be used to increase or decrease the size of the grille apertures 143 between the grille members 142 and to therefore influence the flow of gas through the inlet 136. At least one of the grille apertures 143 may form a gas inlet 136 of the wick chamber 130. Optionally, the wick chamber comprises multiple gas inlets and/or gas outlets.

The grille 140b may be of any suitable design to disperse gas flow across the wick 131. For example, the grille 140b may comprise an egg crate grille, bar grille, transfer grille, or any combination of these.

A cylindrical, tubular wick chamber 130 having an external wall 133 and an internal wall 132 may comprise a double layered grille 140b at the wick chamber inlet 136, as shown in FIG. 12A. For example, the external wall 133 may comprise an arrangement of diffusion grille apertures 143 within a grille 140b that extends across the wick chamber inlet 136 Similarly, the internal wall 132 may comprise an arrangement of diffusion grille apertures 143 within a grille 140b that extends across the wick chamber inlet 136. Alternatively, only the external wall 133 or the internal wall 132 may form a grille 140b across the wick chamber inlet 136. In the embodiment shown in FIG. 12B, only the internal wall 132 forms a grille 140b across the inlet 136.

In yet another form, the humidification device 100 may comprise a fibrous diffuser or a diffuser comprising a fabric/textile diffuser that spans a length of the wick chamber inlet 136 to disperse gas across the wick 131. In one form, a fabric diffuser is located at the gas inlet 136 on the internal wall 132 of a cylindrical wick chamber 130. In another form, a fabric diffuser is located at the gas inlet 136 on the external wall 133 of a cylindrical wick chamber 130. Alternatively, a fabric diffuser may be located at the gas inlet 136 at both the internal 132 and external walls 133 of the wick chamber 130. The fabric used in the diffuser may be any form of material, such as fibrous material. Preferably, the fabric is a woven material.

Figure 13:
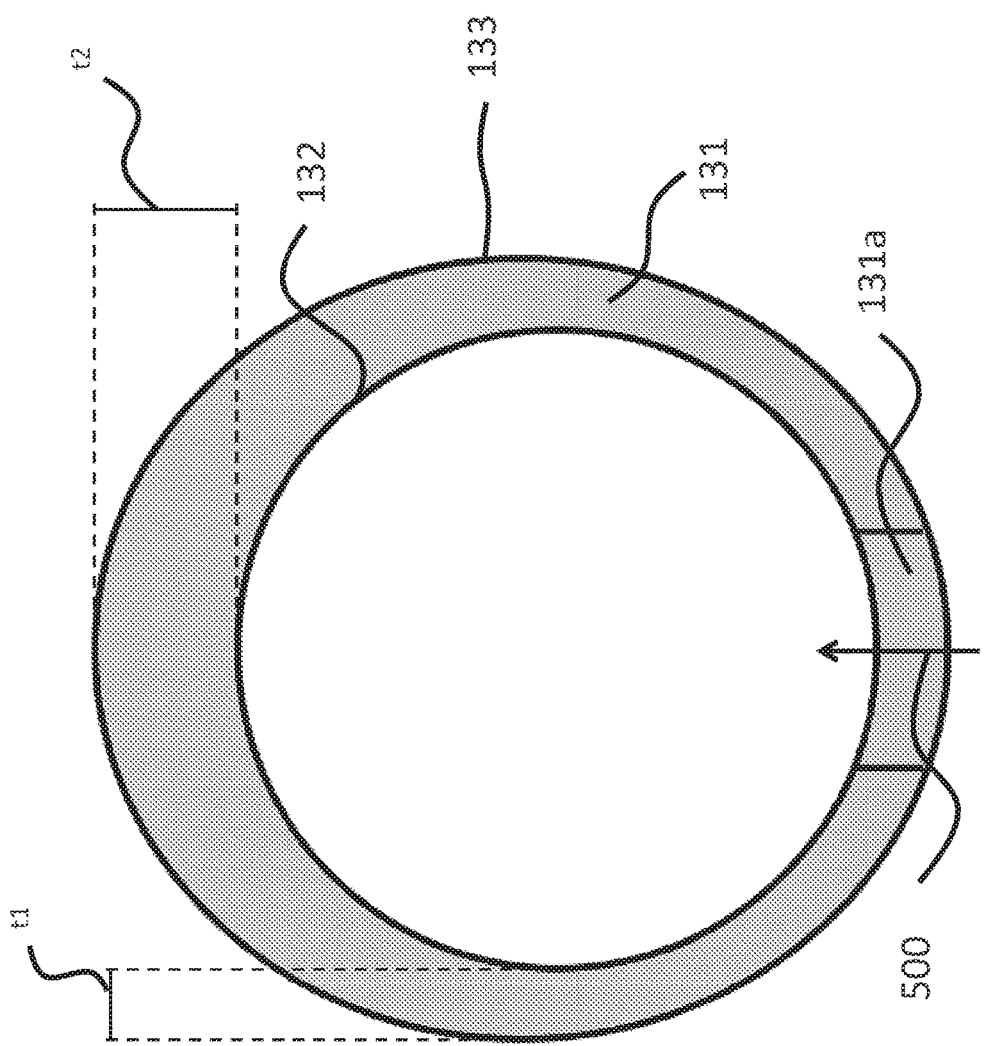
FIG. 13 is a schematic top view of one form of wick having a variable thickness.

In one form, the wick 131 may be configured to help diffuse gas flow across the wick 131. In this form, the body of the wick 131 may have a variable thickness. For example, in a substantially cylindrically shaped tubular wick 131 having an internal space or hollow region, as shown in FIG. 13, the portion of the wick 131 nearest the wick chamber gas inlet 136 (the wick inlet portion 131a) has a first thickness t1 that may be thinner than the second thickness $t_2$ of the wick portion located substantially opposite the wick chamber inlet 136. Conversely, the first thickness t1 of the wick 131, at the wick inlet portion 131a, may be thicker than the second thickness $t_2$ of the opposite wick portion. The side portions of the wick 131 may be of a third thickness that may be thinner, of substantially equal thickness, or thicker than the first or second thicknesses of the wick inlet portion 131a and opposing wick portion respectively. In the embodiment shown in FIG. 13, the wick inlet portion 131a and side portions are substantially the same thickness whereas the wick portion opposing the gas inlet 136 is of a greater thickness. Increasing the thickness of the wick portion opposite the wick chamber inlet 136 will increase the impedance of gas flow through that portion of the wick 131. Therefore, gas will tend to disperse across the wick 131 more evenly around the inside surface of the tubular wick 131, with a small amount of gas passing across the thick portion of the wick 131 and the remaining gas dispersing and passing through the thinner portions of the wick 131.

A wick 131 having a wick body comprising at least two spaced apart opposed portions and at least one internal space/hollow region, forming the space between the first and second opposed portions, may also encourage gas to disperse throughout the body of the wick. For example, gas entering the wick may initially flow through a first portion or wall of the wick body before the gas reaches the hollow region. In the hollow region, the gas may spread out to fill the hollow region and may then be pushed through the second portion or other portions/walls of the wick body as more gas enters the hollow region. Furthermore, gas directed through the wick inlet portion 131a can be distributed throughout the internal space prior to passing through the second portion of the wick body. This increases the surface area of the wick 131 through with the gas can pass before being directed through the outlet, increasing the humidity output and therefore the effective efficiency of the apparatus.

In one form, the wick may be at least partially disposed between the gas inlet and the gas outlet of the fluid chamber to cause gas that enters the fluid chamber via the gas inlet to pass through or over a first of two spaced apart portions of the wick body, across the space or hollow region between the two body portions, and then through or over the second portion of the wick body before exiting the fluid chamber via the gas outlet.

The gas inlet 136 to the fluid chamber 120 and/or the wick chamber 130 may also be configured to enhance the dispersion of gas across the wick 131.

Figure 14B:
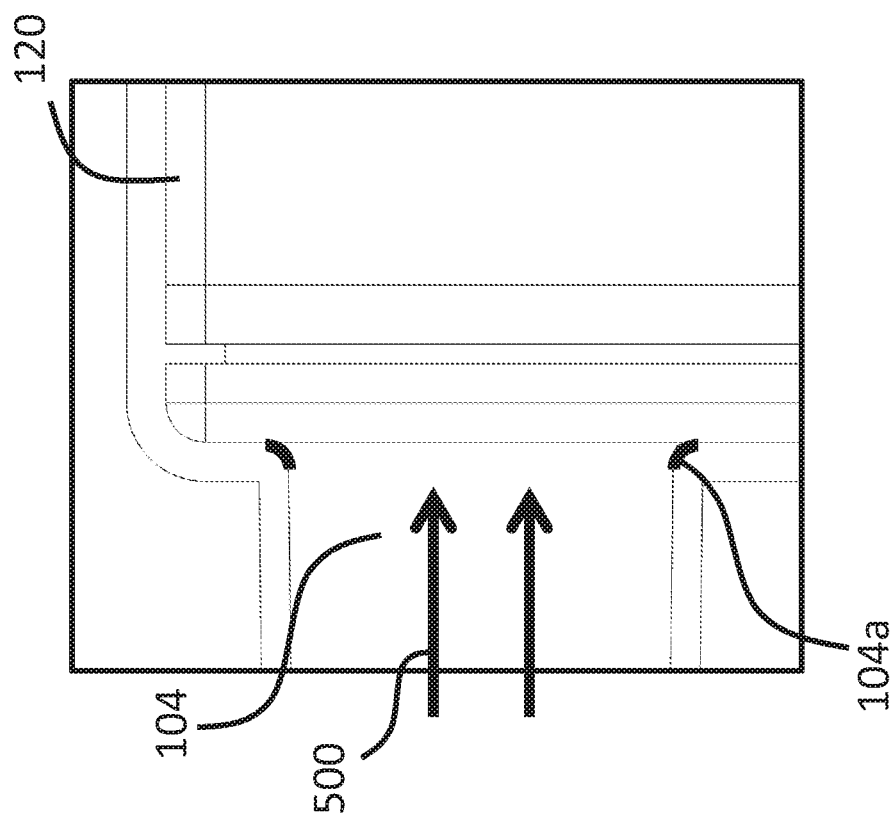
FIG. 14B is a cross-section view of a generic curved radius gas inlet to a chamber, the curved radius at the inlet being used to exploit a Coanda effect by encouraging the diffusion of gas flowing through the inlet.

In one form, the gas inlet 136 to the wick chamber 130 enters the chamber 130 at a transition region at which a curved wall of the gas inlet curves outwardly to form the external wall 133 of the wick chamber. In other words, the corner formed at the transition region where the gas inlet meets the external wall of the wick chamber comprises a curved radius 104a, as shown in FIG. 14A. The curved radius 104a of the gas inlet 136 at the transition region encourages gas entering the wick chamber 130 to diffuse more evenly through and over the wick by exploiting a Coanda effect. The Coanda effect causes the gas flow to attach to nearby surfaces and to therefore follow the curved radius 104a along the external wall 133 of the wick chamber 130 so that the gas is dispersed more evenly across the wick 131 in the wick chamber 130. The humidification device 100 may comprise a curved radius gas inlet to the fluid chamber 120, the wick chamber 130, or both. FIG. 14B shows a generic curved radius gas inlet 104 that may be used in a fluid chamber 120, for example.

Figure 15:
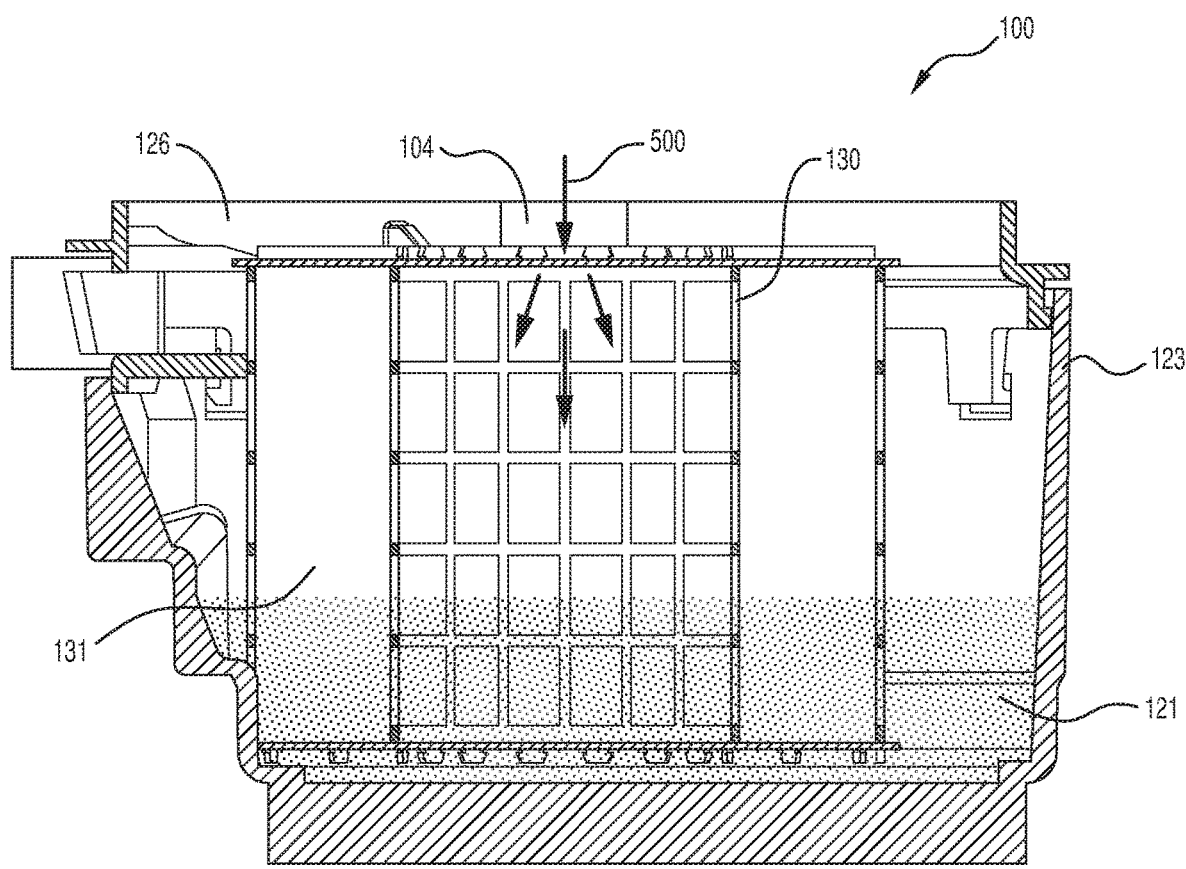
FIG. 15 is a cross-sectional side view of one form of fluid chamber containing a wick chamber and wick and having a gas inlet at the top of the fluid chamber.
Figure 16A:
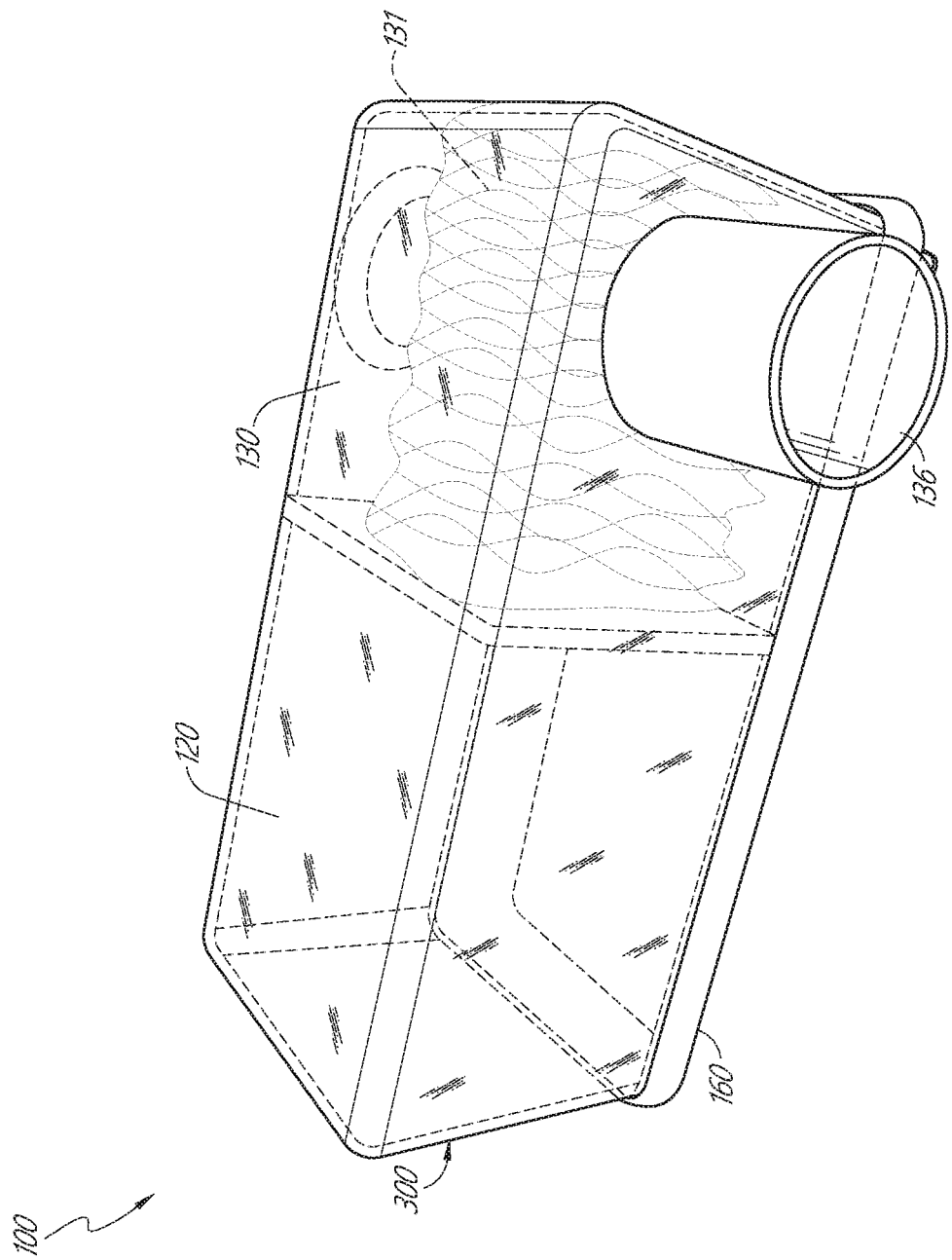
FIG. 16A is a front perspective view of another form of humidification device.
Figure 16B:
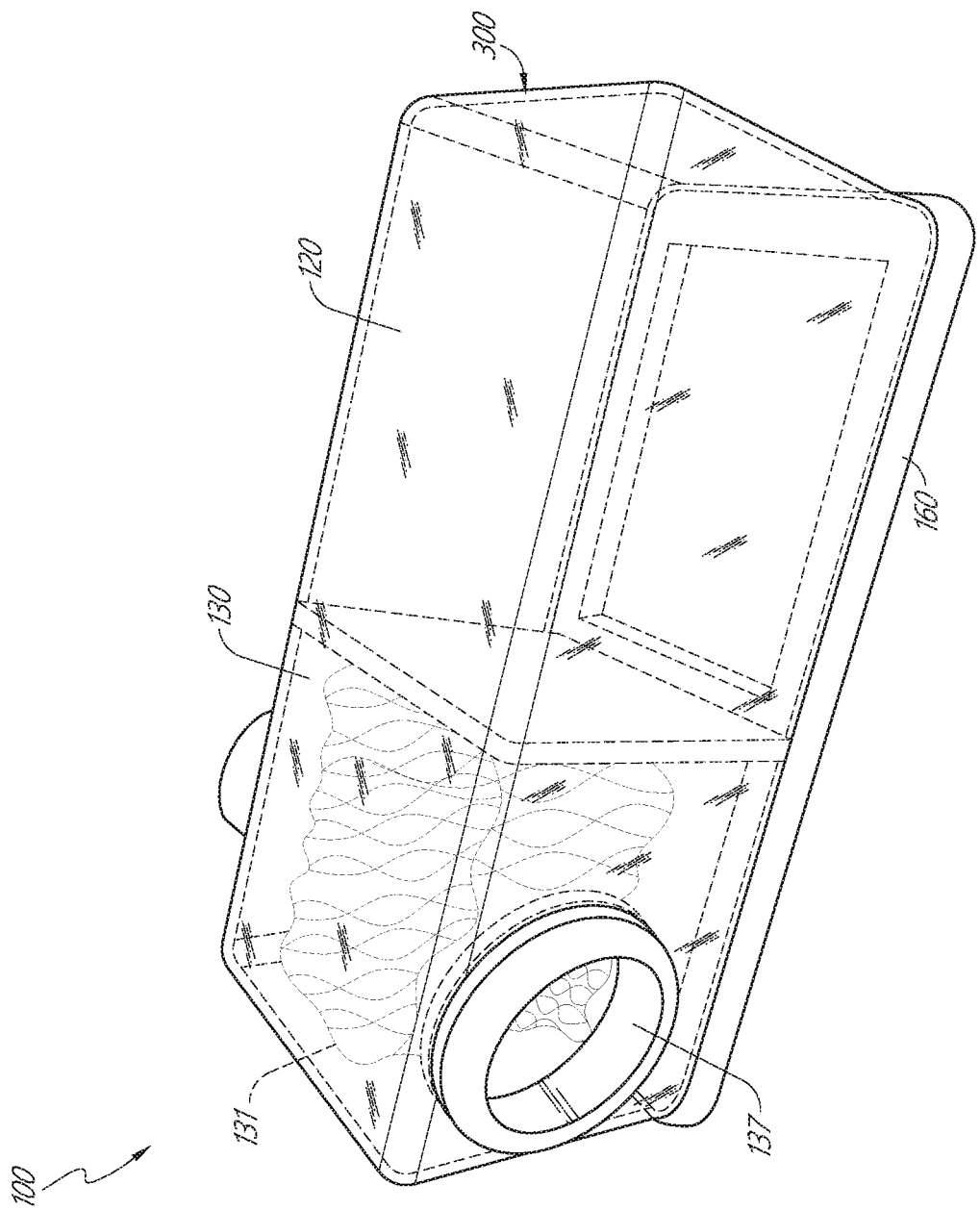
FIG. 16B is a rear perspective view of the humidification device of FIG. 16A.
Figure 17A:
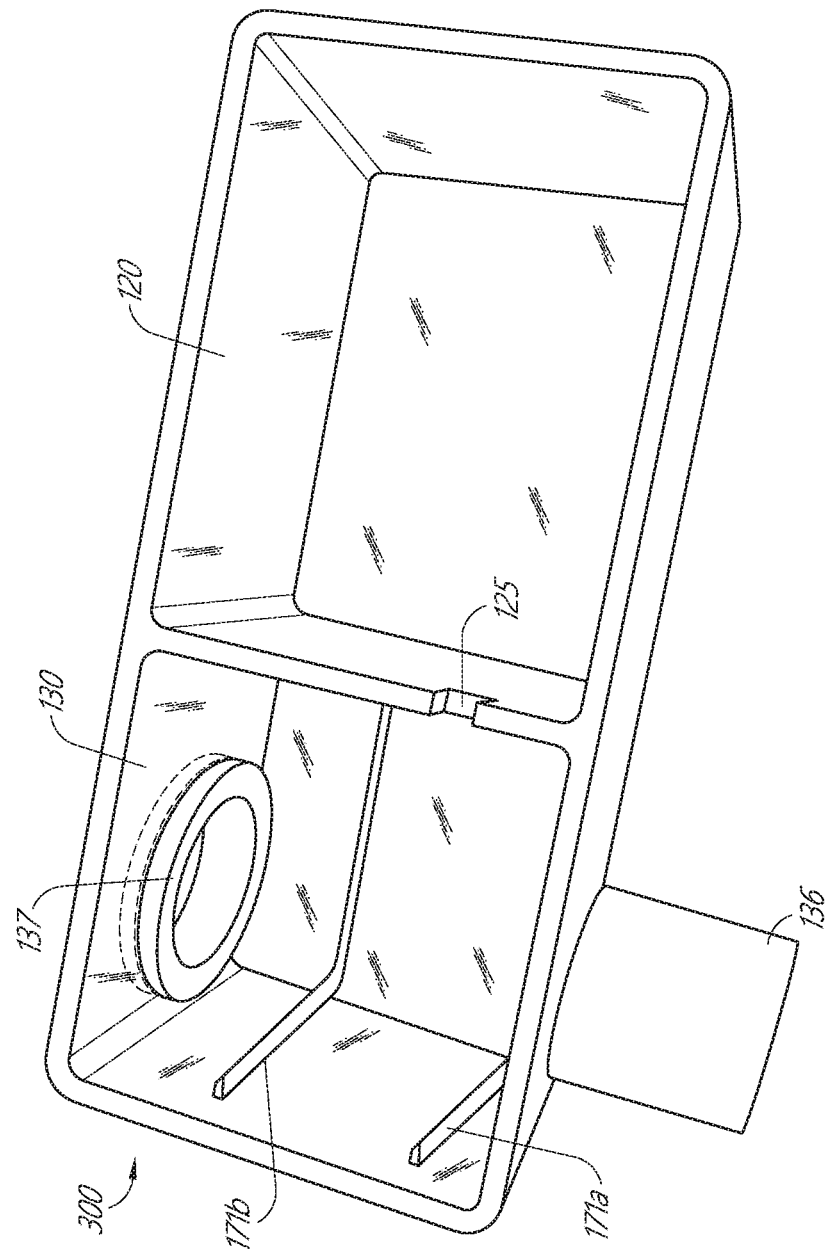
FIG. 17A is a bottom perspective view of the housing of the humidification device of FIG. 16A.
Figure 17B:
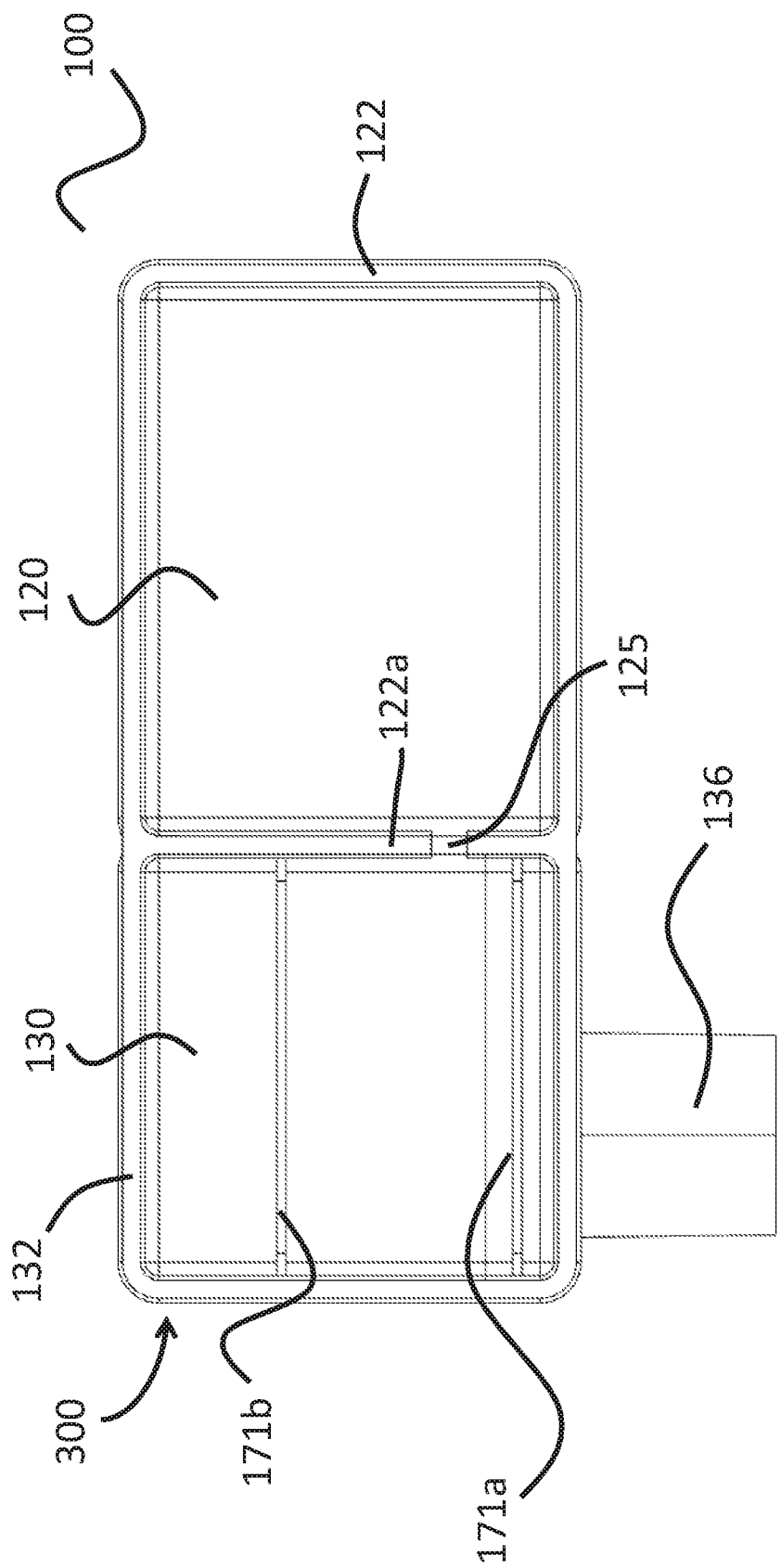
FIG. 17B is a bottom view of the housing of the humidification device of FIG. 16A.

In another form, as shown in FIG. 15, the fluid chamber inlet 104 may be located on the top of the fluid chamber, such as through the fluid chamber lid 126. Gas flow is directed from the fluid chamber inlet 104 to the wick chamber 130. The base 134 of the wick chamber and therefore the bottom of the wick 131 lies beneath the fluid level in the fluid chamber 120. Gas flow entering the fluid chamber 120 is dispersed by the fluid 121 in the chamber 120, causing the gas to flow more evenly across the exposed surface area of the wick 131, particularly the interior surface of the wall(s) defining the hollow region of the wick 131, where the wick includes a hollow region, such as where the wick is a tubular wick 131.

In another form, the fluid chamber inlet 104 may have a substantially frustoconical shape having an enlarged diameter at the fluid reservoir end of the gas inlet 104 so that the wall(s) of the gas inlet 104 flare outwardly as the gas inlet 104 opens into the fluid chamber 120. In this configuration, gas flowing through the inlet 104 may be caused to disperse through the chamber 120 by the frustoconical shape of the gas inlet 104.

In any form, the gas inlet 104 may comprise a diffuser 140, as discussed above, such as a louvre diffuser, grille, fabric diffuser, or any other suitable system for diffusing gas flow through the gas inlet.

Another form of wick humidifier or humidification device 100 is shown in FIGS. 16A to 21. Although all forms of wick humidifier shown and disclosed in this specification may be configured to be portable, the humidifier shown in FIGS. 16A to 21 may be particularly suitable as a portable humidifier/humidification device. In this form, the humidification device 100 comprises a housing 300 comprising a wick chamber 130 and a fluid chamber 120. The fluid chamber 120 is preferably located immediately adjacent to the wick chamber 130, but may be spaced from the wick chamber in alternative embodiments. The wick chamber 130 is configured to contain a wick 131. The fluid chamber 120 is configured to contain fluid 121 that is fed to the wick chamber 130 through a fluid flow path 150 connecting the fluid chamber 120 to the wick chamber 130. The fluid chamber 120 and wick chamber 130 may each comprise an opening 170 to allow a person to access the fluid 121 and wick 131 respectively. The humidification device 100 may also comprise at least one lid. Preferably, the lid comprises or consists of a seal 160 configured to cover or seal across the openings of both the fluid chamber 120 and wick chamber 130. However, in other forms, the device 100 may comprise a first lid to cover or seal across the opening of the fluid chamber 120 and a second lid to cover or seal across the opening of the wick chamber.

The wick chamber 130 comprises a gas inlet 136, through which gas can enter the chamber and pass across the wick 131, and a gas outlet 137 through which humidified gas can exit the wick chamber 130 for delivery to a patient. In one form, the gas inlet 136 is formed in a front wall of the wick chamber 130 and the gas outlet 137 is formed in a rear wall of the wick chamber 130. The fluid chamber gas outlet 137 may be positioned substantially opposite the wick chamber gas inlet 136.

The wick 131 may be substantially planar (two-dimensional) or a solid (three-dimensional) form. In other words, it is not necessary for the wick to comprise a hollow interior.

In one form, the wick chamber 130 may comprise one or more guides 171 to locate the wick 131 at a distance from the gas inlet 136 and/or gas outlet 137. For example, as shown in FIGS. 16A to 17B, the wick chamber 130 may comprise a first guide 171a to space the wick 131 at a distance from the gas inlet 136, and a second guide 171b to space the wick 131 at a distance from the gas outlet 137. Optionally, the first guide 171a spaces the wick 131 at a distance of approximately 2 mm from the gas inlet 136. The distance between the rear of the wick 131 and the gas outlet 137 is preferably at least 4 mm.

Spacing the wick 131 away from the gas inlet 136 produces a plenum in front of the wick 131 that helps to equalise pressure at the inlet 136 side of the wick 131 and to disperse gas more evenly across the wick 131. Spacing the wick 131 at an appropriate distance away from the gas outlet 137 reduces the risk that the surface tension of the fluid 121 may bridge the gap between the wick 131 and the wall of the wick chamber 130 in which the gas outlet 137 is located.

This configuration may also reduce the risk that fluid 121 from the wick 131 will be blown through the gas outlet 137 to the patient.

In the embodiment shown in FIGS. 16A to 17B, gas from a gas generator 110 is blown through the gas inlet 136 and across the surface of the wick 131 facing the inlet 136 (the facing surface). As the gas passes through the moist wick 131, the gas is humidified before exiting the wick chamber 130 through the gas outlet 137.

The wick chamber 130 is configured to hold at least some fluid 121 in which the bottom portion of the wick 131 sits, so that the fluid 121 moves up through the wick 131 under capillary action. In one form, the wick chamber 130 comprises one or more surrounding external walls 133 and a roof or lid 135 that meets with upper edges of the wick chamber walls 133. In one form, one of the walls 133 of the wick chamber 130 or the lid 135 of the wick chamber 130 may be removable, or may comprise a closeable access opening through which the wick 131 can be inserted and from which the wick may be removed from the wick chamber 130. In another form, the bottom of the wick chamber 130 may be removable to form an access opening or may comprise a base attached to the wall(s) 133 and having a closeable access opening through which the wick 131 can be inserted and removed from the wick chamber 130.

The fluid chamber 120 comprises surrounding walls 122 and a roof or lid 126 that meets with upper edges of the surrounding fluid chamber walls 122. In one form, the lid 126 of the fluid chamber 120 may be removable or may comprise a closeable access opening to allow access to the fluid chamber 120 so that fluid 121 can be added to and removed from the fluid chamber. In another form, the bottom of the fluid chamber 120 may be removable or may comprise a base with a closeable access opening through which fluid 121 can be added to and removed from the fluid chamber 120. In one form, a pump may be used to supply fluid to the fluid chamber 120 through an access opening at any suitable location in the fluid chamber 120.

Optionally, one or more walls 122 of the fluid chamber 120 may comprise one or more fluid level indicators to indicate to a user the optimum maximum and/or minimum fluid level at which the humidification device should operate.

In one configuration, the wick chamber 130 and fluid chamber 120 are adjacent and share a wall, as shown in FIGS. 16A to 17B.

The shared wall 122a may comprise an opening, such as a fluid channel 125, that forms a fluid flow path 150 through which fluid 121 may flow from the fluid chamber 120 to the wick chamber 130. Fluid 121 from the fluid chamber 120 pools in the bottom of the wick chamber 130 to wet the wick 131.

In one form, the humidification device 100 comprises a detachable base 160 that is configured to seal across an opening at the bottom of both the fluid chamber 120 and the wick chamber 130. In this configuration, it is possible to access both the fluid chamber 120 and the wick chamber 130 by turning the device 100 upside down and removing the base 160. The fluid chamber 120 may be filled and the wick 131 may be replaced before the base 160 is attached to bottom edges of the walls of the housing 300 (such as the fluid chamber walls 122 and wick chamber walls 133) to form a seal that prevents fluid 121 from escaping through the base 160. The humidification device 100 is then turned to its upright position, ready for use.

In one form, the base 160 comprises one or more guides 171 to locate the wick at a desired distance from the gas inlet 136 and gas outlet 137. For example, the base 160 may comprise a first guide 171*a* for spacing the wick away from the gas inlet 136 and a second guide 171*b* for spacing the wick 131 away from the gas outlet 137.

Figure 18B:
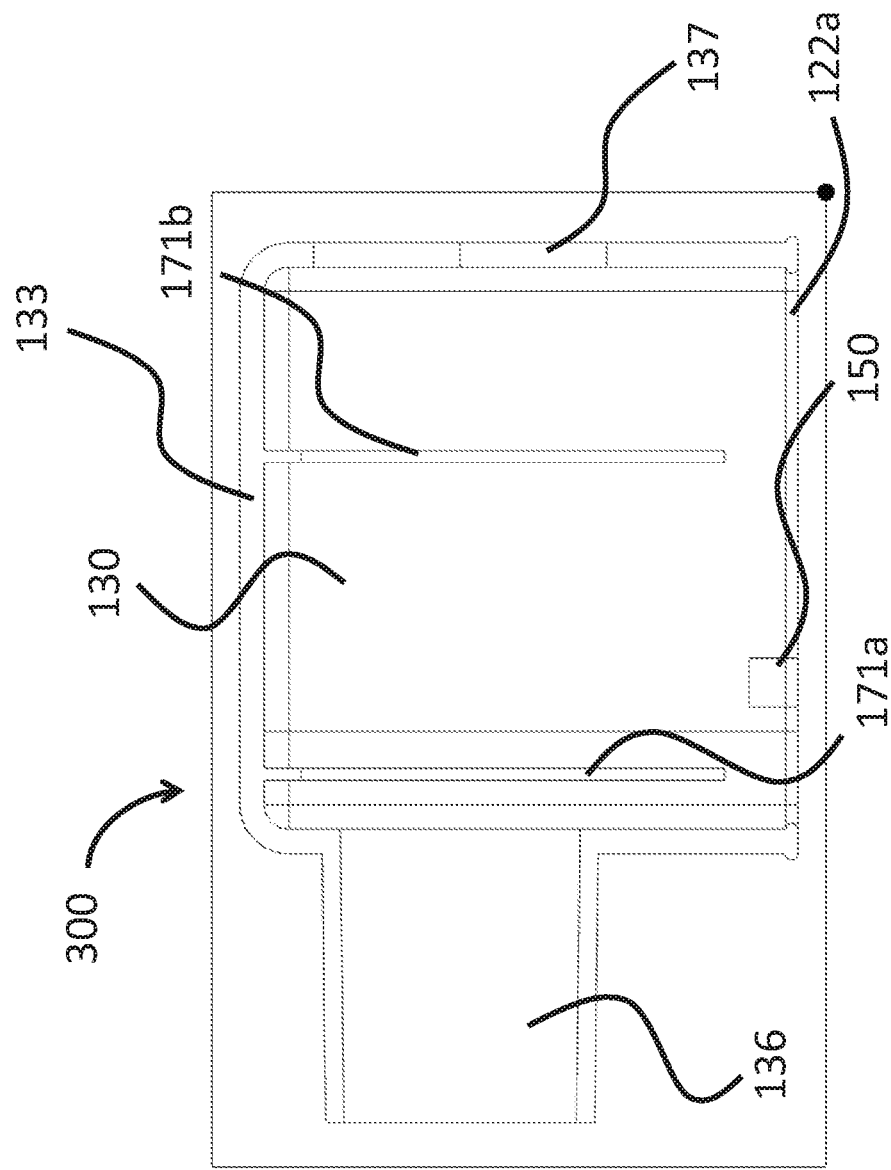
FIG. 18B is a cross-sectional side view of the housing of the humidification device of FIG. 16A.

In one form, the base 160 may comprise a retaining channel or groove 161 at or near its perimeter. The groove 161 may be configured to receive bottom edges of the surrounding walls 122, 133 of the fluid chamber and wick chamber. In one form, as shown in FIG. 18A, the bottom edges of the chamber walls 122, 133 comprise a rim 310 configured to engage with the groove 161 of the base 160 to form a fluid tight seal.

The base 160 may also comprise a partition channel or groove 162 that extends across the base. The partition groove 162 is positioned to at least partially receive the bottom edge of the shared wall 122*a* of the fluid chamber 120 and wick chamber 130.

Figure 19:
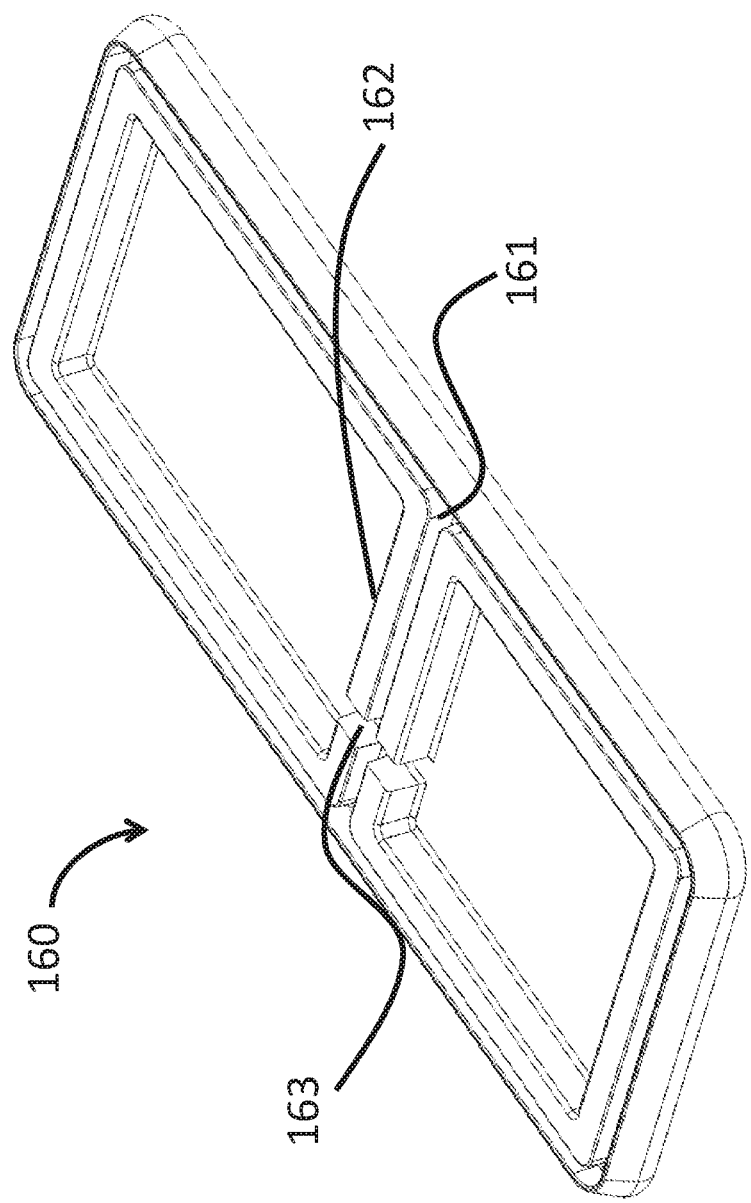
FIG. 19 is a perspective view of one form of base for the humidification device of FIG. 16A.

In one form, as shown in FIG. 19, the partition groove 162 comprises an opening, such as a fluid channel 163, that forms a fluid flow path 150 between the fluid chamber 120 and the wick chamber 130. In this configuration, fluid 121 from the fluid chamber 120 may be fed through the fluid channel 163 to the wick chamber 130 where the fluid 121 pools at the base of the wick chamber 130 and wets the wick 131 sitting on the base of the wick chamber 130.

In one form, both the shared wall 122 of the fluid and wick chambers 120, 130 and the partition groove 162 of the base 160 comprise a fluid channel forming a fluid flow path 150. In this form, the base 160 is attached to the humidification device housing 300 so that the fluid channel 163 of the base substantially aligns with the fluid channel 125 of the shared wall 122 of the housing 300 to allow fluid to flow from the fluid chamber 120 to the wick chamber 130.

Figure 20:
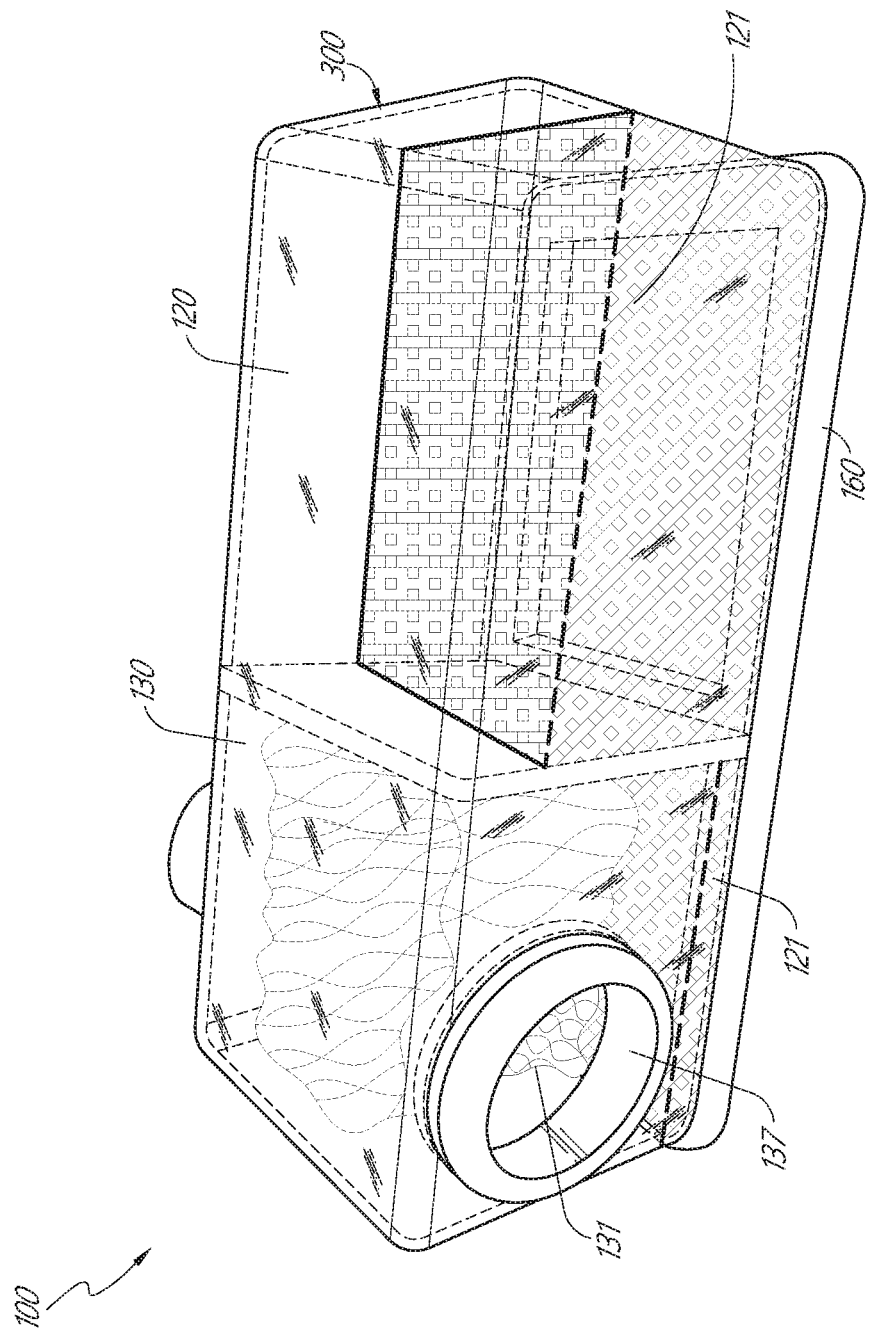
FIG. 20 is a rear perspective view of the humidification device of FIG. 16A filled with fluid.
Figure 21:
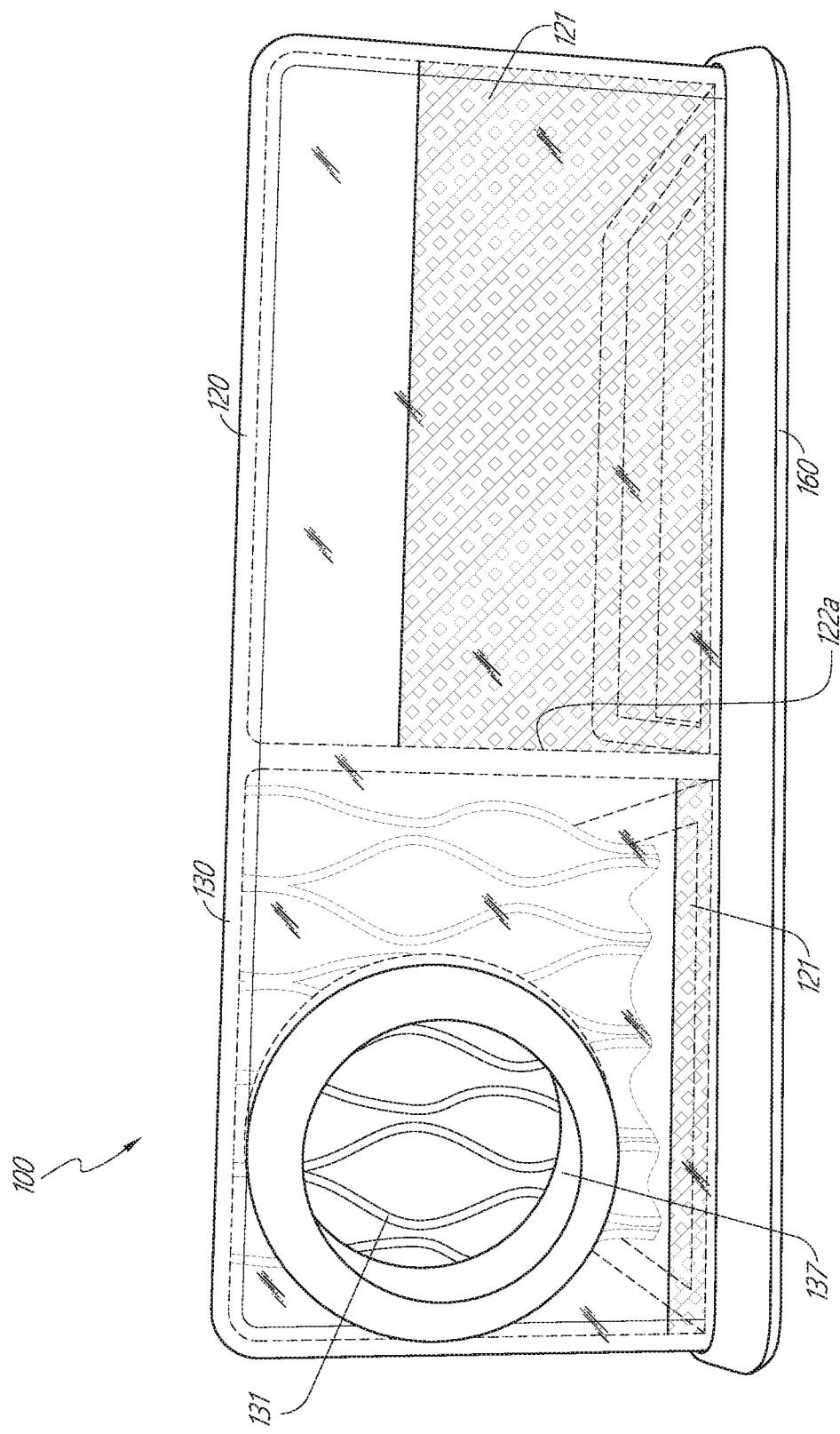
FIG. 21 is a rear view of the humidification device of FIG. 20.
Figure 22:
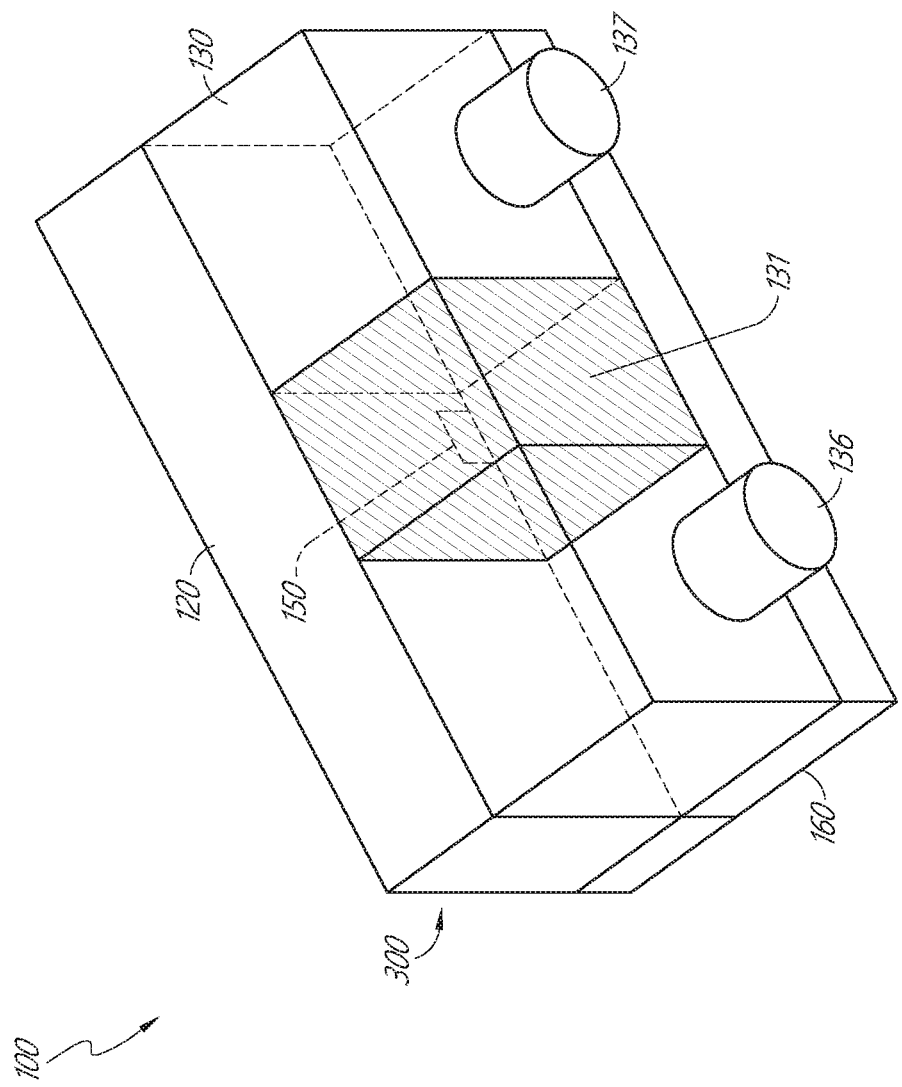
FIG. 22 is a schematic perspective view of another form of humidification device.
Figure 23:
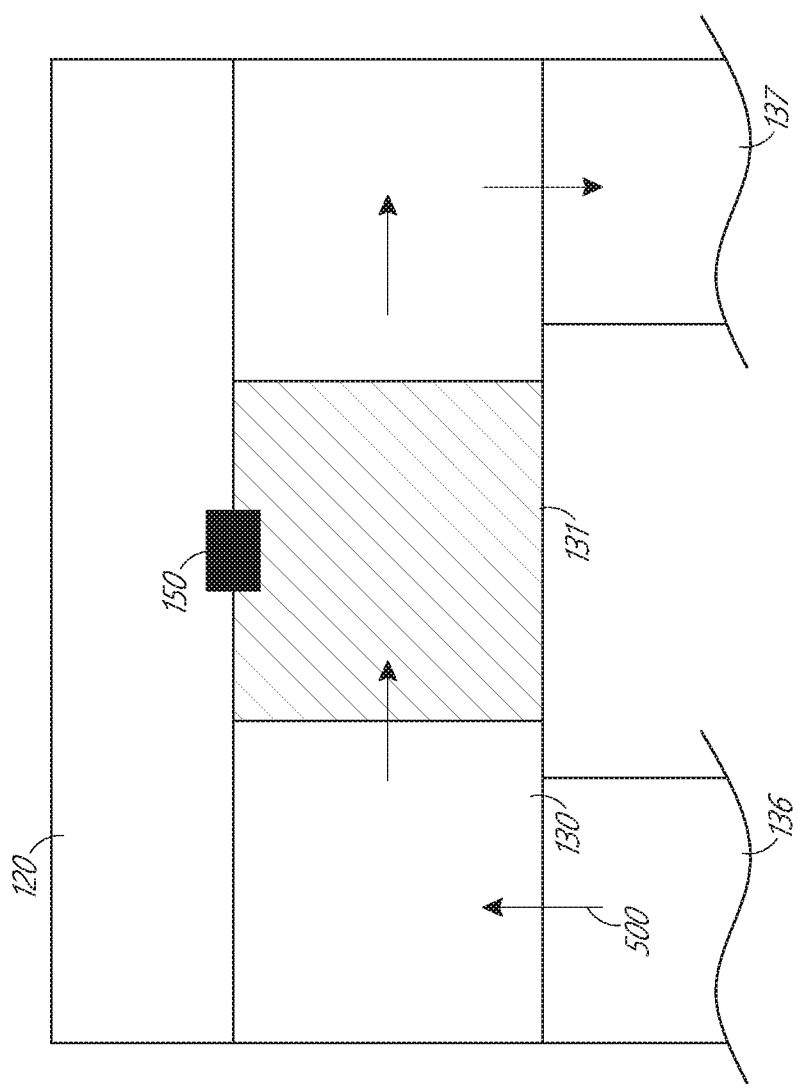
FIG. 23 is a schematic top view of the humidification device of FIG. 22.

FIGS. 20 and 21 show one form of humidification device 100 comprising adjacent wick and fluid chambers 130, 120 and in which the fluid chamber 120 contains water. The wick chamber 130 has a first volume that is dimensioned to contain a wick 131. In the illustrated embodiment, the volume of the wick chamber 130 is 89 cm$^3$. The fluid chamber 120 has a second volume that is dimensioned to hold a sufficient volume of fluid 121 to humidify gas for at least one full night (for about 8 to 10 hours). In the illustrated embodiment, the volume of the fluid chamber 120 is 115 cm$^3$. In this configuration therefore, the fluid chamber 120 has a larger volume than the wick chamber 130. One possible ratio between the volume of the wick chamber 130 and the fluid chamber 120 is 89:115 or 1:1.29. However, other ratios may also be suitable.

In use, fluid from the fluid chamber 120 will flow to the wick chamber 130 through the fluid flow path 150 until a point of equilibrium is met. This point of equilibrium is typically met when the level of fluid 121 in the wick chamber 130 lies just above the height of the fluid channel 125, 163. This is the maximum fluid level of the wick chamber 130. Therefore, the fluid level in the wick chamber 130 is typically less than the fluid level in the fluid chamber 120.

The fluid 121 in the wick chamber 130 soaks into the bottom of the wick 131 and moves up the wick 131 under capillary action to dampen the wick 131. The fluid level in the wick chamber 130 lowers below the maximum height of the fluid channel 125, 163 as fluid is soaked up by the wick 131. Gas from the wick chamber 130 may then pass through the fluid channel 125, 163 and into the fluid chamber 120 to displace the fluid 121 that has left the fluid chamber 120. Gas flowing across the wick 131 is humidified by the wick 131. As the wick 131 humidifies gas, the wick 131 soaks up more fluid to replace the fluid that humidified the gas. Therefore, fluid continues to flow from the fluid chamber 120 to the wick chamber 130 until the point of equilibrium is reached again. Therefore, the wick 131 is able to hold fluid in the wick chamber 130 but the wick chamber is prevented from flooding.

One advantage of maintaining a substantially constant fluid level in the wick chamber is that a substantially constant surface area of the wick is available for gas 500 to pass across. This provides improved control of the humidification output of the humidification device. Contrast this with other wick humidifiers where the exposed surface area of the wick increases over the course of the therapy session as more fluid is evaporated and transferred to the gas passing across the wick.

Another advantage of maintaining a substantially constant fluid level in the wick chamber is that it allows for a substantially known volume of wick material to be used.

Furthermore, by providing a low level of fluid in the wick chamber, the overall volume of the humidification device may be minimised and the device may be more tolerant to being tilted at an angle, such as during transportation, without fluid flowing out the inlet or the outlet.

The humidification device 100 may be configured to further improve the dispersion of gas passing across the wick by increasing the gas inlet opening 136 to the wick chamber 130 relative to the facing surface of the wick 131.

The gas inlet 136 may have an opening in a wall 133 of the wick chamber 130. The gas inlet opening 136 has an inlet surface area (ISA). Where the gas inlet 136 is cylindrical and the inlet opening is circular, the ISA is the surface area of a circle formed with a centre at the cylindrical axis of the gas inlet 136. The facing surface of the wick 131 also has a surface area (WSA), which is the surface area of a plane on the front of the wick, facing the gas inlet 136. Increased dispersion of gas flow across the wick 131 can be achieved by increasing the ratio of the ISA to the WSA. For example, maximum dispersion can be achieved with ISA:WSA of 1:1. The configuration shown in FIGS. 20 and 21 has an ISA:WSA ratio of approximately 2.84:18 or approximately 1:6.3. In other embodiments, this ratio may differ. For example, the ISA:WSA ratio could be 1:4.

FIGS. 22 to 35D show another form of humidification device 100 configured to disperse gas flow substantially evenly across a wick 131 by controlling gas flow within the device 100 or system 200 using a control system or controller. In one form, the control system/controller comprises one or more control valves to control gas flow within the humidification device 100 or system 200. This embodiment operates in substantially the same manner as that illustrated in FIGS. 16A to 21, but is configured differently. In the humidification device 100 shown in FIGS. 22 to 35D, a bypass channel 190 is provided so that a portion of gas flow can be directed across the wick 131 and a portion of gas flow can be directed to bypass the wick 131 and instead flow along the bypass channel 190 before the gas portions then meet together and are delivered to a patient. This configuration allows the gas flow path to be controlled in order to control the humidity of gas delivered to a patient. Any of the embodiments shown in FIGS. 1A to 21 may also be configured to comprise a bypass channel 170.

Figure 24:
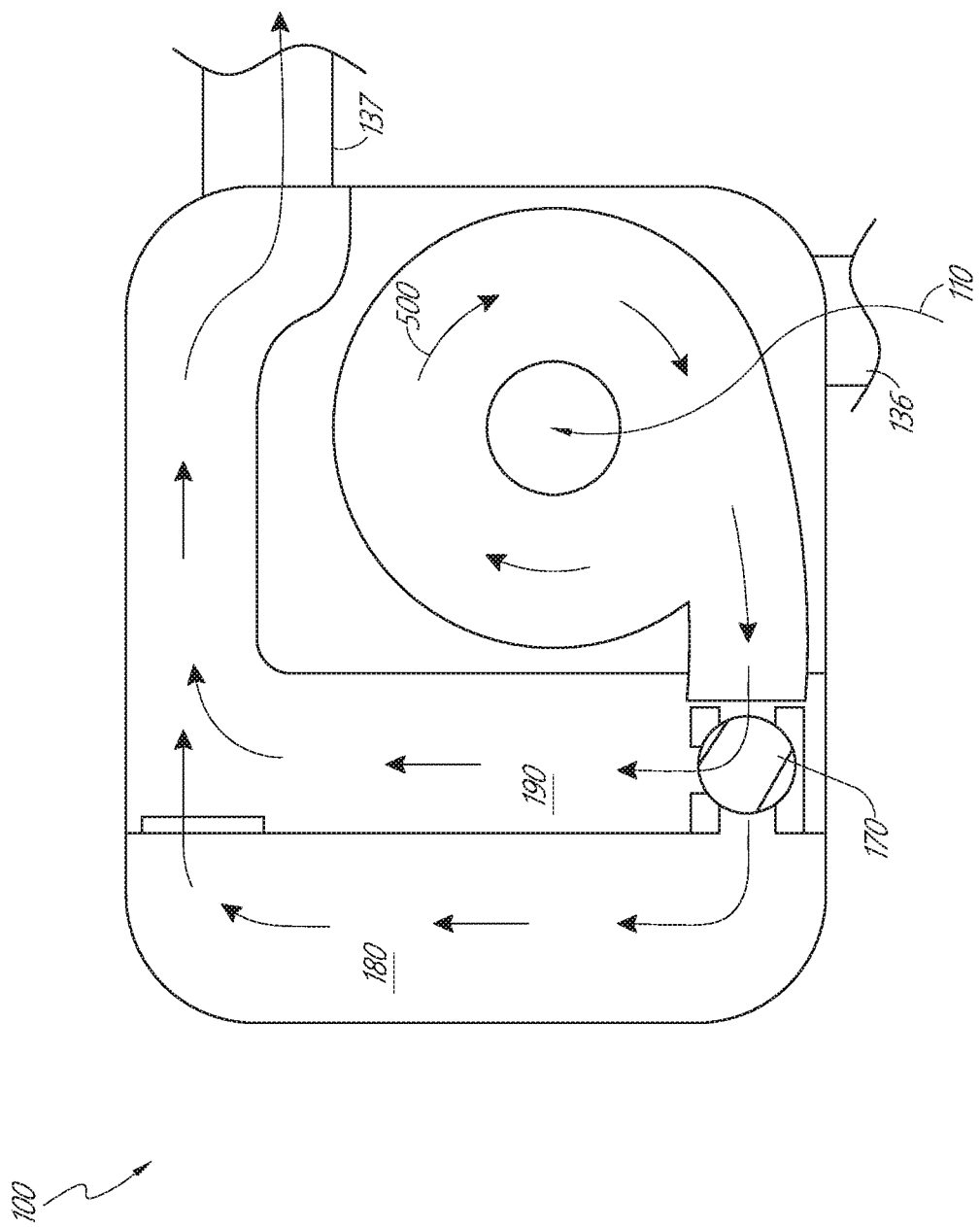
FIG. 24 is a schematic cross-sectional top view of one form of humidification device or system comprising a flow generator attached to a humidifier and having dual flow paths for gas flow.

In one form, as shown in FIG. 24, a humidification device 100 or system 200 comprises a flow generator 110 having a gas inlet 111 and a gas outlet 112, a control system or controller, to control gas flow, comprising at least one control valve 170, a first gas channel 180, and a second gas channel 190. The control system with valves may be used in the humidification devices of FIGS. 1-15 and FIGS. 16-23. The first gas channel 180 may be configured to direct gas to a humidification module 400 and the second gas channel 190 may be a bypass channel to allow gas to bypass the humidification module 400. The control valve 170 may be configured to direct an amount of gas through the first channel 180, the second channel 190 or both. In one form, the control valve 170 may be configured to direct between 0% to 100% of gas to the first channel 180 or the second channel 190. For example, the control valve 170 may direct 70% of gas along the first channel 180 and 30% of gas along the second channel 190. In another example, the control valve 170 may direct 50% of gas along the first channel 180 and 50% of gas along the second channel 190.

In one form, the humidification device 100 or system 200 may comprise a variable diffusor located at the inlet of the first/humidification flow path/channel 180 that flows through the humidification module 400. The variable diffuser may act as both a valve and a diffusor. For example, the variable diffusor may be comprise multiple apertures, any one or more of which may be configured to be fully open, partially open, or closed. When in a first position, the variable diffuser can be in an open position, allowing air flow through the holes, acting simultaneously as a diffusor. When the variable diffusor is in a closed position, the diffuser may block gas flow through the humidification flow path. By using a variable diffusor as a valve, it may be possible to remove the need for a diffusor downstream. The variable diffuser arrangement may be similar to a salt shaker or the like having an upper surface comprising multiple apertures within a localised region, and a lower surface, located proximate to the upper surface but being only half the size of the upper surface and therefore covering only half of the upper surface. The upper surface may be rotated relative to the lower surface so that the lower surface: (a) covers one or more apertures to close those apertures; (b) partially covers one or more apertures so that these apertures are partially open; and/or does not cover one or more apertures so that these apertures are fully open.

The control valve 170 may be positioned at any suitable location within the humidification device 100.

Figure 25:
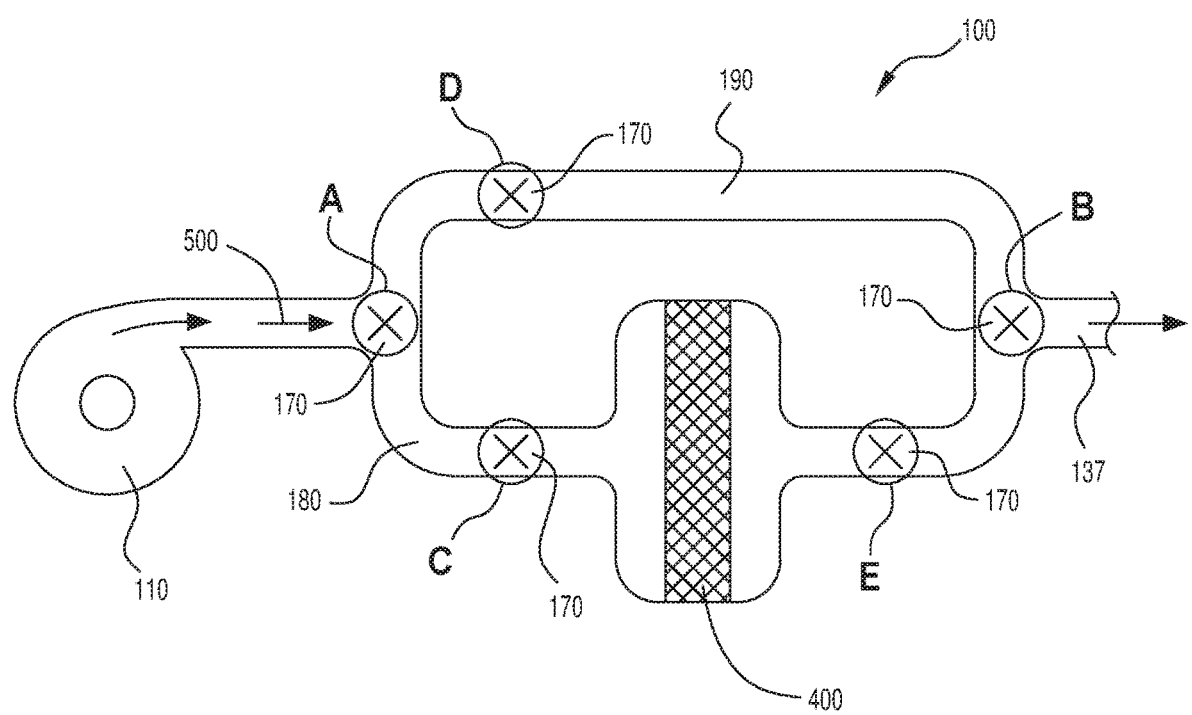
FIG. 25 is a schematic cross-sectional top view of one form of humidification device or system comprising a flow generator and a wick humidifier having two gas flow paths/gas channels and showing possible valve locations within the system.

FIG. 25 shows a simplified schematic representation of a humidification system 200 comprising a flow generator 110, a first gas channel 180, a second gas channel 190, and a humidification device or humidifier 100. FIG. 25 also illustrates several different locations in which one or more control valves 170 may be positioned to control gas flow through the first gas channel 180 and second gas channel 190. For example, a control valve 170 may be located at any of the positions A, B, C, D, or E depicted in FIG. 25.

A control valve 170 positioned at location A (which is the intersection between a gas outlet from the flow generator 110, the first gas channel 180 and the second gas channel 190), can be configured to direct between 0% to 100% of gas flow through the first channel 180 and through the second channel 190, or through a controlled combination of both channels 180, 190.

Similarly, a control valve 170 positioned at location B, where the first and second channels 180, 190 meet again at a gas outlet 105, may be configured to allow only gas from the first channel to pass through the valve 170 and out the gas outlet 105, or to allow only gas from the second channel to pass through the valve 170 and out the gas outlet 105, or to allow gas from both the first and second channels 180, 190 to pass through the valve 170 and out the gas outlet 105.

In another embodiment, a first control valve 170 may be positioned at location C in the first flow channel 180, prior to the humidifier, and a second control valve 170 may be positioned at location D in the second flow channel 190. Each of the control valves 170 at locations C and D may be fully open to allow gas 500 to flow freely through the valve 170, fully closed to prevent gas 500 from flowing through the valve 170, or partially open to restrict the amount of gas 500 passing through the valve 170. Valves 170 at locations C and D may be configured to open, close or partially open in order to direct 100% of gas 500 through the first channel 180 and through the humidifier, 100% of gas through the second channel 190 to bypass the humidifier, or to allow a portion of the total amount of gas 500 to pass through the first channel 180 and the remaining portion of gas 500 to pass through the second channel 190. In other words, valves C and D may be configured to control the amount of gas 500 flowing through the first and second channels 180, 190. The amount of gas 500 flowing through any one of the channels 180, 190 may be between 0% and 100% of the gas flow 500 produced by the flow generator 110. For example, the proportion of gas flow 500 between the first and second channels 180, 190 may be: (100%:0%); (90%:10%); (80%:20%); (70%:30%); (60%:40%); (50%:50%); (40%:60%); (30%:70%); (20%:80%); (10%:90%); (0%:100%).

In another form, instead of positioning a valve 170 prior to the humidifier at location C, a valve 170 may be positioned in the first channel 180 and after the humidifier at location E. In this location, the valve 170 would have similar effect to a valve 170 at location C.

Figure 26A:
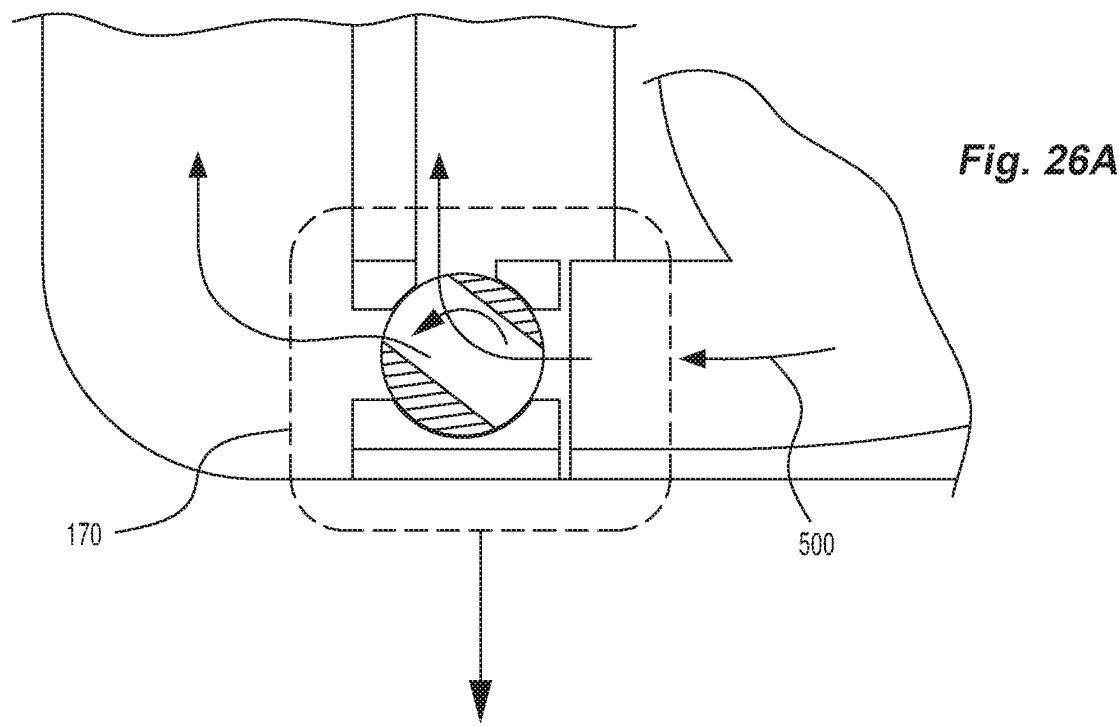
FIG. 26A is a schematic cross-sectional top view of a portion of a dual flow path humidification device or system having a control system comprising a ball valve positioned in a first orientation.
Figure 26B:
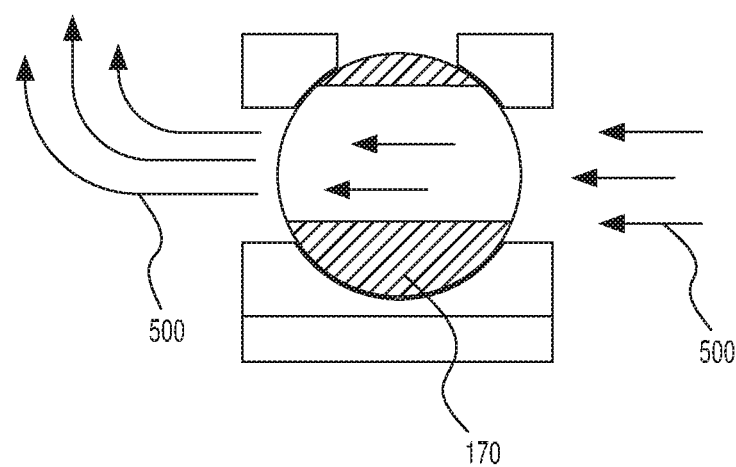
FIG. 26B is a schematic cross-sectional top view of the ball valve of FIG. 26A positioned in a second orientation in which gas is caused to flow to a first gas channel.
Figure 27A:
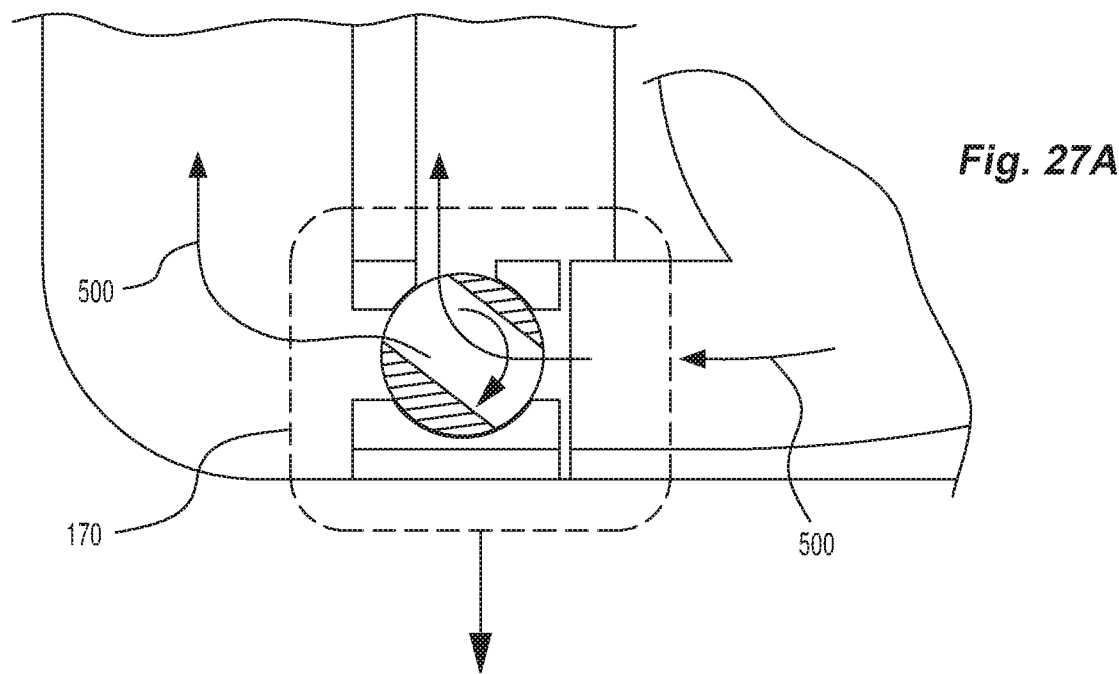
FIG. 27A is a schematic cross-sectional top view of a portion of a dual flow path humidification device or system having a ball valve positioned in the first orientation.
Figure 27B:
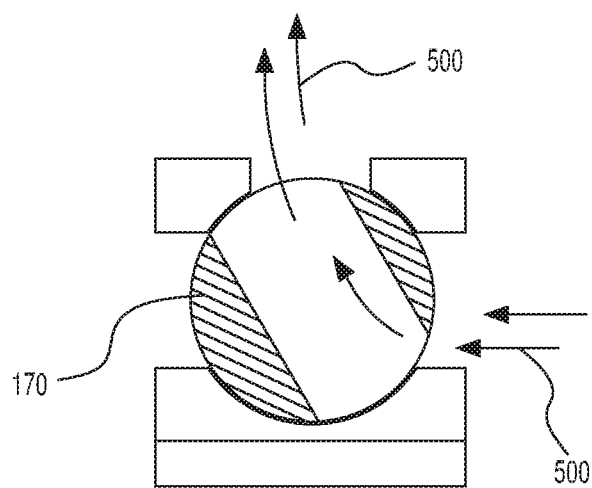
FIG. 27B is a schematic cross-sectional top view of the ball valve of FIG. 26A positioned in a third orientation in which gas is caused to flow to a second gas channel.
Figure 28A:
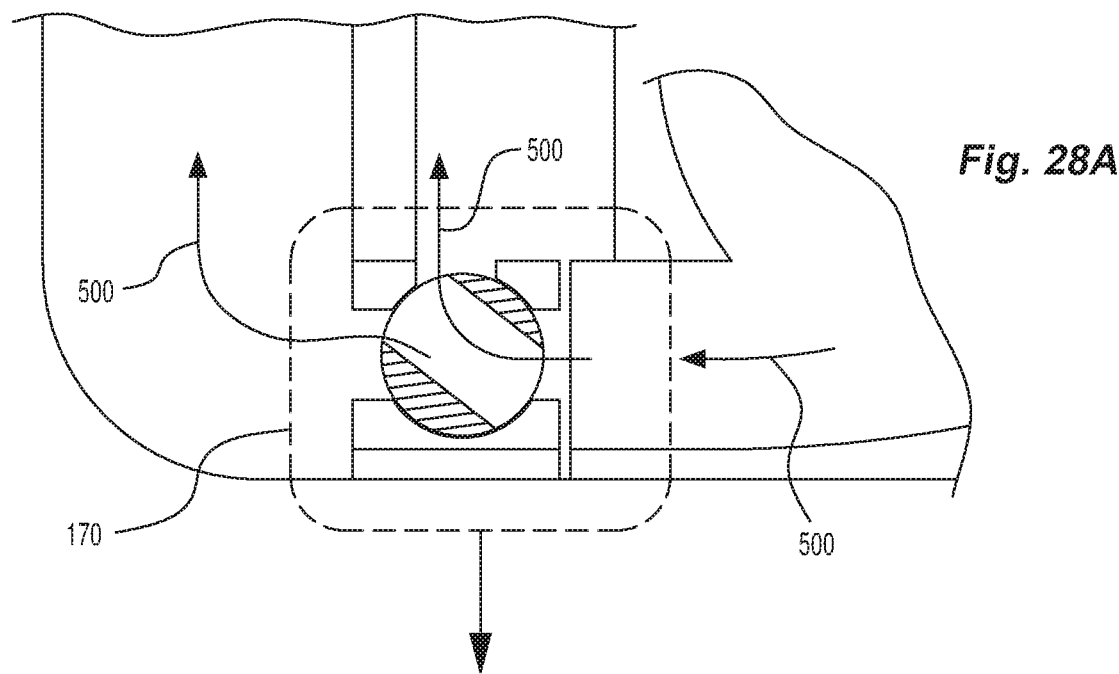
FIG. 28A is a schematic cross-sectional top view of a portion of a dual flow path humidification device or system having a ball valve positioned in the first orientation in which approximately 50% of gas flow is caused to flow through the first gas channel and approximately 50% of gas flow is caused to flow through the second gas channel.
Figure 28B:
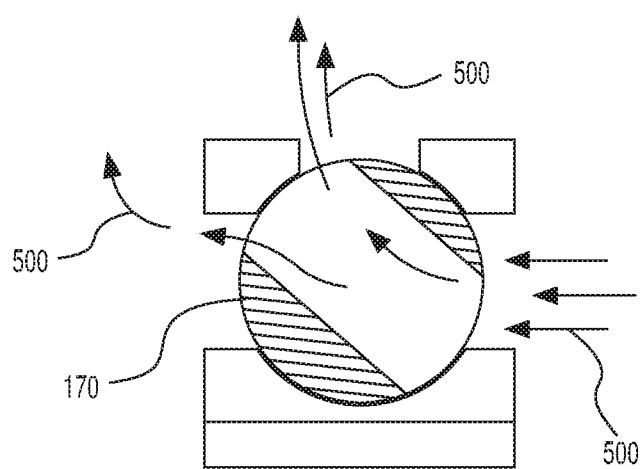
FIG. 28B is an enlarged schematic cross-sectional top view of the ball valve of FIG. 26A in a fourth orientation in which approximately 25% of gas flow is caused to flow through the first gas channel and approximately 75% of gas flow is caused to flow through the second gas channel.

The control valve 170 may be any suitable form of valve for controlling gas flow 500 through the humidification device 100. For example, the control valve may comprise a ball valve, gate valve, globe valve, butterfly valve, needle valve, or the like. In one form, as shown in FIGS. 26 to 28, the control valve 170 is a ball valve. The ball valve 170 may be rotated on its axis to direct gas flow to the first channel 180 or the second channel 190 or to direct an amount of gas 500 along each of the first and second gas channels 180, 190. FIGS. 26A and 26B show how the ball valve 170 can direct gas 500 along both gas channels 180, 190 and can then be rotated to direct gas along the first gas channel 180 only. Similarly, FIGS. 27A and 27B show how the ball valve 170 can direct gas along both gas channels 180, 190 and can then be rotated to direct gas 500 along the second gas channel 190 only. FIGS. 28A and 28B show how a ball valve 170 can be oriented to direct gas flow along both the first and second gas channels 180, 190. The valves 170 shown in FIGS. 26A to 28B are positioned at the control valve location shown in the humidification device 100 of FIG. 24.

The ball valve 170 may be manually, pneumatically or electrically actuated. If the ball valve is manually activated, it may be beneficial for the humidification device to include a position indicator, such as a gauge or scale that provides a user with an indication of the valve position (i.e. whether the valve is open, closed or partially open to the first channel and whether the valve is open, closed, or partially open to the second channel).

Figure 29A:
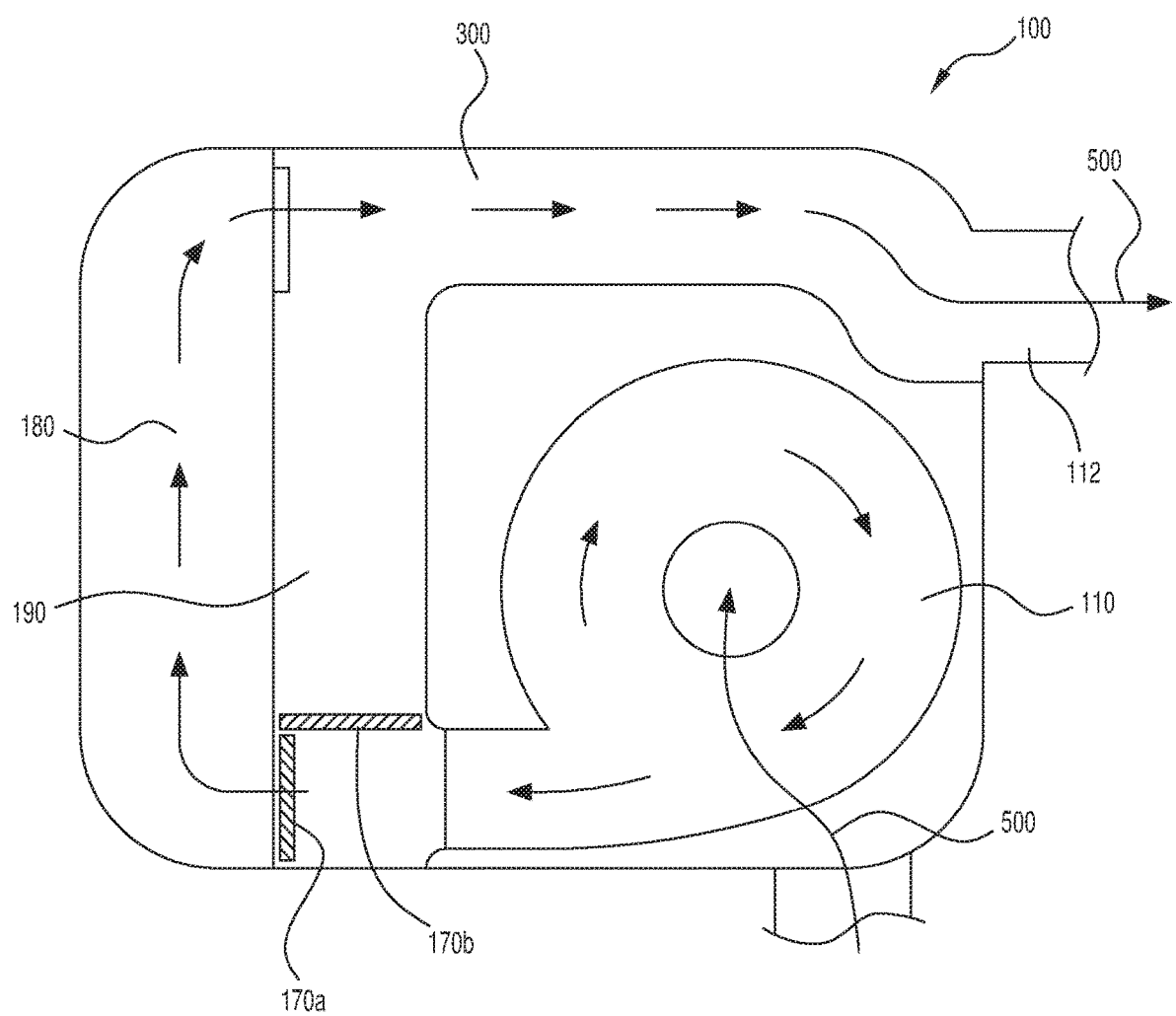
FIG. 29A is a schematic cross-sectional top view of one form of flow generator for a humidification device or system in which the flow generator comprises dual gate valves to direct gas flow along a first gas channel and/or a second gas channel.

In another embodiment, the control system may comprise at least one control valve 170 in the form of a gate valve, which may be fully open to allow gas to flow freely along a gas channel, closed to prevent gas flow along a gas channel, or partially open to restrict gas flow along a gas channel. For example, in one form, as shown in FIG. 29A, the control system comprises a first gate valve 170a, in or at the entrance to a first gas channel 180, and a second gate valve 170b in or at the entrance to a second gas channel 190. In this configuration, if 100% of gas from the gas generator 110 is to flow along the first gas channel 180 to be humidified, the first gate valve 170*a* is fully opened and the second gate valve 170*b* is closed. Conversely, if 100% of gas is to flow along the second gas channel 190 to bypass the humidification process, the second gate valve 170*b* is fully opened and the first gate valve 170*a* is closed. If the gas flow is to be split between the first and second gas channels 180, 190, both first and second gate valves 170*a*, 170*b* may be partially open. Again, the gate valves 170 may be manually or electronically actuated.

Figure 29B:
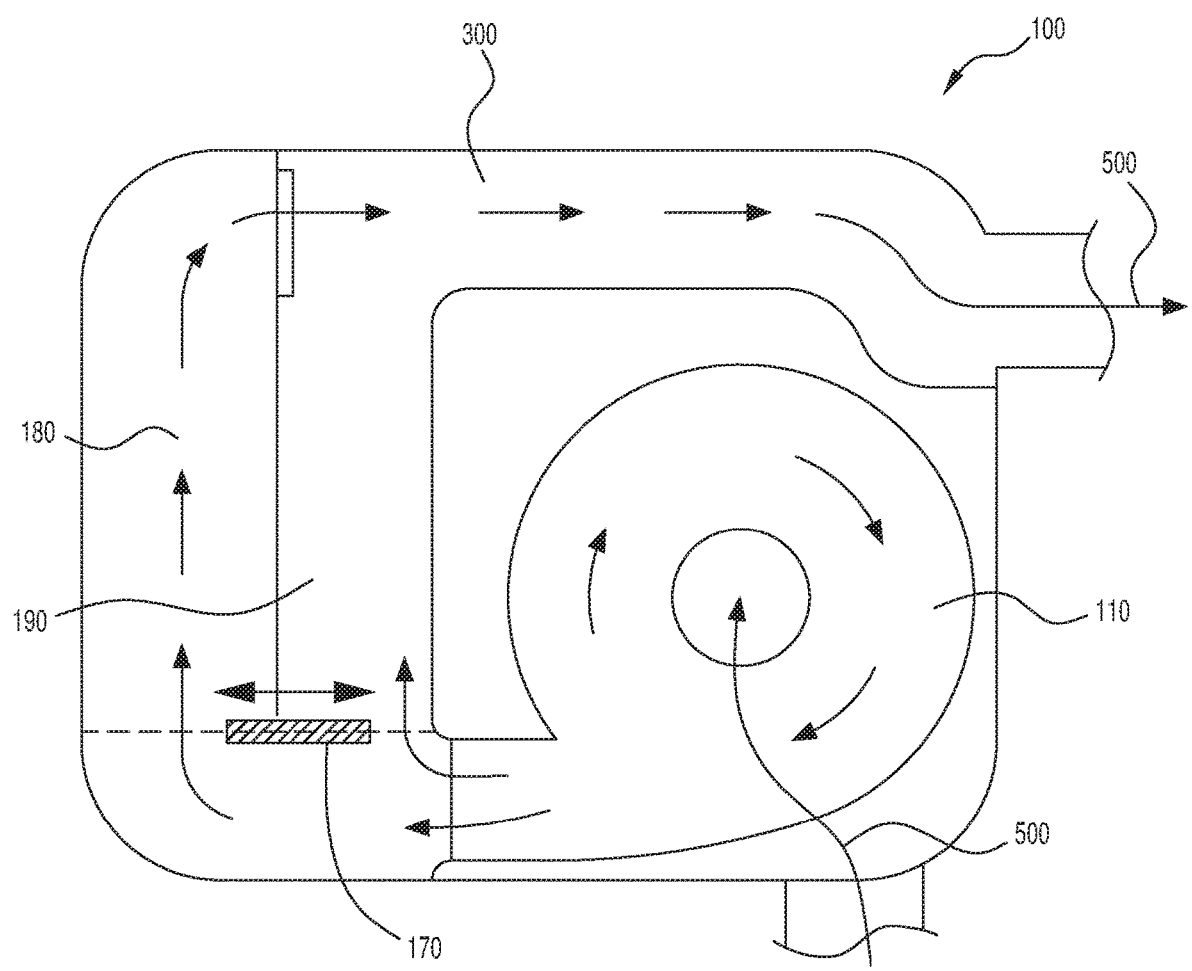
FIG. 29B is a schematic cross-sectional top view of another form of flow generator for a humidification device or system in which the flow generator comprises a single gate valve to direct gas flow along a first gas channel and/or a second gas channel.

In another form, as shown in FIG. 29B, gas flow is controlled by a single gate valve 170 that is movable between a first position, in which the first gas channel 180 is open, and a second position, in which the second gas channel 190 is open. This movement is indicated by the dashed line in FIG. 29B. In this configuration, a single control valve 170 may control and divide gas flow 500 between the two gas channels 180, 190, as opposed to needing two control valves. Again, the control valve may be electronically, pneumatically or manually actuated.

FIGS. 30A and 30B illustrate one form of gate valve 170 that may be used to open, close, or partially open access to a gas channel. When the gate of the gate valve 170 is lowered across a gas channel, as shown in FIG. 30A, the valve 170 is closed and access to the gas channel is blocked. When the gate is fully raised, as shown in FIG. 30B, access to the gas channel is open and unimpeded.

Figure 31:
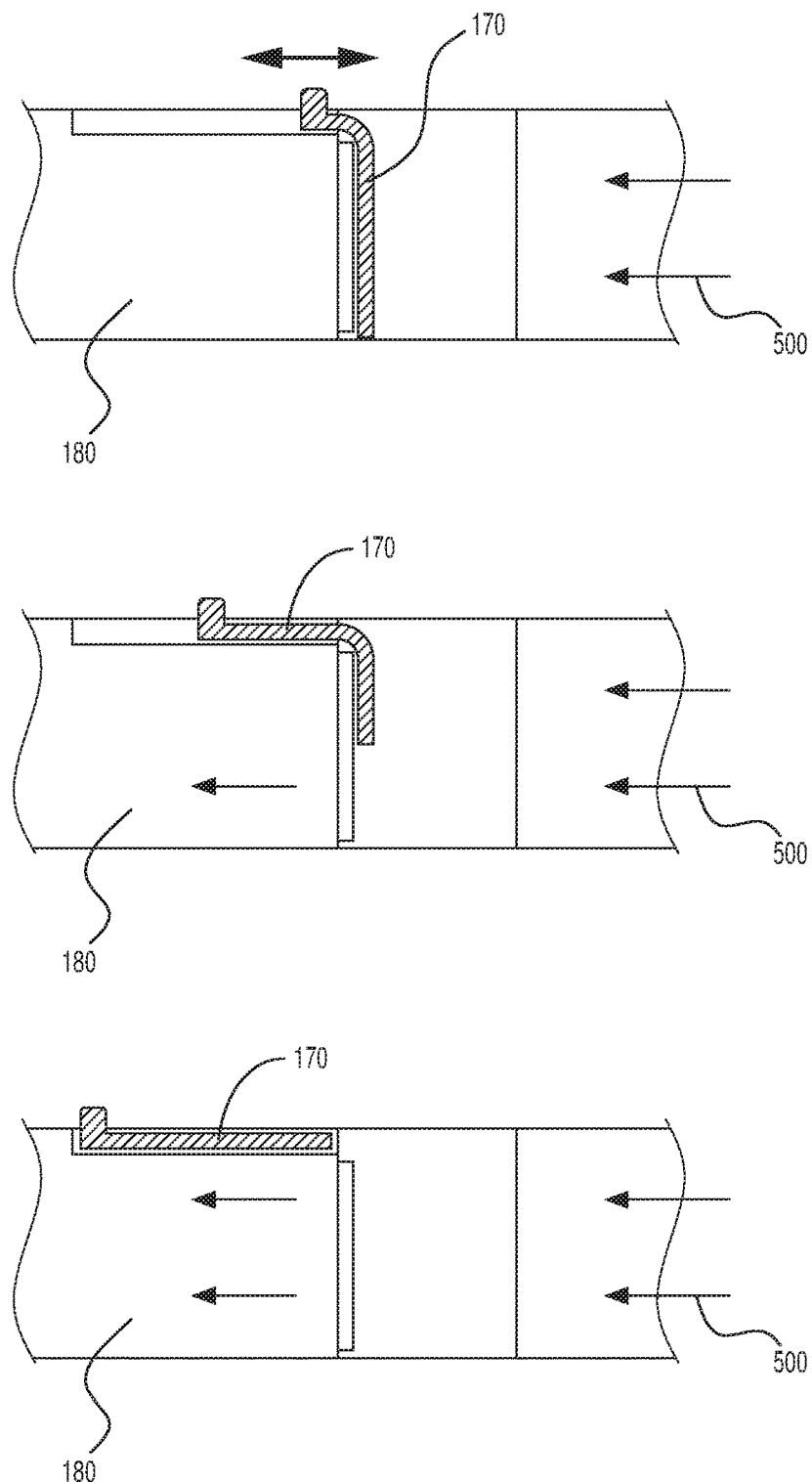
FIG. 31 is a schematic diagram illustrating movement of one form of flexible gate valve between closed, partially open, and open positions.

FIG. 31 shows another form of control valve 170 that may be used with the humidification device 100 or system 200. In this form, the control valve acts in a similar manner to the gate valve, but is formed of a flexible material that is able to:

close the gas channel by spanning the opening to the gas channel;

partially open the gas channel by being partially pulled up and over an upper portion of the gas channel so as to partially cover the gas channel opening; and fully open the gas channel by being completely pulled up over the upper portion of the gas channel to fully expose the gas channel opening.

In another form, the humidification device 100 or system 200 may comprise two flow generators 110. For example, the device 100 may comprise a first flow generator 110*a* to generate a first gas flow that is directed along a first flow path/channel 180 across the wick 131 of a wick humidifier, and a second flow generator 110*b* to generate a second gas flow that is directed along a second flow path/channel 190 that bypasses the humidifier. The first and second gas flows combine downstream, mixing together to form a single unified flow path 600. Optionally, the outlet of one or both flow generators may comprise a check valve to prevent backflow of air from the other flow generator.

The amount of gas 500 directed by each flow generator 110 may be tailored to control the humidity of the gas 500 delivered to a patient. For example, if half the maximum humidity of the wick humidifier is desired, the first flow generator 110*a* and the second flow generator 110*b* can deliver an equal amount of breathing gas to the unified flow path 600, so that half the gas 500 is humidified by the wick 131 and half is at ambient humidity.

Figure 32A:
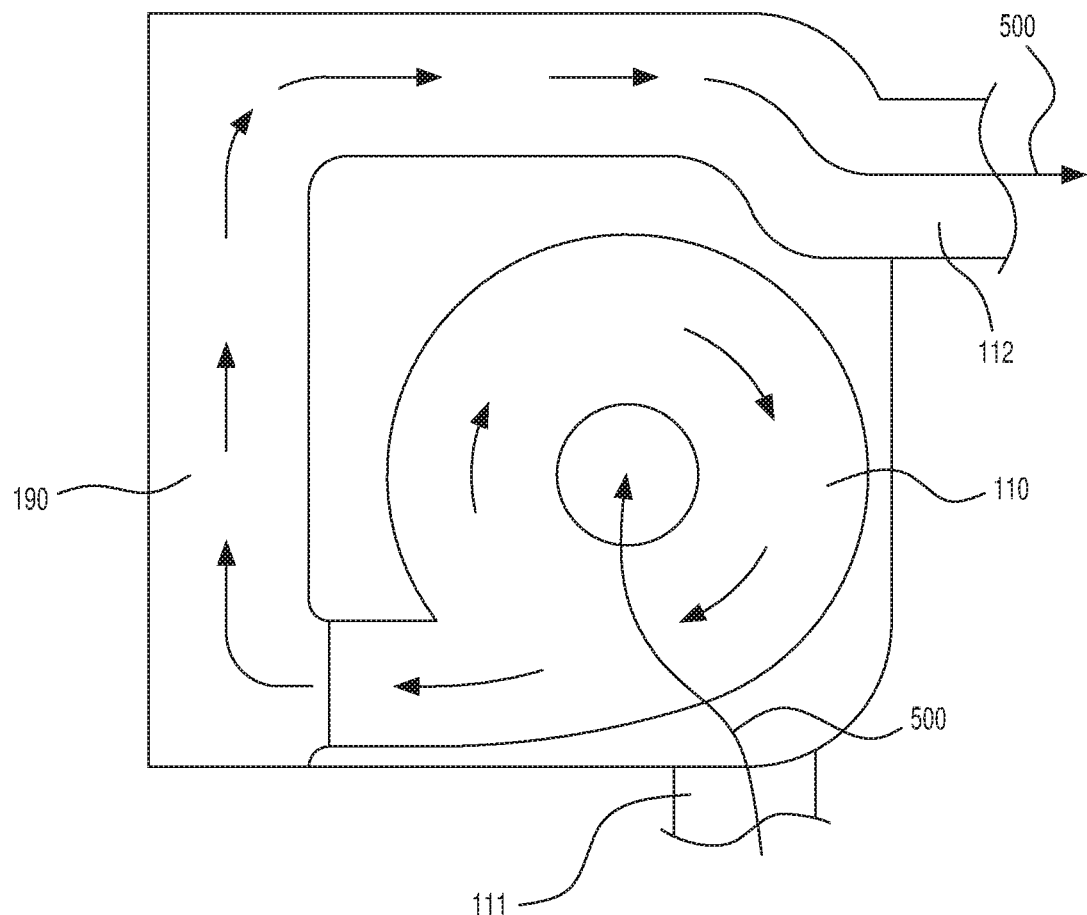
FIG. 32A is a schematic cross-sectional top view of a flow generator for a CPAP machine and showing gas channels through the flow generator.
Figure 32B:
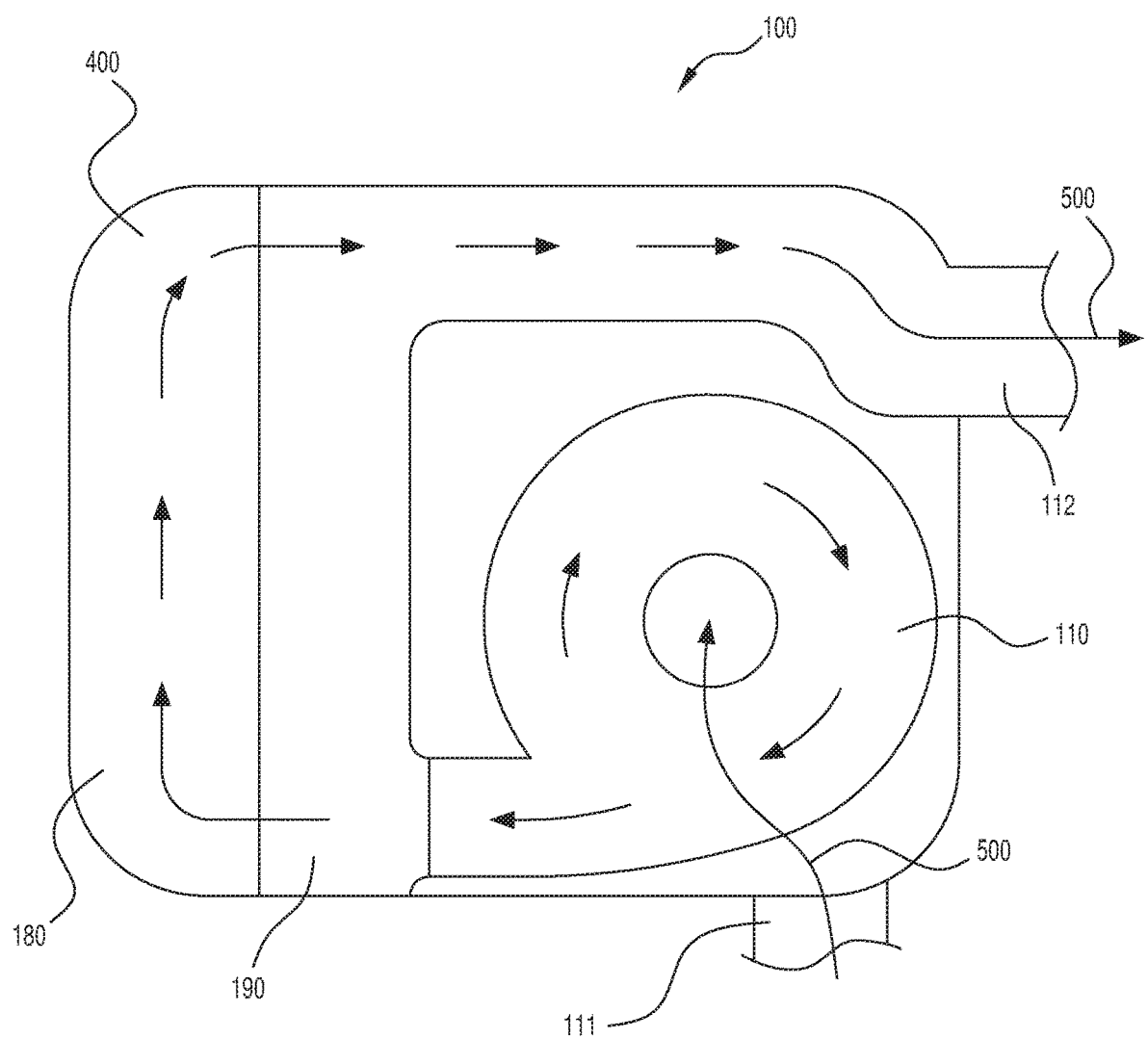
FIG. 32B is a schematic cross-sectional top view of the flow generator of FIG. 32A coupled to a humidifier.

In one form, a humidification device 100 or system 200 with dual gas channels/circuits 180, 190, as described above, may comprise a humidification module 400 that is modular in nature and may be configured to detachably attach to a flow generator 110. In this configuration, a patient may use the flow generator 110 alone, without the humidification module 400, as shown in FIG. 32A. For example, the bypass channel 190 may become the primary gas channel or flow path. When humidified gas is desired, a humidification module 400 may be attached to the flow generator 110 and at least a portion of the gas generated by the flow generator 110 is directed through the module 400. In one form, the humidification device 100 of FIGS. 16A to 31 and/or a humidification device as described above may form the humidification module 400 and be attached to the flow generator 110. Control valve(s) 170 may be operated to direct gas flow through the first gas channel 180 and/or second/bypass gas channel 190, as described above.

Figure 33:
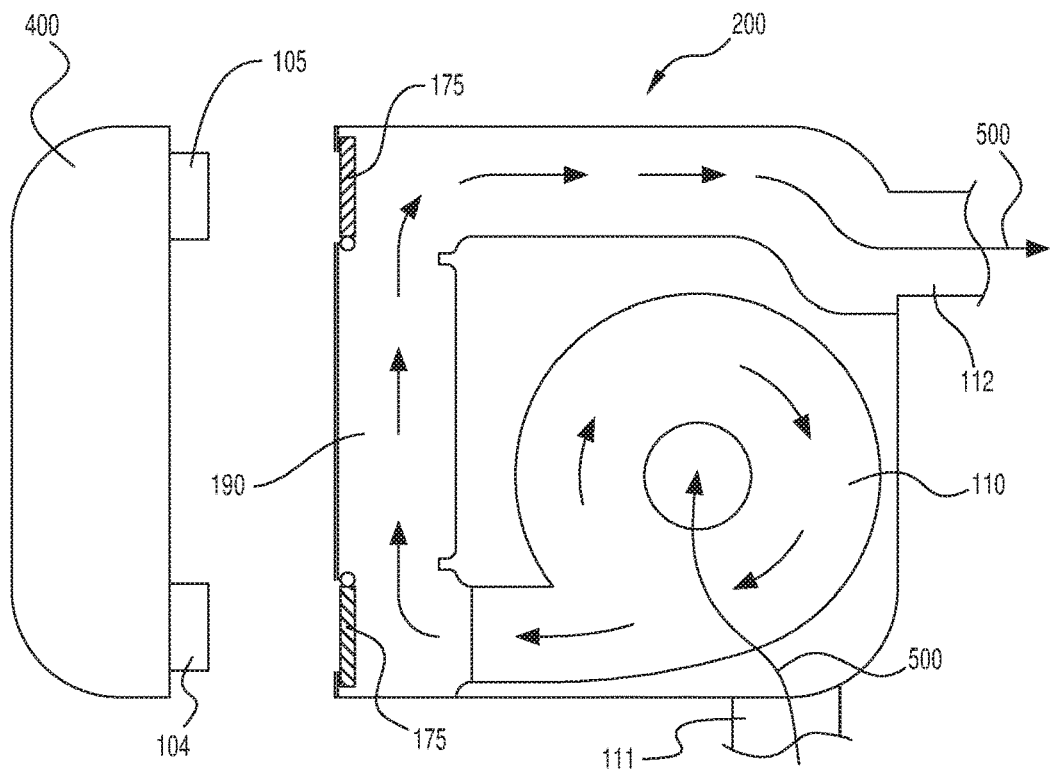
FIG. 33 is a schematic diagram showing one manner in which an in-line humidifier may couple to a flow generator.
Figure 33:
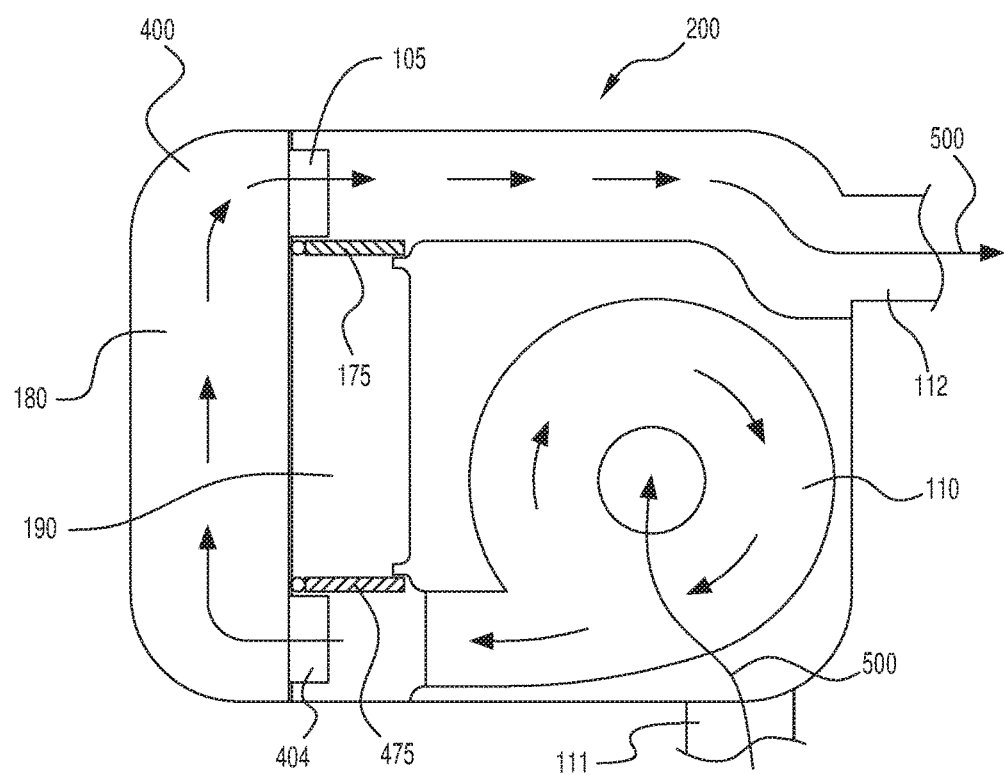

In one form, as shown in FIG. 33, a humidification device 100 and system 200 comprising a flow generator 110, having a gas inlet 111 and a gas outlet 112, and a detachably attachable humidification module 400 may comprise a control system comprising a trap door arrangement 175 to control gas flow within the device 100. In this form, the flow generator 110 may comprise at least one trap door that may be biased toward a first, closed position when the humidification module 400 is not attached to the flow generator 110. The humidification module 400 may be attached to the flow generator 110 using any suitable attachment system, such as using an interference or snap fit arrangement. The humidification device 100 may be configured so that the motion of attaching the humidification module 400 to the flow generator 110 may cause the trap door(s) 175 to move to an open position. For example, the humidification module 400 may comprise a protruding gas inlet 404 and a protruding gas outlet 405 that each press against one of a pair of trap doors 175 in the flow generator 110 when the humidification module 400 is attached to the flow generator 110. The pressure against each trap door 175 causes the trap doors to rotate about a respective hinge to a second, open position. In the open position, the trap doors block access to the second bypass gas channel 190 so that 100% of gas is directed through the humidification module 400. Conversely, when the humidification module 400 is detached from the flow generator 110, the trap doors 175 return to the closed position, allowing the gas to flow through the bypass channel 190. In one form, the trap doors 175 may comprise an attachment system comprising a latch mechanism to attach the humidification module 400 to the flow generator 110.

The trap door(s) 175 may be made of any suitable material or combination of materials, such as silicone, or thermoplastic, for example. In one form, the trap door(s) may be made of an overmoulded plastic part. A thermoplastic elastomer or silicone may provide the trap door(s) with characteristics that allow the trap door(s) to hinge from an initial position to a second position and to spring back to the initial position.

Figure 34:
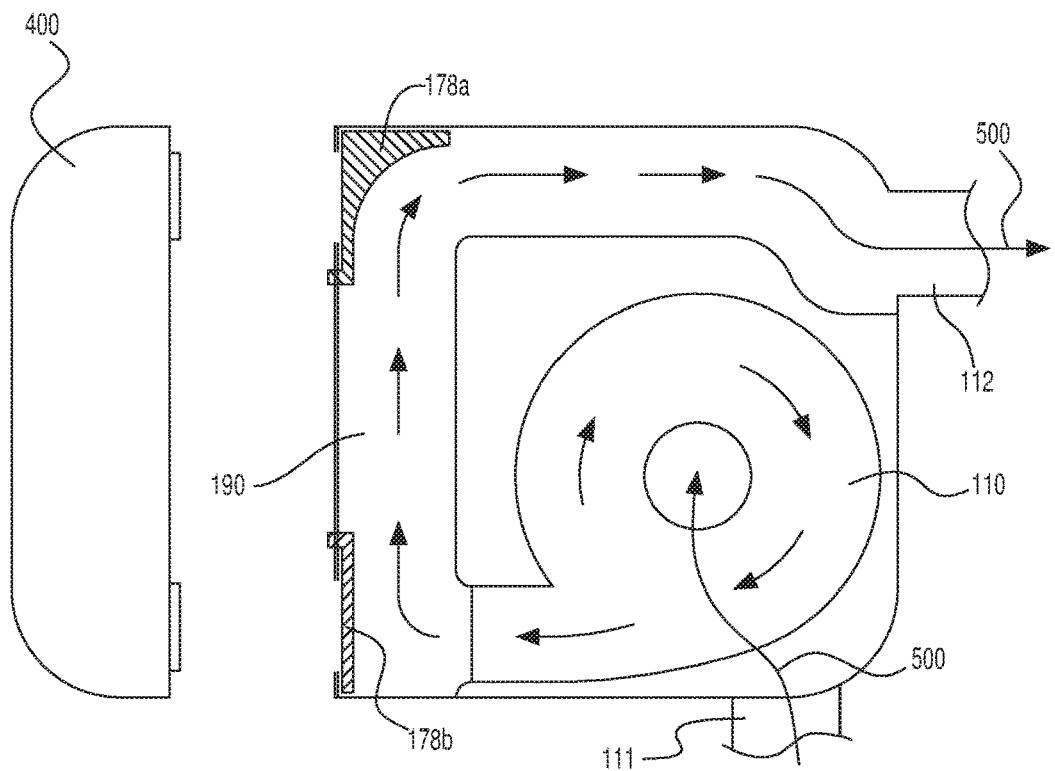
FIG. 34 is a schematic diagram showing another manner in which an in-line humidifier may couple to a flow generator having a sliding door system to direct the flow of gas through the humidifier and/or flow generator.
Figure 34:
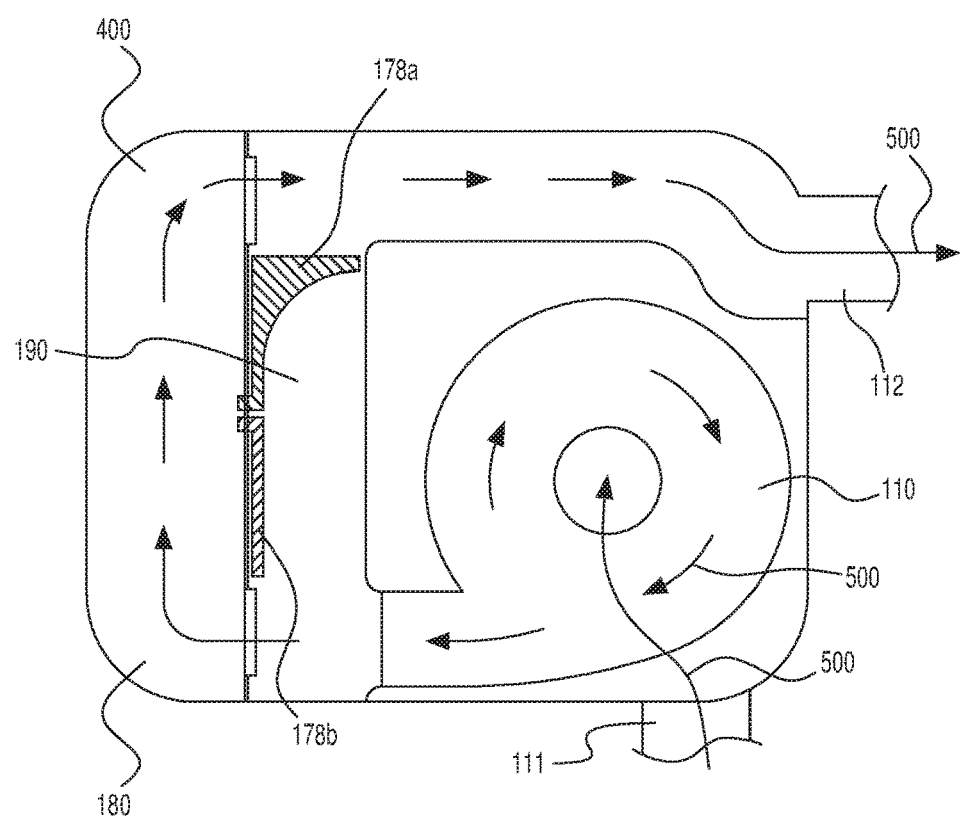

FIG. 34 shows another form of humidification system comprising a modular flow generator 110 and humidification module 400 having a control system comprising a sliding door arrangement to control gas flow within the system. In this form, the flow generator 110 comprises a pair of sliding doors 178*a* and 178*b*. In a first position, the sliding doors 178 allow gas from the flow generator 110 to flow along a bypass gas channel 190 within the flow generator 110 to provide gas at ambient humidity to a patient. For example, in the first position, the sliding doors 178 may be pushed toward the outer edges or corners of the flow generator 110 to be out of the way and to block the inlet 113 and outlet 114 ports of the flow generator that are configured to receive the gas inlet 404 and gas outlet 405 of the humidification module 400. The humidification module 400 may be detachably attached to the flow generator 110 by sliding the doors 178 away from the inlet and outlet ports 113, 114 to a second position, inserting the gas inlet 404 of the humidification module 400 into the inlet port 113 and inserting the gas outlet 405 of the humidification module 400 into the outlet port 114. In the second position, the sliding doors 178 may be pushed together so that the inlet and outlet ports 113, 114 are no longer blocked and gas 500 from the flow generator 110 is caused to pass through a first gas channel 180 in the humidification module 400 to humidify the gas 500. At least one sliding door 178 may be configured to block the bypass channel 190. For example, the first sliding door 178*a* may comprise an L shape with one leg of the L configured to slide along one wall of the flow generator 110 and the other leg of the L configured to block the bypass channel 190 when the door 178*a* is in the second position.

Figure 35A:
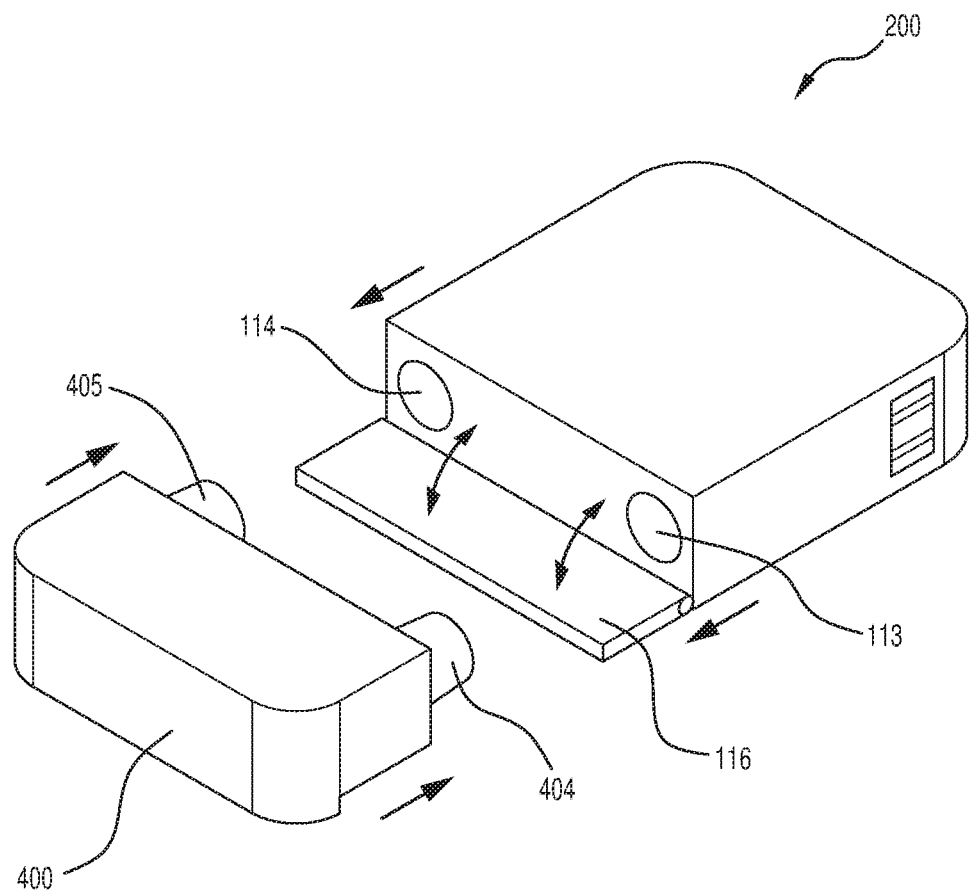
FIG. 35A is a schematic perspective view of a flow generator and humidifier configured to detachably attach to each other.
Figure 35B:
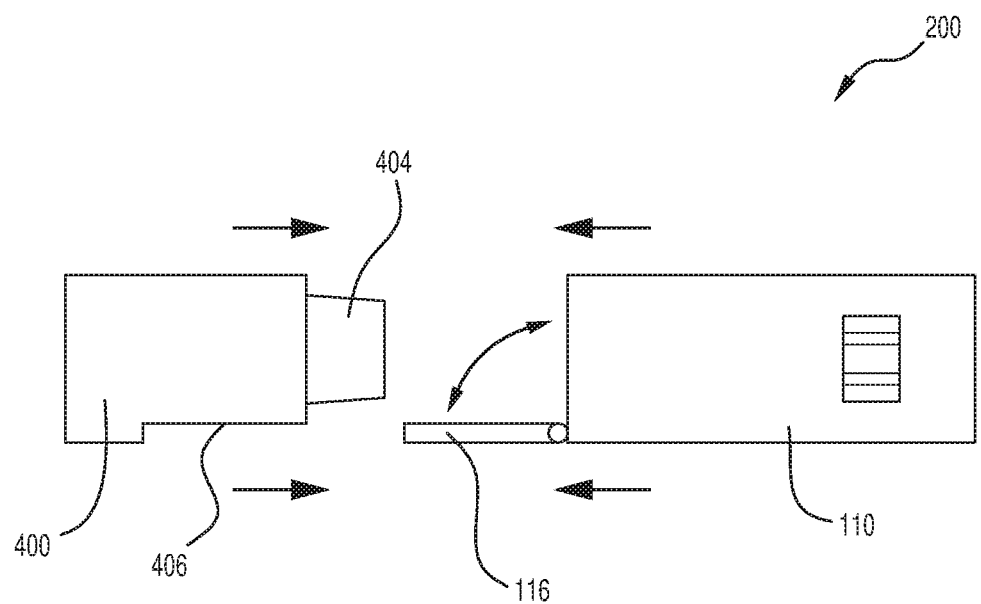
FIG. 35B is a schematic side view of the flow generator and humidifier of FIG. 35A.
Figure 35C:
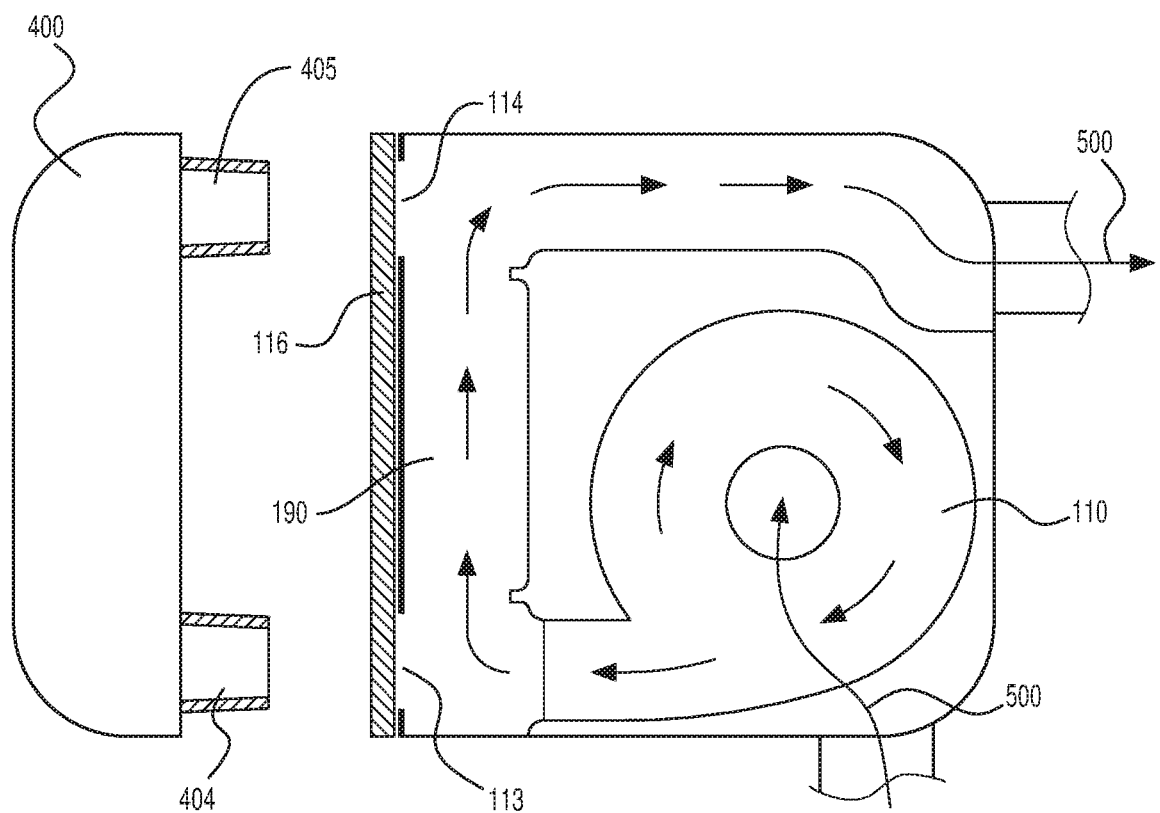
FIG. 35C is a schematic cross-sectional top view of a flow generator configured to couple to a humidifier as shown in the arrangement of FIG. 35A.
Figure 35D:
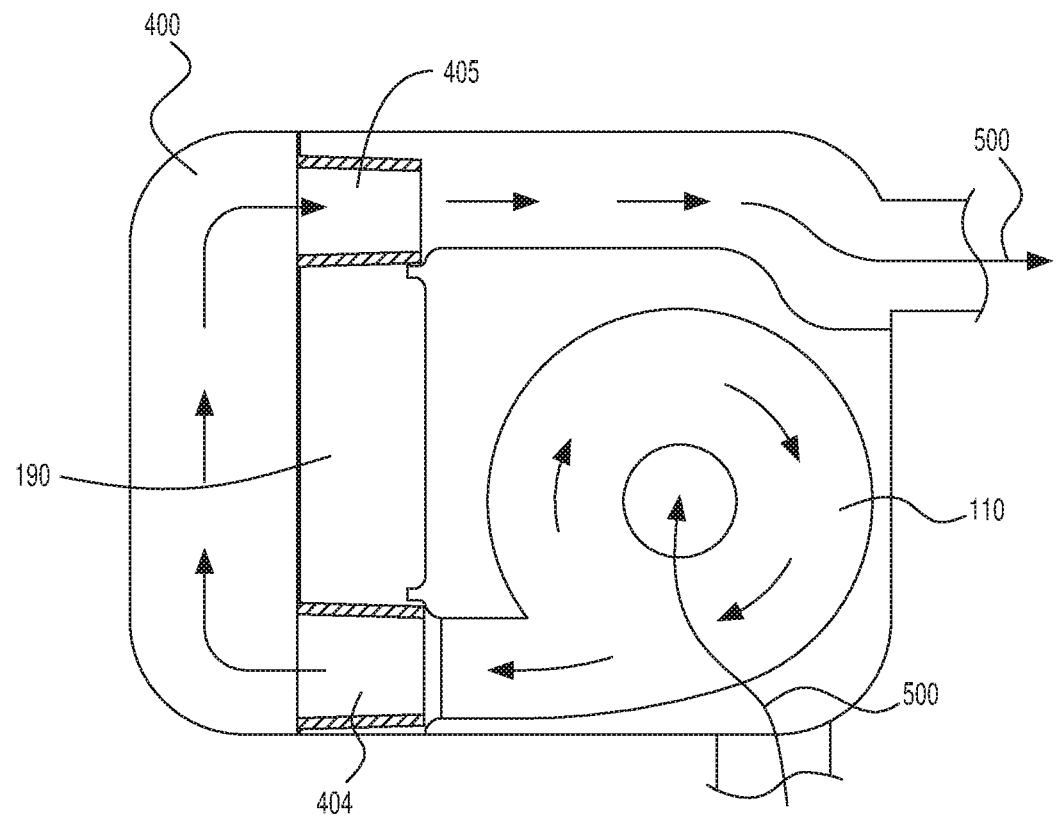
FIG. 35D is a schematic cross-sectional top view of the flow generator and humidifier of FIG. 35A coupled together.

In yet another form, as shown in FIGS. 35A to 35D, the flow generator 110 may comprise a hinged door 116 that closes to cover the inlet and outlet ports 113, 114 (as shown in FIG. 35C) and that hinges open (as shown in FIGS. 35A and 35B) to allow the gas inlet 404 of a humidification module 400 to engage with the inlet port 113 and the gas outlet 405 of the humidification module 400 to engage with the outlet port 114 when the humidification module 400 is detachably attached to the flow generator 110 (as shown in FIG. 35D). The humidification module 400 may comprise a recess 406 to receive a portion of the hinged door 116. In one form, the recess 406 is located on the underside of the humidification module 400 housing, as shown in FIG. 35B. The hinged door 116 may be configured to seal against the body of the flow generator 110 when closed. The hinged door 116 may be biased to the closed position or may be held in the closed position using a latch or some other suitable closure system. In the closed position, gas 500 is caused to flow along the bypass channel 190 of the flow generator 110. In the open position, gas 500 may flow through the humidification module 400. A control system, using control valves 170 or the like, as described above, may be used to control the flow of gas 500 through the first gas channel 180 in the humidification module 400 and the second, bypass channel 190 in the flow generator 110 so that gas can pass through the first channel 180, the second channel 190, or both channels.

In one form, the humidification module may be configured for retrofit insertion into a humidification device. In this form, the humidification module may comprise a wick chamber within which a wick may be held, as described above. The humidification module may also comprise at least one attachment member to detachably attach the humidification module to a flow generator of the humidification device.

In one form, the humidification system 200 may comprise a kit comprising a flow generator 110 in fluid connection with a non-humidified gas flow path/circuit to deliver non-humidified gas to a patient; a humidification module/humidifier 400 detachably attachable to the flow generator 110 and comprising a humidified gas flow path/circuit 180 to deliver humidified gas to a patient; and a control system to control the amount of gas that flows from the flow generator 110 through the humidified gas circuit 180 and the amount of gas that flows from the flow generator 110 through the non-humidified gas circuit 190.

The kit may also include a wick 131 for use with a wick humidifier 130 of the humidification module 400.

Many different forms of wick 131 may be used with the humidification devices/humidifiers 100 and humidification modules 400 described above. However, it is beneficial for the wick to be made from a material having one or more of the following properties:

1. Porous

Gas is required to be blown through or over the wick so that it can increase in humidity.

2. Hydrophilic

Wicking is dependent on capillary action and occurs when the Adhesion Forces between the molecules of a fluid and the wick surface surpass the Cohesion Forces between the fluid molecules. In wicks formed from hydrophilic materials, water/fluid is attracted to the surface of the wick, and therefore spreads out over the wicking elements when in contact with the wick. This phenomenon allows the wick to draw fluid upwards against gravity.

3. High Effective Surface Area

A high effective surface area increases the volume of fluid that can be exposed to gas directed across the wick and consequently increases the efficiency of the humidification device by increasing the humidity of gas after passing across the wick.

4. Non-Absorbent

It is beneficial for the wicking material to be minimally absorbent. If the material is highly absorbent, static fluid may accumulate in the core of the material, which will detrimentally provide conditions for accelerated bacterial growth.

5. Anti-Microbial/Anti-Fungal

A wick having anti-microbial and anti-fungal properties can reduce the frequency at which the wick needs to be cleaned and/or replaced. A wick may be provided with anti-microbial and anti-fungal properties in a number of ways known in the industry, such as by using anti-microbial layers or inserts into the wick or the fluid chamber.

Additionally or alternatively, the fluid itself may be treated prior to entering the reservoir, for example by an ultra-violet light emitting diode (LED).

Chemicals that inhibit bacteria growth may be used.

In one form, the wick may be disposable and replaceable or cleanable and re-usable. For example, the wick may be:

1. Removable

The wick chamber and the contained wick may be removable from the fluid chamber. In one form the wick chamber and/or wick may also be consumable. This allows for individual cleaning and/or replacement of the wick as required by the user. In another form, the entire fluid chamber may be consumable and replaceable.

The wick may also be easy to remove from the wick chamber and may be a consumable component (replaceable and/or cleanable). Certain materials that can be used in the wick, over longer periods of time can have a build-up of bacteria or impurities from the fluid used for humidification (hard water). It can therefore be beneficial to be able to clean the wick, and eventually replace the wick as necessary.

2. Cleanable

One way of increasing the longevity of the wick is to ensure that it is cleanable. In one form, the humidification device may come with instructions to clean the wick according to a set schedule, such as to clean the wick every two weeks or every 20 days. In another form, some manner of adaptive cleaning schedule could be provided for the user. The adaptive cleaning schedule may include providing an indication of the cleanliness of the wick. For example, the humidification device may comprise a guide to indicate to a user when to clean the wick. This can be done in a number of ways, for instance through the use of visual bacteria sensor/s, electronic bacteria sensors or other means.

In one form, the wick humidifier may comprise one or more physical sensors that are configured to detect the presence of bacteria in the apparatus and to provide a visual indication of the presence of bacteria and/or the type of bacteria and/or the extent of bacterial growth on the sensor(s).

In one form, a physical sensor may comprise an item, such as a substrate, that is configured to provide a visual indication of bacteria growing on the item. For example, the item may comprise a flexible plastic layer and a nutrient containing filter paper attached to the plastic layer. The physical sensor may be configured to show coloured spots, such as red spots, when aerobic bacteria forms on the sensor. The number of spots, together with the extent of background colouring/reddening can be used to quantitatively measure microbial growth on the sensor.

In one form, a chemical may be added to the sensor to provide a visual colour indication of bacterial growth.

In one form, a reactant may be impregnated into a material, such as filter paper, where the reactant is configured to cause a colour change in the filter paper when bacteria grow on the paper. For example, a Bradford assay may be used as the visual indication of bacterial growth. In this form, a material may be impregnated with a dye, such as Coomassie Brilliant Blue G-250 for example. When certain acidic conditions are met, due to the growth of bacteria, the sensor may change from red to blue as the dye binds to the protein being assayed.

In another form, a coating may be provided on one or both sides of the sensor and is configured to allow bacteria to grow on the coating.

If the wick comprises a suitable substrate, the physical sensor(s) may be located on the wick, or may be portions of the wick itself. For instance a portion of the wick may be impregnated with the previously described reactant, forming an integral bacteria sensor within the wick.

Alternately, the physical bacteria sensor(s) may be located within the water reservoir as opposed to being directly connected to the wick. This can be beneficial as the physical bacteria sensor/s can be replaced independently of the wick being cleaned. For example, after the user cleans the wick, the physical sensor can be replaced from the water reservoir.

In another form, the wick humidifier may comprise one or more electronic sensors in communication with a control system that are configured to detect the presence of bacteria in the apparatus. The electronic sensor(s) can be located on the wick support structure, or an interior surface of the water reservoir, and can be calibrated in such a way as to be useful to provide a measure of the bacteria present on the wick. For instance, even though the sensor is not located on the wick, or directly exposed to the bacteria on the wick, a correlation can be determined between a bacteria reading measured by the electronic sensor and the bacteria level within the wick, and this correlation can be used to provide a useful indication to the user when the bacteria level within the wick is elevated.

In some forms, the electronic sensor may be configured to alternatively or additionally detect the type of bacteria and/or the extent of bacterial growth on or near the sensor. For the sake of simplicity, preferred forms of sensor (both electronic and physical sensors) will be described herein as being configured to detect the presence of bacteria on or near the sensor, but it should be appreciated that this may alternatively or additionally include detecting the type of bacteria and or the extent of bacteria growth on or near the sensor.

In one form, the electronic sensor may be configured to provide a signal to the electronic control system that indicates whether bacteria has or has not been detected. For example, the electronic sensor may be configured to provide the control system with a signal when the presence of bacteria is detected, or when a certain type of bacteria is detected, or when a certain predetermined threshold level of bacterial population is detected. Alternatively, the control system may be configured to identify when a predetermined threshold level of bacteria has been detected by the sensor, such as after the sensor has generated a predetermined number of signals.

Upon receiving a signal from a bacteria sensor, or from a predetermined number of bacteria sensors, or upon receiving a predetermined number of signals from a bacteria sensor or from two or more bacteria sensors, the control system may be caused to change from a normal operating mode to an alert mode. The control system may be configured so that, in the alert mode, the system provides an indication/alert to a user interface that indicates to the user that the apparatus or a component of the apparatus needs to be cleaned as a result of bacterial growth. The alert may be any suitable form of indication to a user, including but not limited to a visual display (such as one or more lights, images, words, text message, email, colour changes, or symbols for example), and/or a sound indication (such as one or more beeps for example). Where the user interface is a remote user interface, such as a computer or a smartphone, for example, the control system may be configured to transmit the alert (in the form of an alert signal) to the user interface, which may then present the alert on a screen in any suitable form of visual indication, such as an image, words, symbols, colour changes, lights, for example. Alternatively, or additionally the remote user interface may be configured to present an audio alert, in the form of a noise, which may be of any suitable form, including beeps or other sounds.

In another form, the electronic bacteria sensor may be configured to generate an indication of bacteria detection, which may be a visual or audio indication. Optionally, electronic sensors that are configured to generate a visual alert may be located in areas of the apparatus that are easily visible to a user, such as in the interfacing structure. Additionally or alternatively, physical sensors configured to provide a visual indication of bacterial growth may be located in areas of the apparatus that are easily visible to a user.

An electronic bacteria sensor employed by a breathing treatment apparatus may be configured to operate continuously (in a continuous mode) or at fixed time intervals (in a periodic mode) to sense the presence of bacteria within the breathing treatment apparatus. Preferably, the control system comprises a clock and is configured to connect to the sensor to determine the mode of operation of the sensor.

In one form, the electronic sensor(s) may comprise a filter to filter out particles that are over a predetermined size.

In one form, an electronic bacteria sensor that may be used with the apparatus may comprise an electrochemical biosensor. This form of sensor may be configured to measure electrical impedance as a method of detecting bacteria in contact with the sensor. For example, the electronic bacteria sensor may comprise a sensing surface comprising a bio-recognition element and may be configured to produce a signal if the sensor identifies changes in electrical properties of the sensing surface, such as changes in impedance, capacitance, or resistance for example. These changes may occur as a result of interactions between the bio-recognition element on the sensor's sensing surface and bacteria to which the sensor is exposed.

An electronic bacteria sensor may be located at any suitable area of the apparatus. For example, an electronic bacteria sensor may be located inside the humidification compartment, such as above or below the water line of the water reservoir. If the sensor is located below the water line, the sensor may be configured to detect the presence of bacteria in the water contacting the sensing surface. If the sensor is located above the water line, the sensor may be configured to detect bacteria in condensation formed on the sensing surface as a result of elevated humidity levels within the humidification compartment during use.

Upon detection that the wick has an elevated bacteria level, the user may proceed to clean the wick in one of a number of ways.

In some embodiments, the wick is disposable, and can simply be removed from the wick chamber, disposed of, and replaced with a new wick.

In some embodiments, the wick can be cleaned by running an appropriate cleaning solution through the wick. In some embodiments, this may be hot water or a water/vinegar solution.

In some embodiments, the wick may be left to dry out for a predetermined period of time to sterilize. Alternately, the flow generator may pass air through or over the wick after the fluid supply in the fluid chamber and wick chamber is emptied to actively dry the wick.

In some embodiments, the humidification device may include a sterilization system. The sterilization system may be automatically activated on detection of a high bacteria level, and/or it may be manually activated by the user.

In one form, the sterilisation system comprises a series of ultra-violet lights, such as ultra-violet LED lights. The lights may be strategically located at any suitable location in the humidification device to sterilise the wick, such as in the interior of the fluid chamber or wick chamber. When the control system receives a signal from one or more sensors that causes the control system to identify the presence of bacteria, or to identify the presence of a certain type of bacteria, or to identify that a predetermined threshold of bacteria levels have been met, the control system may generate an alert and/or the control system may activate the sterilisation system.

If the control system activates the sterilisation system, the ultra-violet lights are turned on to kill bacteria within the wick. After the sterilisation process, the control system may automatically reset to the normal operating mode.

The invention claimed is:

1. A humidification device for use in CPAP, wherein the device comprises:
    a wick chamber configured to hold fluid;
    a wick positioned within the wick chamber and configured to absorb fluid from the wick chamber;
    at least one gas inlet to direct a flow of gas into the wick chamber; and
    a diffusion system with at least one diffusion surface positioned to diffuse the flow of gas before the flow of gas passes across the wick,
    wherein the wick chamber comprises a foraminous structure for supporting the wick within the wick chamber and diffusing gas flow through or over the wick.

2. The humidification device of claim 1, wherein the diffusion system comprises a diffuser to diffuse gas flowing from the at least one gas inlet and into the wick chamber substantially evenly through or over the wick.

3. The humidification device of claim 1, wherein the wick chamber comprises a baffle wall comprising diffusion apertures of varying sizes to diffuse gas flow through or over the wick.

4. The humidification device of claim 1, wherein the at least one gas inlet is located on a side of the wick chamber to direct gas through the wick from a side of the wick.

5. The humidification device of claim 1, wherein the at least one gas inlet enters the wick chamber at a transition region comprising a curved radius between the at least one gas inlet and an external wall of the wick chamber to encourage gas entering the wick chamber to diffuse by exploiting a Coanda effect.

6. The humidification device of claim 1, wherein the diffusion system comprises a blade diffuser to diffuse gas from the at least one gas inlet through the wick.

7. The humidification device of claim 1, wherein the wick supported by the wick chamber is annular in shape.

8. The humidification device of claim 7, wherein different regions of the wick have a different thickness to other regions.

9. The humidification device of claim 1, wherein in use, fluid within a fluid chamber is maintained at or below ambient temperature.

10. A humidification device for use in CPAP, wherein the device comprises:
    a wick chamber configured to hold fluid;
    a wick positioned within the wick chamber and configured to absorb fluid from the wick chamber;
    at least one gas inlet to direct a flow of gas into the wick chamber; and
    a diffusion system with at least one diffusion surface positioned to diffuse the flow of gas before the flow of gas passes across the wick,
    wherein the wick chamber comprises a baffle wall comprising diffusion apertures of varying sizes to diffuse gas flow through or over the wick.

11. The humidification device of claim 10, wherein the wick supported by the wick chamber is annular in shape.

12. The humidification device of claim 11, wherein different regions of the wick have a different thickness to other regions.

13. The humidification device of claim 10, wherein in use, fluid within a fluid chamber is maintained at or below ambient temperature.

14. A humidification device for use in CPAP, wherein the device comprises:
    a wick chamber configured to hold fluid, the wick chamber having a first end, a second end, and at least one sidewall extending in a lengthwise direction between the first end and the second end;
    a wick positioned within the wick chamber and configured to absorb fluid from the wick chamber;
    at least one gas inlet to direct a flow of gas into the wick chamber; and
    a diffusion system with at least one diffusion surface positioned to diffuse the flow of gas before the flow of gas passes across the wick,
    wherein the at least one gas inlet is located on a side of the wick chamber and is configured to direct gas through the wick in a direction offset from the lengthwise direction.

15. The humidification device of claim 14, wherein the wick supported by the wick chamber is annular in shape.

16. The humidification device of claim 15, wherein different regions of the wick have a different thickness to other regions.

17. The humidification device of claim 14, wherein in use, fluid within a fluid chamber is maintained at or below ambient temperature.

18. A humidification device for use in CPAP, wherein the device comprises:
   a wick chamber configured to hold fluid;
   a wick positioned within the wick chamber and configured to absorb fluid from the wick chamber;
   at least one gas inlet to direct a flow of gas into the wick chamber; and
   a diffusion system with at least one diffusion surface positioned to diffuse the flow of gas before the flow of gas passes across the wick,
   wherein the at least one gas inlet enters the wick chamber at a transition region comprising a curved radius between the at least one gas inlet and an external wall of the wick chamber to encourage gas entering the wick chamber to diffuse by exploiting a Coanda effect.

19. The humidification device of claim 18, wherein the wick supported by the wick chamber is annular in shape.

20. The humidification device of claim 19, wherein different regions of the wick have a different thickness to other regions.

21. The humidification device of claim 18, wherein in use, fluid within a fluid chamber is maintained at or below ambient temperature.

22. A humidification device for use in CPAP, wherein the device comprises:
   a wick chamber configured to hold fluid;
   a wick positioned within the wick chamber and configured to absorb fluid from the wick chamber;
   at least one gas inlet to direct a flow of gas into the wick chamber; and
   a diffusion system with at least one diffusion surface positioned to diffuse the flow of gas before the flow of gas passes across the wick,
   wherein the diffusion system comprises a blade diffuser to diffuse gas from the gas inlet through the wick.

23. The humidification device of claim 22, wherein the wick supported by the wick chamber is annular in shape.

24. The humidification device of claim 23, wherein different regions of the wick have a different thickness to other regions.

25. The humidification device of claim 22, wherein in use, fluid within a fluid chamber is maintained at or below ambient temperature.

* * * * *